US012788814B2

(12) United States Patent
Beasley et al.

(10) Patent No.: US 12,788,814 B2
(45) Date of Patent: Nov. 10, 2026

(54) PEPTIDE-CENTRIC CHIMERIC ANTIGEN RECEPTORS TO CANCER SELF-PEPTIDES

(71) Applicants: THE CHILDREN'S HOSPITAL OF PHILADELPHIA, Philadelphia, PA (US); MYRIO THERAPEUTICS PTY LTD, Blackburn North (AU)

(72) Inventors: Matthew Beasley, Blackburn North (AU); Ben Kiefel, Blackburn North (AU); John Maris, Philadelphia, PA (US); Mark Yarmarkovich, Philadelphia, PA (US); Fiona Gracey, Blackburn North (AU); Nickolaos Sgourakis, Philadelphia, PA (US); John Warrington, Philadelphia, PA (US); Quinlen Marshall, Philadelphia, PA (US)

(73) Assignees: The Children's Hospital of Philadelphia, Philadelphia, PA (US); Myrio Therapeutics Pty Ltd, Blackburn North (AU)

( * ) Notice: Subject to any disclaimer, the term of this patent is extended or adjusted under 35 U.S.C. 154(b) by 424 days.

(21) Appl. No.: 18/685,663

(22) PCT Filed: Aug. 23, 2022

(86) PCT No.: PCT/US2022/075362
§ 371 (c)(1),
(2) Date: Feb. 22, 2024

(87) PCT Pub. No.: WO2023/028494
PCT Pub. Date: Mar. 2, 2023

(65) Prior Publication Data

US 2024/0352130 A1 Oct. 24, 2024

Related U.S. Application Data

(60) Provisional application No. 63/236,556, filed on Aug. 24, 2021.

(51) Int. Cl.

| | |
|---|---|
| ***C07K 16/00*** | (2006.01) |
| ***A61K 39/395*** | (2006.01) |
| ***A61K 39/42*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07H 21/02*** | (2006.01) |
| ***C07H 21/04*** | (2006.01) |
| ***C07K 16/28*** | (2006.01) |
| ***C12N 5/02*** | (2006.01) |
| ***C12N 5/16*** | (2006.01) |
| *A61K 39/00* | (2006.01) |

(52) U.S. Cl.
CPC .............. *A61K 40/11* (2025.01); *A61K 40/31* (2025.01); *A61K 40/4213* (2025.01); *A61K 40/4242* (2025.01); *A61P 35/00* (2018.01); *C07K 16/2833* (2013.01); *A61K 2039/505* (2013.01); *A61K 2239/31* (2023.05); *A61K 2239/38* (2023.05); *A61K 2239/47* (2023.05); *C07K 2317/33* (2013.01); *C07K 2317/622* (2013.01)

(58) Field of Classification Search
None
See application file for complete search history.

(56) References Cited

U.S. PATENT DOCUMENTS

2021/0213058 A1 7/2021 Maris et al.

FOREIGN PATENT DOCUMENTS

| | | |
|---|---|---|
| JP | 2017-534261 | 11/2017 |
| JP | 2021-517810 | 7/2021 |
| WO | WO2016/044605 | 3/2016 |
| WO | WO2019/178081 | 9/2019 |
| WO | WO2019/205783 | 10/2019 |
| WO | WO2023/164425 | 8/2023 |

OTHER PUBLICATIONS

Genbank Accession 7MJA_C: Chain C, Paired mesoderm homeobox protein 2B peptide, Apr. 19, 2021, 1 page.
Dauger et al. "Phox2b controls the development of peripheral chemoreceptors and afferent visceral pathways". *Development* 130, 6635, doi:10.1242/dev.00866 (2003).

(Continued)

*Primary Examiner* — Chun W Dahle
(74) *Attorney, Agent, or Firm* — pH IP Law

(57) ABSTRACT

The neuroblastoma immunopeptidome is enriched with peptides derived from proteins essential for tumorigenesis including the unmutated peptide QYNPIRTTF (SEQ ID NO: 1) discovered on HLA-A*24:02 which is derived from the neuroblastoma dependency gene and master transcriptional regulator PHOX2B. To target QYNPIRTTF, peptide-centric chimeric antigen receptors (PC-CARs) were developed via a counter panning strategy using predicted potentially cross-reactive peptides. Informed by computational modeling, PHOX2B peptide¬ centric CARs were demonstrated to also recognize QYNPIRTTF (SEQ ID NO: 1) presented by HLA-A*23:01 and the highly divergent HLA-B*14:02. Potent and specific killing of neuroblastoma cells expressing these HEAs in vitro was shown along with complete tumor regression in mice.

19 Claims, 48 Drawing Sheets
(34 of 48 Drawing Sheet(s) Filed in Color)
Specification includes a Sequence Listing.

(56) References Cited

OTHER PUBLICATIONS

Dharia et al., "A first-generation pediatric cancer dependency map". *Nature Genetics* 53, 529-538, doi:10.1038/s41588-021-00819-w (2021).
Extended European Search Report for EP22862234.6 dated Mar. 24, 2025, 9 pages.
Hata et al., Diagnostic Utility of PHOX2B in Primary and Treated Neuroblastoma and in Neuroblastoma Metastatic to the Bone Marrow. *Archives of Pathology & Laboratory Medicine* 139, 543-546, doi:10.5858/arpa.2014-0255-OA (2015).
Hung, et al.. "PHOX2B reliably distinguishes neuroblastoma among small round blue cell tumours". *Histopathology* 71, 786-794 (2017).
International Search Report and Written Opinion for PCT/US22/75362; dated Jan. 19, 2023, 22 pages.
Kunert et al., "T-cell Receptors for Clinical Therapy: In Vitro Assessment of Toxicity Risk". *Clinical Cancer Research* 23, 6012-6020, doi:10.1158/1078-0432.Ccr-17-1012 (2017).
Mosse et al., "Germline PHOX2B mutation in hereditary neuroblastoma". *Am J Hum Genet* 75, 727-730, doi:10.1086/424530 (2004).
Nerli & Sgourakis, "Structure-based modeling of SARS-CoV-2 peptide/HLA-A02 antigens". *bioRxiv*, 2020.2003.2023.004176, doi:10.1101/2020.03.23.004176 (2020).
Park et al., "Targets and Antibody Formats for Immunotherapy of Neuroblastoma", *Journal of Clinical Oncology*, 1836-1848, 2020.
Richards et al., "CAR T Cell Therapy for Neuroblastoma", *Frontiers in Immunologyi*, vol. 9, p. 2380, 2018.
Toors et al., "Chain C. Paired mesoderm homeobox protein 2B peptide", Genbank entry (online); National Center for Biotechnology Information; Apr. 19, 2021; retrieved Nov. 15, 2022 from world wide web ncbi.nlm.nih.gov/protein/7MJA_C.
Tsherniak et al. Defining a Cancer Dependency Map. *Cell* 170, 564-576.e516, doi: 10.1016/j.cell.2017.06.010 (2017).
Yarmarkovich et al., "Cross-HLA targeting of intracellular oncoproteins with peptide-centrics CARs", *Nature*, 623(7988):820-827, 2023.
Yarmarkovich et al., "Targeting of intracellular oncoproteins with peptide-centric CARs", *Nature*, 599(7885):477-484, 2021.
Office Action for JP Appl. No. 2024-511998 dated Jun. 26, 2026, 14 pages with Engl. translation.
Yarmarkovich et al., "Abstract 1493: Discovery and Car T targeting of lineage-restricted neuroblastoma oncoproteins", 81(13 Suppl), 1 page, 2021.

(B)

(A)

(B)

| | EFCA36 | FDFT1 | KLHL1 | MX2 | MY07B | SARS | SLC23A2 |
|---|---|---|---|---|---|---|---|
| Peptide score | 27 | 20 | 29 | 19 | 33 | 19 | 21 |
| Overall score | 3.9 | 569 | 0.6 | 20 | 1.6 | 106 | 257.6 |
| Normal tissue | *F* | *T* | *F* | *F* | *F* | *F* | *T* |
| 10HL | 1.27 | 0.92 | 1.37 | 0.66 | 0.82 | 1.03 | 1.11 |
| 10LH | 0.00 | 0.09 | 0.01 | 0.00 | 0.30 | 0.00 | 0.00 |
| 280HL | 1.01 | 0.92 | 1.27 | ND | 0.88 | 0.87 | 1.07 |
| 320HL | 0.89 | 0.43 | 0.83 | 0.39 | 0.80 | 0.82 | 0.84 |
| 320LH | 0.68 | 0.39 | 0.53 | 0.35 | 0.95 | 0.70 | 0.88 |
| 302LH | 0.40 | 0.36 | 0.29 | 0.33 | 0.48 | 0.35 | 0.38 |

CAR cross-reactivity

FIG. 6

| Parent gene | Peptide | Relative Binding : PHOX2B | Normal Tissue Ligandome |
|---|---|---|---|
| **PHOX2B** | **QYNPIRTTF** | 1.00 | F |
| ABCA8 | MWQAIRATF | 0.36 | F |
| MYO7B | RQSPWRIYF | 0.30 | F |
| FDFTI | HYSPIYLSF | 0.08 | T |
| C6orf99 | RSTAIRQTF | 0.04 | F |
| MAPT3A | QDAPLEFTF | 0.01 | F |
| NLRC5 | REAPIHLDF | 0.01 | F |
| KLHL1 | TQQPARTLF | 0.01 | F |
| CHRNA3 | IYPDITYSL | 0.01 | F |
| EFCAB6 | CWRPMRRTF | 0.00 | F |
| XPR1 | QPAPAWTTF | 0.00 | F |
| SLC23A2 | SYLPISPTF | 0.00 | T |
| TNS4 | VQKAISTTF | 0.00 | T |
| CGNL1 | YEAPVSYTF | 0.00 | F |
| SARS | GYIPIYTPF | 0.00 | F |
| ATG16LI | RTNAIKQTF | 0.00 | F |
| MX2 | LYNKIREDF | 0.00 | F |

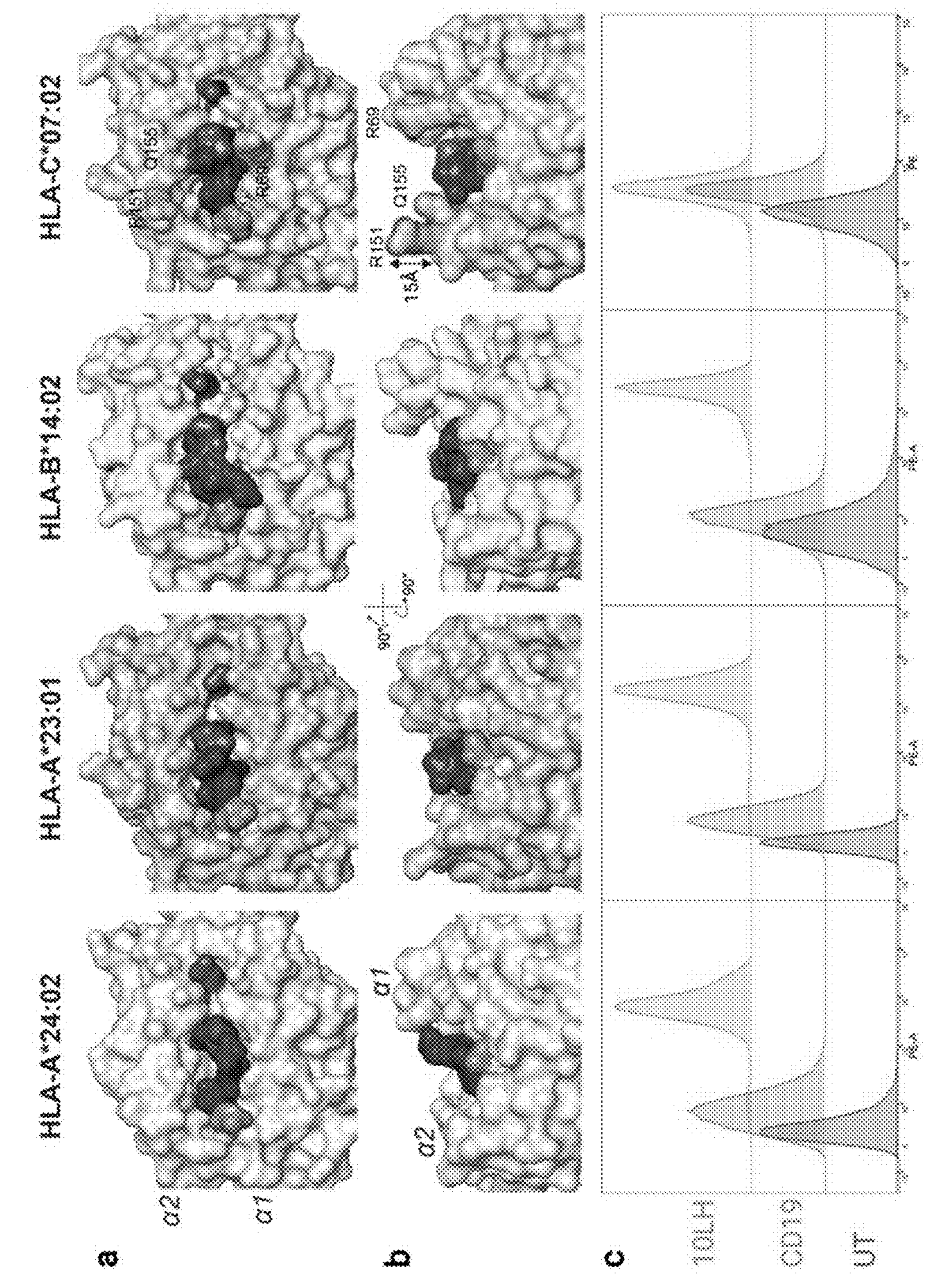
FIG. 8A-C (A)

(B)

(B)

(D)

(E)

(F)

(G)

(H)

(A)

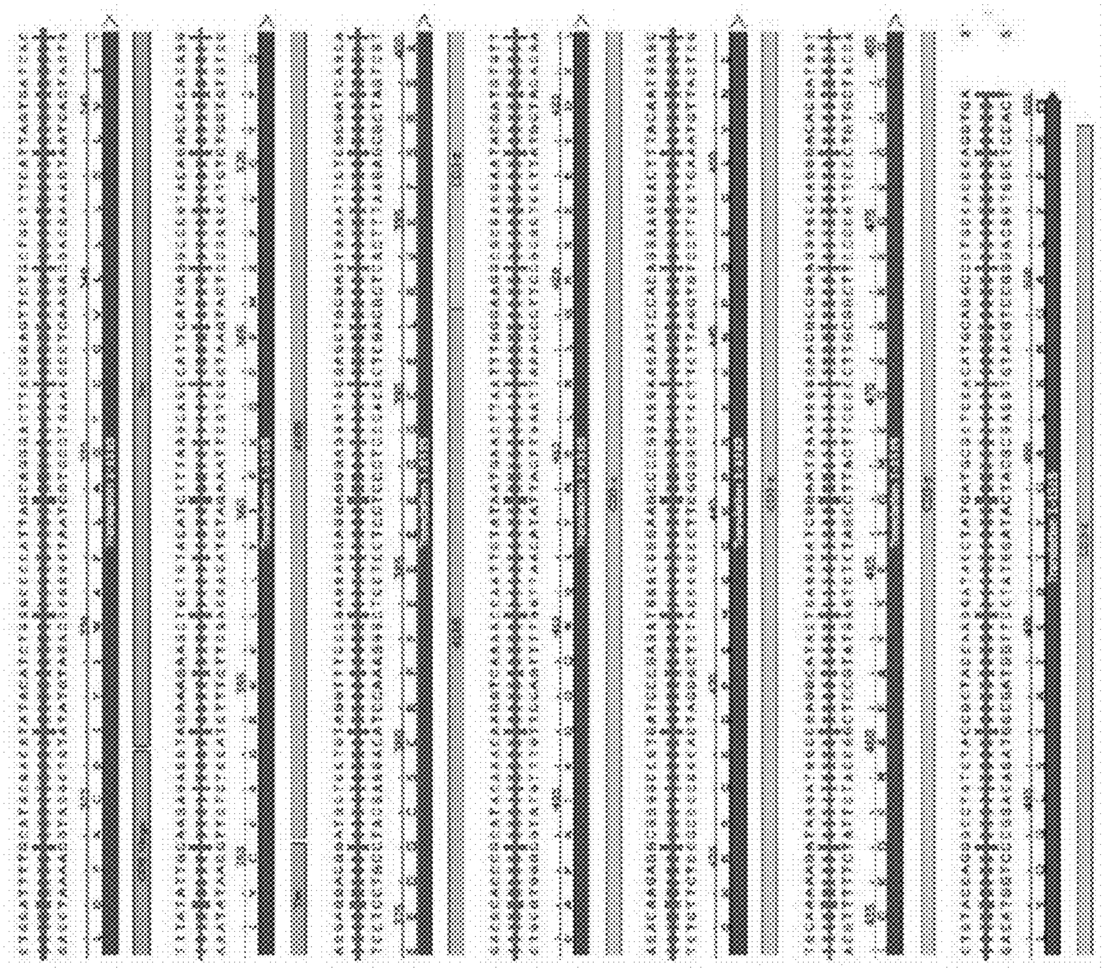
FIG. 15A, continued
(A)

(B)

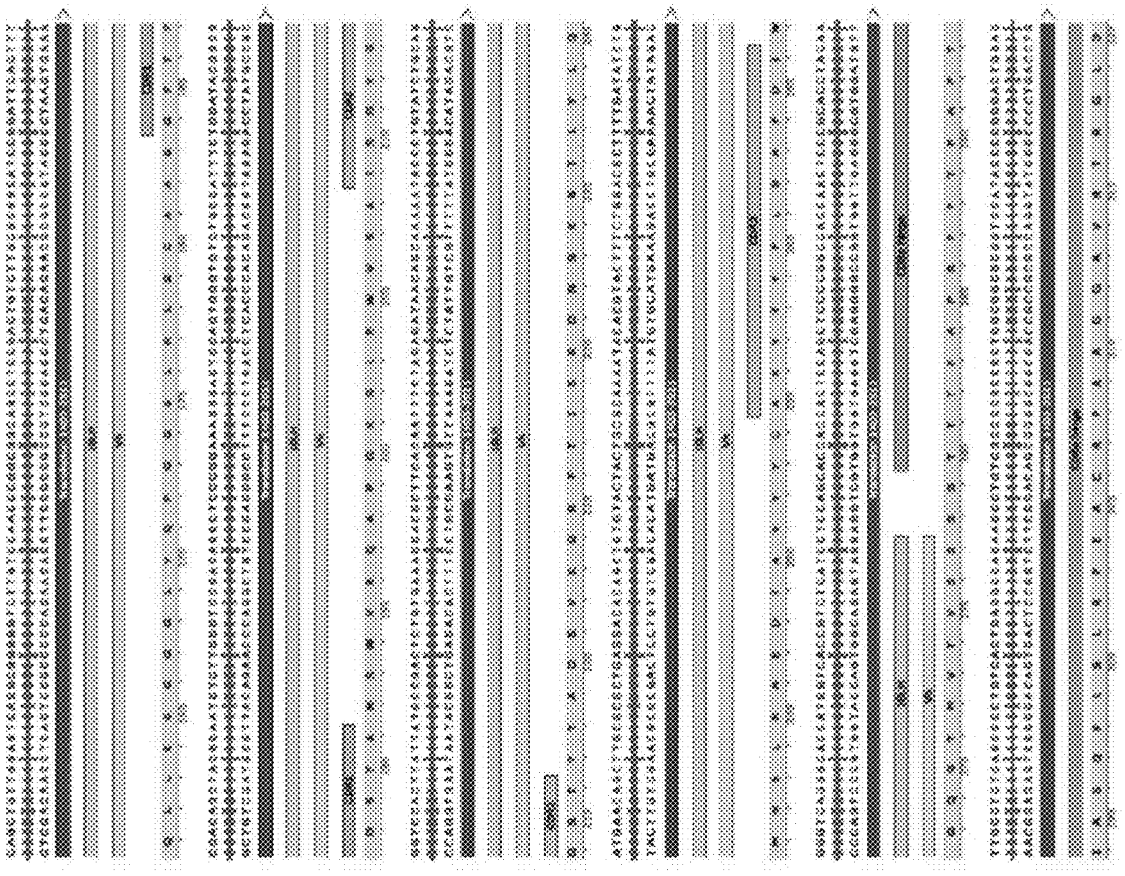
FIG. 15B, continued
(B)

(B)
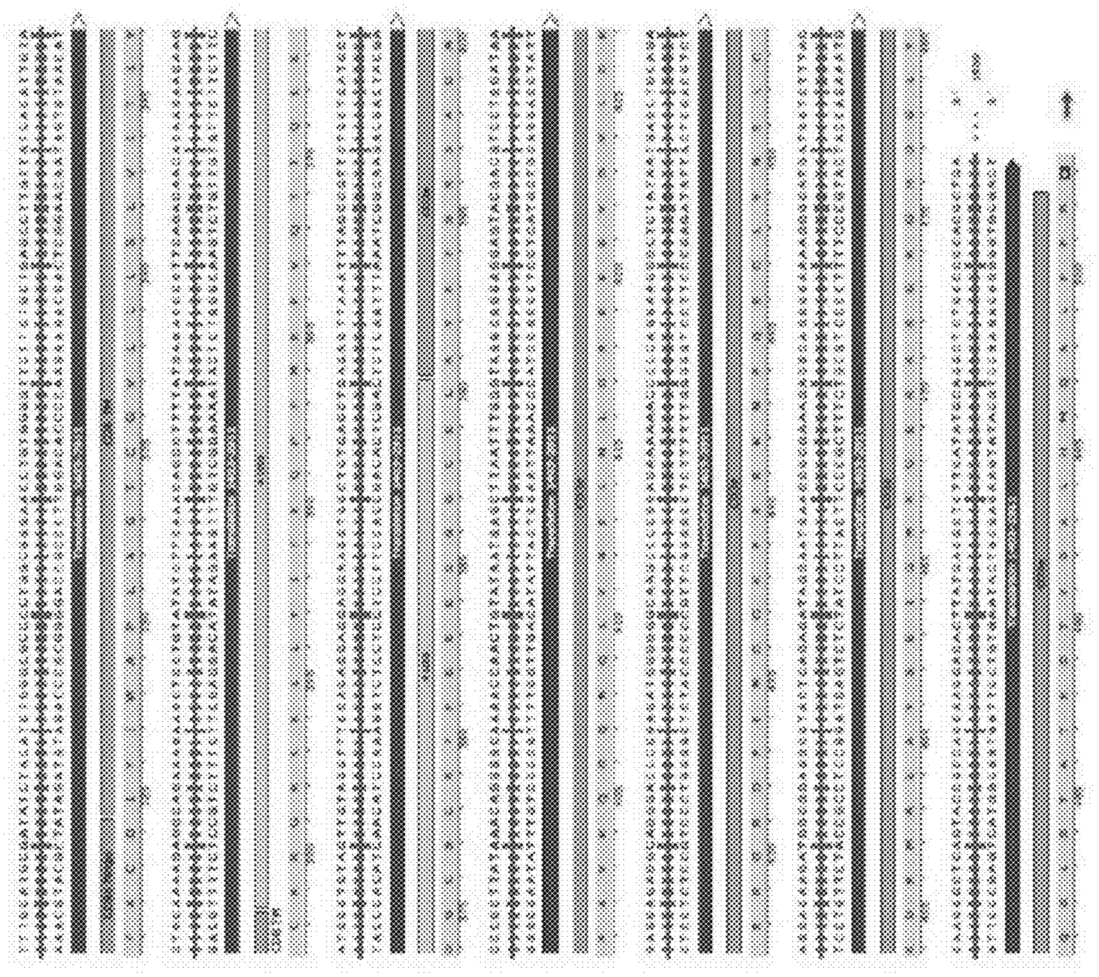
FIG. 15B, continued (A)

(B)

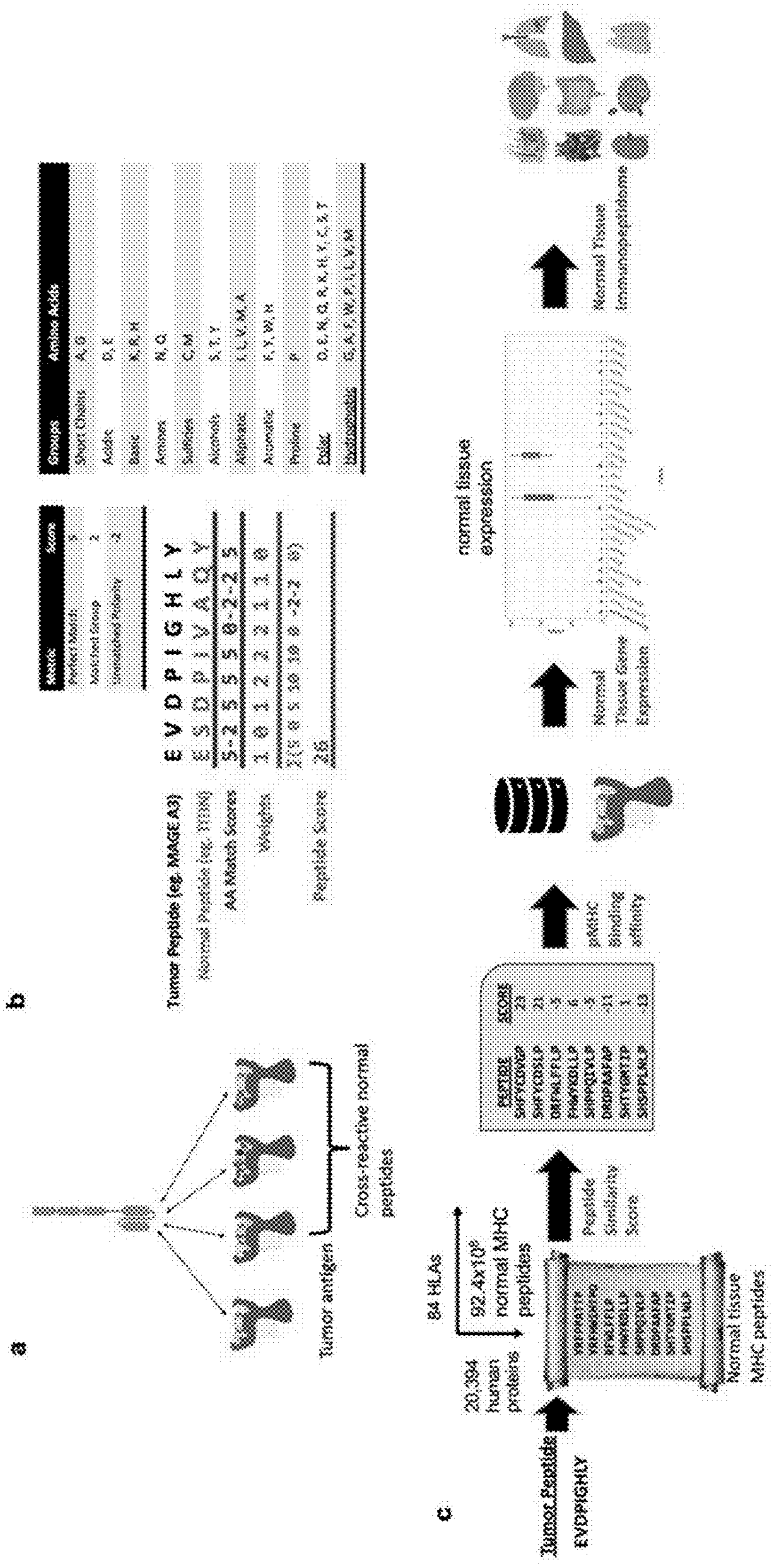
FIG. 25A-C a

| Rank | Peptide_Score | Peptides | Gene_Name | Max_norm | Max_tissue | Binding | Overall_score |
|---|---|---|---|---|---|---|---|
| | 50 | EVDPIGHLY | MAGEA3 | 8.849127 | Testis | 11.43 | |
| 1 | 25 | LSDPVGTCY | ITGA5 | 1238.931519 | Blood Vessel | 3.46 | 8235.7 |
| 2 | 32 | YTDPVGVLY | LCAT | 105.2805 | Liver | 2.18 | 1447.7 |
| 3 | 24 | FLEPLGLAY | LENG8 | 270.2617493 | Uterus | 6.87 | 944.1 |
| 4 | 36 | ESDPIVAQY | TTN | 261.3758 | Muscle | 8.07 | 842.1 |
| 5 | 25 | YIDPIAMEY | LAT2 | 141.4919 | Blood | 5.7 | 620.4 |
| 6 | 25 | LQDPLGLAY | RGS14 | 401.9189 | Brain | 20.36 | 493.5 |
| 7 | 25 | EMDPVTQLY | ALCAM | 110.1399 | Skin | 5.68 | 484.8 |
| 8 | 25 | CTFPLGWLY | ELOVL5 | 391.8979492 | Breast | 27.21 | 360.1 |
| 9 | 28 | VSDPVGVLY | JKAMP | 43.49138 | Brain | 3.91 | 311.4 |
| 10 | 24 | QLDGLGFLY | ACSBG2 | 227.0139 | Testis | 22.79 | 239.1 |
| 11 | 28 | SLDPLAMLY | TSHZ1 | 34.86856 | Ovary | 6.23 | 145.5 |
| 12 | 24 | GTDPAADLY | DNAH1 | 18.27267 | Testis | 4.7 | 93.3 |
| 13 | 23 | DSDPTGTAY | SUOX | 38.187 | Kidney | 8.62 | 90.9 |
| 14 | 30 | PLDPLGHNY | CILP | 238.8102 | Adipose Tissue | 96.56 | 74.2 |

1,143,861 peptides b

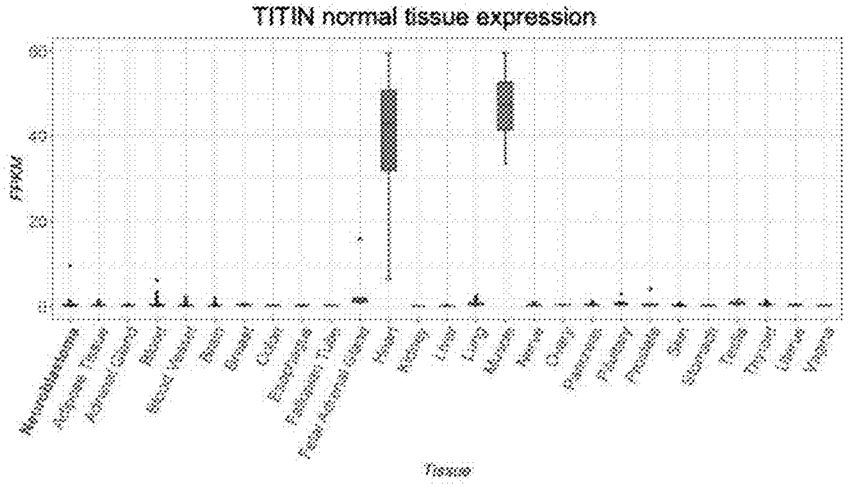

FIG. 26A-B

PEPTIDE-CENTRIC CHIMERIC ANTIGEN RECEPTORS TO CANCER SELF-PEPTIDES

STATEMENT REGARDING FEDERALLY FUNDED RESEARCH

This invention was made with government support under grants U54 CA232568 and R35 CA220500 awarded by National Institutes of Health. The government has certain rights in the invention.

PRIORITY CLAIM

This application is a national phase application of international application No. PCT/US2022/075362 filed Aug. 23, 2022, which claims benefit of priority to U.S. Provisional Application Ser. No. 63,236,556, filed Aug. 24, 2021, the entire contents of which are hereby incorporated by reference.

REFERENCE TO A SEQUENCE LISTING

This application contains a Sequence Listing XML, which has been submitted electronically and is hereby incorporated by reference in its entirety. Said XML Sequence Listing, created on Aug. 23, 2022, is named CHOPP0049WO.xml and is 68,758 bytes in size.

FIELD

The present disclosure relates generally to binding agents and methods of use therefor for diagnosing and/or treating cancer. In particular, the disclosure relates to binding agents capable of specifically binding to peptide:MHC complexes displaying peptides derived from human PHOX2B.

BACKGROUND

The major histocompatibility (MHC) system, also known as known as human leukocyte antigens (HLA) in humans, presents peptide antigens to T cells. Recognition by T cells of specific peptide:MHC (pMHC) complexes is mediated by the T-cell receptor (TCR). This recognition contributes to antigen-specific expansion of T cells and other immunological effects. From a biomedical perspective, pMHC complexes represent potential markers for disease status and targets for immunotherapy. Binding agents that recognise pMHC complexes have proven difficult to generate by conventional methods. One reason for this difficulty is the nature of the epitope. A pMHC-specific binding agent must recognize structural features of the peptide antigen as well as the MHC molecule. Typical pMHC-displayed peptide antigens are only 9 to 12 residues in length with some of those residues buried within the pMHC complex. This limits the number of surface-accessible residues that are free to interact with a binding agent. Typical antibody epitopes involve a greater number of amino acid residues than the peptide antigen alone provides. For a binding agent to achieve specific binding to a pMHC complex, either the epitope must be smaller than typically required for specific binding or the epitope must encompass portions of the MHC molecule in addition to the peptide. Put another way, antibodies that bind only to the peptide without expanding the epitope to the MHC molecule will in most cases lack the affinity required for a useful pMHC binding agent. Thus, the epitope for pMHC binding agents will in most cases extend to the MHC molecule.

However, if the interaction between the binding agent and pMHC complex depends too much upon interactions with the MHC molecule, then the binding agent will bind non-specifically to pMHC complexes displaying non-target peptide antigens. Finally, binding agents that bind the MHC independent of the peptide displayed are incapable of distinguishing MHC complexes displaying other peptides from pMHC complexes of interest.

From a theoretical perspective, native TCRs should have overcome this specificity problem and should prove useful as binding agents for pMHC complexes. This has not, however, proven to be the case. Native TCR receptors have been cloned from epitope-reactive T cell populations. Studies of these cloned TCRs have demonstrated that they have surprisingly low affinity for their cognate pMHC complexes—typically micromolar (μM) dissociation constants. Also, native TCRs rarely have the binding specificity necessary for practical use as binding agents for pMHC complexes, with a single TCR able to recognize many different epitopes and selectivity within the immune system achieved by deleting self-reactive T-cells.

In contrast to TCRs, antibodies generally have much higher affinities for their targets but efforts to raise antibodies against pMHC complexes have similarly foundered. Traditional techniques for antibody discovery, namely, animal vaccination or library screening, rarely succeed in generating pMHC binding agents with useful binding characteristics.

Neuroblastoma is a childhood cancer derived from tissue of the developing sympathetic nervous system and is often lethal despite intensive cytotoxic therapy[16]. These tumors are low in mutational burden[17-21] and MHC expression[22,23], making neuroblastoma both a challenging tumor to target with MHC-based immunotherapies. Previous work had identified PHOX2B as being highly and specifically expressed in neuroblastoma tissues[83], as well as being mutated in cases of familial inheritance of the disease[84,85].

Consistent with its function in orchestrating neural crest progenitor development[48,49], PHOX2B is expressed exclusively during fetal development and is completely silenced in normal tissues prior to birth. PHOX2B expression is routinely used in neuroblastoma diagnostic assays[51,52], is one of two highly penetrant susceptibility genes in neuroblastoma[53], and is the third most significant dependency in neuroblastoma as reported in DepMap[3,54]. Taken together, the inventors suggest that PHOX2B is a highly specific tumor antigen in neuroblastoma and an ideal candidate for therapeutic targeting.

The patent WO2019/178081 analyzed the immunopeptidome (the repertoire of peptides displayed as peptide-MHC complexes) of 16 neuroblastoma tumours and determined a number of peptides that were presented by different human peptide-MHC alleles, among which was a PHOX2B-derived peptide, QYNPIRTTF (SEQ ID NO: 1), presented by the HLA-A*24:02 subtype.

A binding agent specific to this HLA-A*24:02 PHOX2B peptide complex would meet a great unmet need to treat and diagnose neuroblastoma in pediatric patients.

SUMMARY

The present disclosure a binding agent comprising an antigen-binding site that specifically binds an HLA $PHOX2B_{QYNPIRTTF}$ complex, comprising a peptide having the sequence QYNPIRTTF (SEQ ID NO: 1), an HLA α-chain polypeptide and a $\beta_2$ microglobulin polypeptide. The antigen-binding site may bind to the HLA PHOX2B$_{QYNPIRTTF}$ complex with a dissociation constant ($K_D$) equal to or less than about 500 nM, equal to or less than about 200 nM, or equal to or less than about 13 nM. The binding agent may not MHC-restricted. The antigen-binding site may bind the HLA PHOX2B$_{QYNPIRTTF}$ complex presented by two or more of, three or more of, or four or more of HLA-A*24:02, HLA-A*23:01, HLA-B*14:02, HLA-C*07:01, HLA-C*06:02, HLA-A*29:02, and HLA-A*32:01.

The antigen-binding site may comprise:

a) a $V_L$ comprising a CDR-L1 region as set forth in SEQ ID NO: 6, a CDR-L2 region as set forth in SEQ ID NO: 7, and a CDR-L3 region as set forth in SEQ ID NO: 8; and/or b) a $V_H$ comprising a CDR-H1 region as set forth in SEQ ID NO: 9, a CDR-H2 region as set forth in SEQ ID NO: 10, and a CDR-H3 region as set forth in SEQ ID NO: 11;

or a) a $V_L$ comprising a CDR-L1 region as set forth in SEQ ID NO: 15, a CDR-L2 region as set forth in SEQ ID NO: 16, and a CDR-L3 region as set forth in SEQ ID NO: 17; and/or b) a $V_H$ comprising a CDR-H1 region as set forth in SEQ ID NO: 18, a CDR-H2 region as set forth in SEQ ID NO: 19, and a CDR-H3 region as set forth in SEQ ID NO: 20;

or a) a $V_L$ comprising a CDR-L1 region as set forth in SEQ ID NO: 26, a CDR-L2 region as set forth in SEQ ID NO: 27, and a CDR-L3 region as set forth in SEQ ID NO: 28; and/or b) a $V_H$ comprising a CDR-H1 region as set forth in SEQ ID NO: 29, a CDR-H2 region as set forth in SEQ ID NO: 30, and a CDR-H3 region as set forth in SEQ ID NO: 31;

or a) a $V_L$ comprising a CDR-L1 region as set forth in SEQ ID NO: 35, a CDR-L2 region as set forth in SEQ ID NO: 36, and a CDR-L3 region as set forth in SEQ ID NO: 37; and/or b) a $V_H$ comprising a CDR-H1 region as set forth in SEQ ID NO: 38, a CDR-H2 region as set forth in SEQ ID NO: 39, and a CDR-H3 region as set forth in SEQ ID NO: 40;

or a) a $V_L$ comprising a CDR-L1 region as set forth in SEQ ID NO: 44, a CDR-L2 region as set forth in SEQ ID NO: 45, and a CDR-L3 region as set forth in SEQ ID NO: 46; and/or b) a $V_H$ comprising a CDR-H1 region as set forth in SEQ ID NO: 47, a CDR-H2 region as set forth in SEQ ID NO: 48, and a CDR-H3 region as set forth in SEQ ID NO: 49.

The binding agent may comprise a $V_H$ and a $V_L$, wherein the $V_H$ has at least 75%, at least 90%, at least 95%, at least 99%, or 100% sequence identity to SEQ ID NO: 5, and/or wherein the $V_L$ has at least 75%, at least 90%, at least 95%, at least 99%; or 100% sequence identity to SEQ ID NO: 4; or which comprises a $V_H$ and a $V_L$, wherein the $V_H$ has at least 75%, at least 90%, at least 95%, at least 99%, or 100% sequence identity to SEQ ID NO: 14, and/or wherein the $V_L$ has at least 75%, at least 90%, at least 95%, at least 99%, or 100% sequence identity to SEQ ID NO: 13; or which comprises a $V_H$ and a $V_L$, wherein the $V_H$ has at least 75%, at least 90%, at least 95%, at least 99%, or 100% sequence identity to SEQ ID NO: 25, and/or wherein the $V_L$ has at least 75%, at least 90%, at least 95%, at least 99%, or 100% sequence identity to SEQ ID NO: 24; or which comprises a $V_H$ and a $V_L$, wherein the $V_H$ has at least 75%, at least 90%, at least 95%, at least 99%, or 100% sequence identity to SEQ ID NO: 34, and/or wherein the $V_L$ has at least 75%, at least 90%, at least 95%, at least 99%, or 100% sequence identity to SEQ ID NO: 33; or which comprises a $V_H$ and a $V_L$, wherein the $V_H$ has at least 75%, at least 90%, at least 95%, at least 99%, or 100% sequence identity to SEQ ID NO: 43, and/or wherein the $V_L$ has at least 75%, at least 90%, at least 95%, at least 99%, or 100% sequence identity to SEQ ID NO: 42.

The binding agent may be an antibody. The binding agent may comprise a $V_H$ and a $V_L$, wherein the $V_H$ is fused to the $V_L$. The binding agent may be selected from the group consisting of mAb, Fab, Fab', F(ab')$_2$, Fv, Dab single-chain antibody, scFv, chimeric antigen receptor (CAR), ADC, Killer Ig-Like receptor (KIR), BiTE, BsMAb and TFP, such as a single chain variable fragment (scFv) or a modular Bispecific T cell-like Engager (BiTE). The intracellular signaling domain may be CD3 epsilon, CD3 gamma, CD3 delta, TCR alpha, TCR beta.

Also provided in an isolated polynucleotide comprising a nucleic acid sequence encoding the binding agent as described herein, or an expression vector comprising such as polynucleotide operatively linked to a cis-acting regulatory element. Also provided is a cell comprising the such a polynucleotide or expression vector. Also provided is a pharmaceutical composition comprising the binding agent, the isolated polynucleotide, the expression vector or the cell.

In another embodiment, there is provided a method of detecting a cancer cell, comprising contacting the cell with the binding agent as described herein, under conditions which allow the binding agent to bind to the HLA PHOX2B$_{QYNPIRTTF}$ complex, wherein binding of the binding agent to the HLA PHOX2B$_{QYNPIRTTF}$ complex or the level thereof is indicative of the cancer cell. In yet another embodiment, there is provided a method of diagnosing and treating cancer in a subject in need thereof, comprising a) detecting the presence of cancer cells in the subject according to such a method, diagnosing the subject as having cancer when cancer cells are detected; and optionally treating the subject with an anti-cancer therapy. The cancer cell may be a neuroblastoma.

A further embodiment provides for a method of treating a cancer, comprising administering to a subject in need thereof a therapeutically effective amount of the binding agent, the isolated polynucleotide, the vector, the cell, or the pharmaceutical composition as described herein. The can cancer may be a neuroblastoma.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIG. 1A is clone 10, and FIG. 1B is clone 302.

FIG. 2A is clone 10, and FIG. 2B is clone 302.

FIG. 3A is clone 10, and FIG. 3B is clone 302.

FIG. 6. sCRAP specificity testing of clone 10 and clone 302 CARs. The figure depicts the prediction of potential cross-reactive peptides to the PHOX2B epitope by the sCRAP algorithm and the testing of CAR constructs of clones 10 and 302 as scFv in the VL-VH and VH-VL orientations. Fluorophore-labelled MHC tetramers were loaded with the peptides and used to stain cells transduced with the CAR constructs. Clones that retained selectivity were further prioritized (selective receptors marked with arrow). Peptide score represents the predicted cross-reactivity based on the amino acid sequences of normal-tissue peptides; overall score calculated based on peptide score, binding affinity, and normal tissue expression; T denotes peptides that have been reported in the normal tissue immunopeptidome, while F denotes their absence.

FIGS. 8A-C. Structural basis of CARs binding PHOX2B peptide presented on multiple HLAs. FIG. 8A depicts PHOX2B/HLA-A24 crystal structure and models of PHOX2B in complex with HLA-A*23:01, HLA-B*14:02, and HLA-C*07:02. FIG. 8B depicts R151, Q155 and R69 charged and polar residues of HLA-C07 align with key 10LH interaction residues I5, R6, and I7 (MHC residues in blue and PHOX2B/10LH interaction residues in red). R151, Q155 and R69 create steric and charged hindrance of in key peptide binding residues. FIG. 8C depicts staining of PHOX2B PC-CAR 10LH (bottom) reveals strong binding to HLA-A*24:02, HLA-A*23:01, and HLA-B*14:02, but not HLA-C07. 10LH; PHOX2B PC-CAR; CD19; CD19-directed CAR; UT; untransduced T cells.

FIG. 9A demonstrates binding of the 10 LH and 302 LH CARs to labelled PHOX2B 43-51 HLA-A*23:01 tetramer. FIG. 9B demonstrates that 10LH CAR kills HLA-A*23:01/PHOX2B-WM873 cells when pulsed with PHOX2B peptide but not with CHRNA3 peptide.

FIG. 16A is clone 9, FIG. 16B is clone 1114.

FIG. 18A is clone 9, and FIG. 18B is clone 1113.

FIG. 20A is clone 9, and FIG. 20B is clone 1113.

FIGS. 25A-C. sCRAP cross-reactivity algorithm. FIG. 25A depicts the cross-reactivity algorithm was developed to identify peptides presented on normal tissue with similar biophysical properties to tumor antigens such as to preemptively predict cross-reactivities and screen for specificity. FIG. 25B is an illustration of peptide scoring system described in methods. FIG. 25C is a schematic of algorithm workflow describing how tumor peptides are scored against each peptide predicted to be presented from the normal proteome (totaling $92.4\times10^6$ potential MHC peptides). Binding affinity is predicted for each normal peptide and maximum gene expression of parent gene are factored into the overall score of each peptide. Peptides are referenced against a normal tissue immunopeptidomics database.

FIGS. 26A-B. pMHC Cross-Reactivity Algorithm sCRAP Predicts MAGE-A3 toxicity through TITIN. FIG. 26A is a table of top predicted cross-reactive peptides to MAGE-A3 peptide EVDPIGHLY (SEQ ID NO: 59) reveals cross-reactivity with Titin peptide ESDPIVAQY (SEQ ID NO: 60) ranks $4^{th}$ out of 1,143,861 potential peptides presented on HLA-A*01:01. FIG. 26B demonstrates TITIN is highly expressed in heart and muscle tissues.

FIG. 29. PHOX2B-specific bispecific antibody mediated cytotoxicity of HLA-A*24:02 or HLA-A*23:01 expressing cell lines in vitro.

DETAILED DESCRIPTION

Figure 1A:
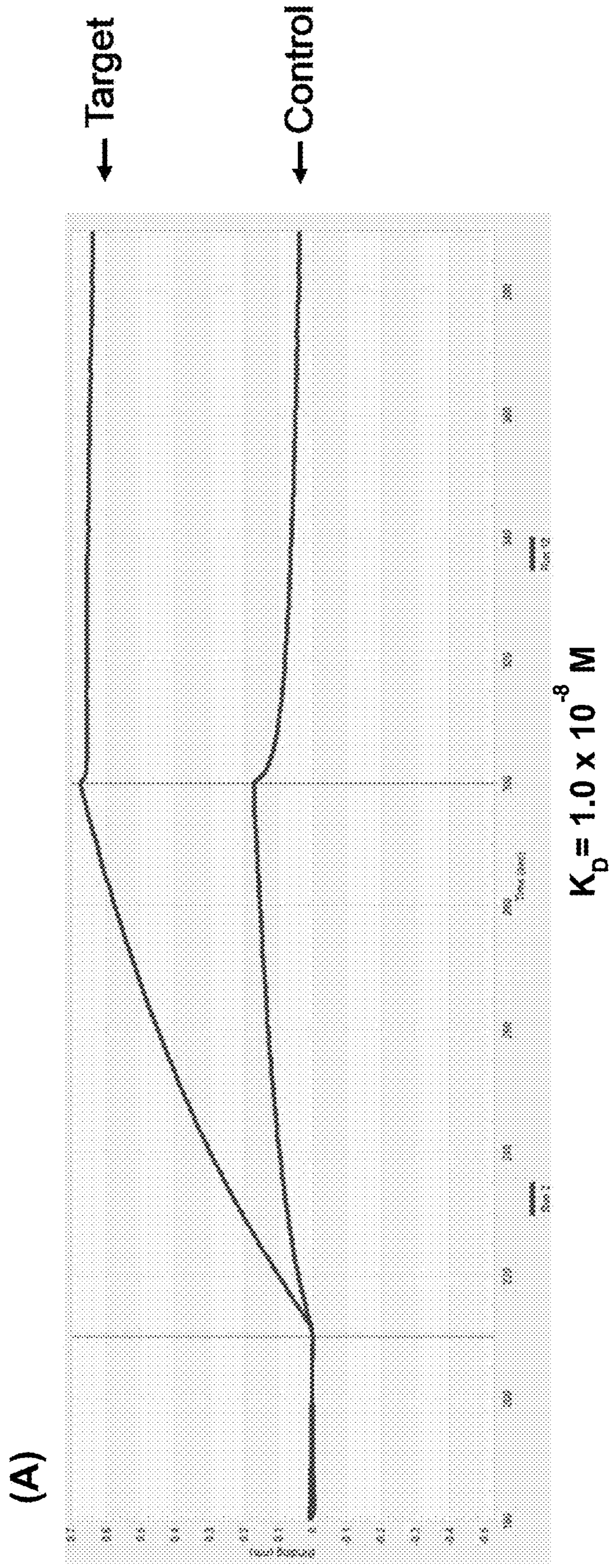
FIGS. 1A-B. Kinetic analysis of clones 10 and 302. The figures depict the association and dissociation of soluble PHOX2B (43-51) A*24:02 complex with scFv of clone 10 or clone 302, as measured by bio-layer interferometry (BLI). The binding PHOX2B (43-51) complex (200 nM) is overlaid with a non-specific complexes (3×200 nM) control that demonstrates specific binding only to the PHOX2B (43-51) complex. Arrow labelled 'Target' shows scFv binding to the PHOX2B (43-51) MHC complex. Arrow labelled 'Controls' shows scFv binding to three pMHC complexes with unrelated peptides.

The curative potential of chimeric antigen receptor (CAR) T cell-based cancer immunotherapies has been established in leukemias, but solid tumor applications have been limited by a paucity of known tumor-specific membrane proteins[1,2]. Though membrane proteins represent up to a quarter of the proteome, only a fraction of these are specifically expressed on tumors cells and not on normal tissues, and a smaller proportion are essential to tumor homeostasis[3]. Rather, the vast majority of cancer driver proteins reside in the cytoplasm or nucleus of the cell, where they are accessible to the immune system only through presentation of peptides on the major histocompatibility complex (MHC).

MHC class I proteins, encoded by the highly polymorphic human leukocyte antigen (HLA) A, B, and C genes, present a snapshot of the intracellular proteome on the cell surface (immunopeptidome) where T cells surveil the peptide-MHC complexes (pMHC) for antigens derived from foreign pathogens[4]. T cell recognition of mutation-derived pMHCs (neoantigens) as non-self is the basis of curative responses achieved through immune checkpoint blockade[5] and complete remissions using adoptive transfer of tumor infiltrating lymphocytes (TILs)[6]. Nonetheless, only ~5% of these neoantigens are predicted to bind a given HLA allotype[7], and just 1.6% of neoantigens are reported to be immunogenic[8]. Subclonal mutations and downregulation of mutated non-essential genes further constrain the pool of therapeutically relevant neoantigens, necessitating a mutational threshold for effective neoantigen-based therapies that is not surpassed in most cancers[9,10]. Tumor cells also present a plethora of unmutated self-peptides on MHC[11], but these are largely immunogenically silent due to negative thymic selection of T cells. The inventors hypothesized that a subset of the immunopeptidome consists of tumor-specific peptides derived from essential oncoproteins and that these can be targeted using synthetic peptide-centric chimeric antigen receptors (PC-CARs).

Peptides presented in the MHC groove make up only a small fraction of the extracellular pMHC molecular surface. The typical 8-14mer peptide presented on MHC class I composes only ~2-3% of the amino acids in the pMHC complex and is spatially confined within the adjacent alpha-helices of the MHC groove, thus posing major challenges for engineering peptide-specific single-chain antibody variable fragment (scFv) binders[12]. Furthermore, cross-reactivity of engineered receptors with peptides of biophysically similar molecular surfaces presented in normal tissues have resulted in significant toxicity and death[13-15].

Here, the inventors present the immunotherapeutic targeting of the neuroblastoma CRC master regulator PHOX2B using PC-CARs specific against the PHOX2B peptide QYNPIRTTF (SEQ ID NO: 1) in complex with HLA-A*24:02, but also in HLA-A*23:01 and HLA-B*14:02. These and other aspects of the disclosure are set out in detail below.

I. Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, antibodies and related molecules, cell and tissue culture, molecular biology, and protein and oligo- or polynucleotide chemistry and hybridization described herein are those well-known and commonly used in the art.

Standard techniques are used for recombinant DNA, oligonucleotide synthesis, and cell culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., B. Perbal, A Practical Guide to Molecular Cloning, John Wiley and Sons (1984); J. Sambrook et al., Molecular Cloning: A Laboratory Manual, Cold Spring Harbour Laboratory Press (1989); T. A. Brown (editor), Essential Molecular Biology: A Practical Approach, Volumes 1 and 2, IRL Press (1991); D. M. Glover and B. D. Hames (editors), DNA Cloning: A Practical Approach, Volumes 1-4, IRL Press (1995 and 1996); and F. M. Ausubel et al. (editors), Current Protocols in Molecular Biology, Greene Pub. Associates and Wiley-Interscience (1988, including all updates until present); Ed Harlow and David Lane (editors) Antibodies: A Laboratory Manual, Cold Spring Harbour Laboratory (1988); and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md. (1987 and 1991); Bork et al., J Mol. Biol. 242, 309-320 (1994); Chothia and Lesk J. Mol Biol. 196:901-917 (1987), Chothia et al. Nature 342, 877-883 (1989), and/or or Al-Lazikani et al. J Mol Biol 273, 927-948 (1997).

As used herein, "PHOX2B" is defined as that sequence disclosed in Uniprot ID Q99453, shown below:

(SEQ ID NO: 2)

MYKMEYSYLNSSAYESCMAGMDTSSLASAYADFSSCSQASGFQYNPIRT

TFGATSGCPSLTPGSCSLGTLRDHQSSPYAAVPYKLFTDHGGLNEKRKQ

RRIRTTFTSAQLKELERVFAETHYPDIYTREELALKIDLTEARVQVWFQ

NRRAKFRKQERAAAAAAAAAKNGSSGKKSDSSRDDESKEAKSTDPDSTG

GPGPNPNPTPSCGANGGGGGGPSPAGAPGAAGPGGPGGEPGKGGAAAAA

AAAAAAAAAAAAAAAGGLAAAGGPGQGWAPGPGPITSIPDSLGGPFASV

LSSLQRPNGAKAALVKSSMF

The PHOX2B epitope that is targeted by the sequences claimed by the invention comprises residues 43-51 of Uniprot ID Q99453, and may be referred to hereafter as PHOX2B 43-51.

As used herein, "antigen-binding site" shall be taken to mean a structure formed by a protein that is capable of binding or specifically binding to an antigen, such as an antibody. The antigen-binding site need not be a series of contiguous amino acids, or even amino acids in a single polypeptide chain. For example, in a Fv comprising two different polypeptide chains from an antibody, the antigen-binding site is made up of a series of amino acids of a $V_L$ and a $V_H$ that interact with the antigen and that are generally, however not always in one or more of the CDRs in each variable region. In some embodiments, the antigen-binding site is an antigen-binding site of an antibody. In such embodiments, the antigen-binding site may comprise one or more complementarity-determining regions or "CDRs". In some embodiments, the antigen-binding site of an antibody comprises at least part of a $V_H$ or a $V_L$ or a Fv.

As used herein, the terms "complementarity-determining region" or "CDR" are used interchangeably to refer to the antigen binding regions found within the variable region of the heavy and light chain polypeptides. Generally, antibodies comprise three CDRs in each of the $V_H$ (CDR H1 or H1; CDR H2 or H2; and CDR H3 or H3) and three in each of the $V_L$ (CDR L1 or L1; CDR L2 or L2; and CDR L3 or L3).

As used herein, the "variable regions" and "CDRs" may refer to variable regions and CDRs defined by any approach known in the art, including combinations of approaches. According to a specific embodiment, the CDRs are determined according to Kabat et al. (supra).

As used herein "binding" or "binds" or "specifically binds" refers to an antibody:antigen mode of binding, which preferably, in the case of clinically relevant binding agents, means a $K_D$ below 1 μM or below 500 nM. The binding agents of the disclosure can bind PHOX2B:pMHC complexes with a high affinity. For example, in some embodiments the binding agent can bind PHOX2B:pMHC with a dissociation constant ($K_D$) equal to or less than about $10^{-6}$ M, such as $1\times10^{-6}$, $10^{-7}$, $10^{-8}$, $10^{-9}$, $10^{-10}$, $10^{-11}$, $10^{-12}$, $10^{-13}$ or $10^{-14}$. Specificity of binding is determined with reference to non-target proteins, such as for example bovine serum albumin (BSA). In some embodiments the binding agent binds PHOX2B:pMHC complexes with a dissociation constant ($K_D$) at least 2, 3, 4, 5, 10, 20, 50, 100, 200, 500, 1000, 2000, 5000, $10^4$, $10^5$ or $10^6$-fold lower than the binding agent's dissociation constant for BSA, when measured at physiological conditions. In some cases, specificity is determined by measuring binding of a binding agent to an MHC that is loaded with a non-target peptide or that is empty. In some cases, specificity is determined by measuring binding of a binding agent to the target peptide alone or the target peptide loaded on an MHC of a different allotype. In particular embodiments of the present disclosure, the binding agent is MHC-restricted which means that the binding agent binds specifically to a target peptide (e.g., PHOX2B peptide) loaded onto an MHC representative of a chosen allelic variant (e.g., HLA-A*24:02) with a dissociation constant ($K_D$) at least 2, 3, 4, 5, 10, 20, 50, 100, 200, 500, 1000, 2000, 5000, $10^4$, $10^5$ or $10^6$-fold lower than the binding agent's dissociation constant for an MHC from another allelic variant.

As used herein the phrase "chimeric antigen receptor (CAR)" refers to a recombinant or synthetic molecule which combines antibody-based specificity for a desired antigen with a T cell receptor-activating intracellular domain to generate a chimeric protein that exhibits cellular immune activity to the specific antigen.

As used herein the phrase "T Cell Receptor" or "TCR" refers to soluble and non-soluble forms of recombinant T-cell receptor As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell.

As used herein a "T Cell Receptor-like antibody" or "TCRL" refers to an antibody which binds an MHC displaying an HLA-restricted peptide antigen. Binding of the TCRL to its target typically has an MHC-restricted specificity: the TCRL does not bind the MHC in the absence of the complexed peptide, and the TCRL does not bind the peptide in an absence of the MHC. TCRLs are characterized by affinity sufficient to permit specific binding to a tumor antigen even when the TCRL is provided in a soluble, rather than membrane-bound, form. TCRLs are being developed as a new therapeutic class for targeting tumor cells and mediating their specific killing. In addition, TCRLs are valuable research reagents enabling the study of human class I peptide-MHC ligand presentation and TCR-peptide-MHC interactions. In an embodiment, the binding agent of the present disclosure is a TCRL.

As used herein the phrase "MHC (or HLA)-restricted peptide" refers to a peptide which is potentially presented on an MHC molecule. Such peptides may be identified by laboratory procedures such as Mass-Spectrometry, reverse-immunology or by in-silico analysis. An MHC (or HLA)-presented peptide refers to a peptide which is confirmed in vitro or in vivo as being presented by an MHC molecule.

The term "cancer" as used herein is defined as disease characterized by the rapid and uncontrolled growth of aberrant cells. Cancer cells can spread locally or through the bloodstream and lymphatic system to other parts of the body.

A "compound" refers to any molecule including small molecules, polypeptides, and other macromolecules. In some embodiments, a compound is a small molecular weight compound with a molecular weight of less than about 2000 Daltons.

The term "naturally-occurring" (or "native") as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical linker or a disulphide bond, for example. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The term "polynucleotide" as referred to herein means a polymeric form of nucleotides of at least 10 bases in length, either ribonucleotides or deoxynucleotides or a modified form of either type of nucleotide, or RNA-DNA heteroduplexes. The term includes single and double stranded forms of DNA.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis ($2^{nd}$ Edition, E. S. Golub and D. R. Gren, Eds., Sinauer Associates, Sunderland, Mass. (1991)).

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics.

The term "agent" is used herein to denote a chemical compound, a mixture of chemical compounds, a biological macromolecule, or an extract made from biological materials.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

The section headings used herein are for organizational purposes only and are not to be construed as limiting the subject matter described.

III. Binding Agents

The term "binding agent", as used herein, refers to any molecule which is capable of binding to the PHOX2B:HLA complex. In particular, the binding agent is capable of binding to a PHOX2B:HLA complex comprising the sequence QYNPIRTTF (SEQ ID NO: 1). In some embodiments, the binding agent is or comprises a polypeptide. In some embodiments, the binding agents of the present disclosure comprise the sequences provided and variants thereof. The disclosure specifically contemplates binding agents that have at least 75, 76, 77, 78, 79, 80, 81, 82, 83, 84, 85, 86, 87, 88, 89, 90, 91, 92, 93, 94, or 95% sequence identity or even at least 96, 97, 98, or 99% sequence identity to full length variable regions for constructs disclosed here, as long as the binding affinity to the PHOX2B:HLA complex is maintained. In some embodiments, the binding agents of the present disclosure further comprise dimeric binding agents derived by splitting the single chain variable fragment (scFv) sequences into light chain and heavy chain, respectively, at the poly-G/S linker, as well as homologs or variants of such dimeric binding agents. Optionally, specificity or affinity of binding to the PHOX2B:HLA complex is maintained or even improved. In particular embodiments, the binding agent comprises a heavy chain and a light chain which comprises three heavy chain CDR and three light chain CDR sequences, respectively, of the present disclosure, maintaining or improving binding. In embodiments of the disclosure, the binding agent is an antibody, or antigen-binding fragment thereof, an artificial protein that is soluble (e.g., a bispecific antibody), or an artificial protein that is membrane-tethered (e.g., a chimeric antibody receptor or a TCR fusion protein).

For binding agents derived from immunoglobulin (Ig) variable domains, with the target contact surface created through the loops connecting β-strands (the complementarity-determining regions, or CDRs), the binding activity to the target may be transferable through the grafting of the CDR loops to related Ig domains (e.g., other human Ig family members) or even non-Ig β-sheet scaffolds. This is especially the case where the structure of the binding agent in complex with the target indicates that the binding is mainly contributed through one, or a few, of the 6 CDRs of the combined $V_L$ and $V_H$ domains. The disclosure specifically contemplates binding agents that have at least 50, 55, 60, 65, 70, 75, 80, 85, 90 or 95% sequence identity to single CDR regions for constructs disclosed here, as long as the binding affinity to the PHOX2B:HLA complex is functionally maintained. CDR grafting has been used extensively to 'humanize' antibodies where the CDR loops from antibodies derived from a non-human host are grafted onto a human Ig scaffold to reduce immunogenicity. Many antibodies approved for therapeutic use have been humanized through CDR transplantation from murine antibodies onto human scaffolds. Examples where the grafting of CDR loops from antibody scaffolds onto non-Ig alternative scaffolds have also been reported (Nicaise M., et al. Protein Sci 13:1882-1891 (2004); Petrovskaya L E, et al. Biochemistry (Mosc) 77:62-70 (2012); Pacheco et al. Protein Eng Des Sel 27:431-438 (2014)).

Various means of determining the $K_D$ of a binding agent for its target are known, including enzyme-linked immunoabsorbance (ELISA) assays and Surface Plasmon Resonance (SPR) assays. In some cases binding affinity and specificity is determined by optical interferometry, such as with the Pall ForteBio BLItz® system, as described in Sultana A. Lee J. Curr Protoc Protein Sci, 79:19.25.1-19.25.26 (2015). Affinity of a binding agent may be determined using a soluble form of the binding agent or a membrane-tethered form, such as a chimeric antigen receptor (CAR) or T-cell receptor (TCR) fusion protein (TFP). Conversely, the pMHC complex may be tested in a soluble form or in its native, cell-membrane-bound state.

A. Antibodies

In some embodiments, the binding agent is an antibody or antibody fragment. Suitable antibody fragments for practicing some embodiments of the disclosure include between one and three complementarity-determining region (CDRs) of an immunoglobulin light chain (referred to herein as "light chain") and between one and three CDRs of an immunoglobulin heavy chain (referred to herein as "heavy chain"). Optionally, the binding agent comprises a variable region of a light chain, a variable region of a heavy chain, a light chain, or a heavy chain.

The identity of the amino acid residues in a particular antibody that make up a variable region or a CDR can be determined using methods well known in the art and include methods such as sequence variability as defined by Kabat et al. (See, e.g., Kabat et al., 1992 Sequences of Proteins of Immunological Interest, 5th ed., Public Health Service, NIH, Washington D.C), location of the structural loop regions as defined by Chothia et al. (see, e.g., Chothia et al., Nature 342:877-883 (1989), a compromise between Kabat and Chothia using Oxford Molecular's AbM antibody modeling software (now Accelrys®, see, Martin et al. Proc Natl Acad Sci USA. 86:9268 (1989); and world wide web site world-wide-web at bioinf-org.uk/abs), available complex crystal structures as defined by the contact definition (see MacCallum et al. J. Mol. Biol. 262:732-745 (1996)), the "conformational definition" (see, e.g., Makabe et al., Journal of Biological Chemistry, 283:1156-1166 (2008)), and the IMGT method (Lefranc M P, et al. IMGT unique numbering for immunoglobulin and T cell receptor variable domains and Ig superfamily V-like domains Dev Comp Immunol 27: 55-77 (2003)).

In embodiments, the binding agent is a functional antibody fragment comprising whole or essentially whole variable regions of both light and heavy chain, including but not limited to those defined as follows: (i) Fv, defined as a fragment consisting of the variable region of the light chain (VL) and the variable region of the heavy chain (VH) expressed as two chains; (ii) single chain variable fragment or single chain Fv ("scFv"), a genetically engineered single chain molecule including the variable region of the light chain and the variable region of the heavy chain, linked by a suitable polypeptide linker as a genetically fused single chain molecule; (iii) disulfide-stabilized Fv ("dsFv"), a genetically engineered antibody including the variable region of the light chain and the variable region of the heavy chain, linked by a genetically engineered disulfide bond; (iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CHI domains thereof; (v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule); (vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) single domain antibodies or nanobodies are composed of a single $V_H$ or $V_L$ domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988).

Antibody fragments according to some embodiments of the disclosure can be prepared by proteolytic hydrolysis of the antibody or by expression in *E. coli* or mammalian cells (e.g., Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. See also Porter, R. R., Biochem J. 73:119-126 (1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

In an embodiment in which the binding agent is an antibody, the heavy and light chains of an antibody of the disclosure may be full-length (e.g., an antibody can include at least one, and preferably two, complete heavy chains, and at least one, or two, complete light chains). In some embodiments, the antibody heavy chain constant region is chosen from, e.g., IgG1, IgG2, IgG3, IgG4, IgM, IgA1, IgA2, IgD, and IgE. In some embodiments, the immunoglobulin isotype is selected from IgG1, IgG2, IgG3, and IgG4, more particularly, IgG1 (e.g., human IgG1) or IgG4 (e.g., human IgG4). The choice of antibody type will depend on the immune effector function that the antibody is designed to elicit. In an embodiment, the binding agent elicits antibody dependent cellular cytotoxicity. In an embodiment, the binding agent elicits complement dependent cytotoxicity.

Bispecific configurations of antibodies are also contemplated herein. A bispecific monoclonal antibody (BsMAb, BsAb) is an artificial protein, or complex of proteins, that is composed of fragments of two different monoclonal antibodies and consequently binds to two different types of antigen. According to a specific embodiment the BsMAb is engineered to simultaneously bind to an effector cell (e.g., using a receptor like CD3) and a target like a tumor cell to be destroyed. Anti-CD3 antibodies known to the art and used for directing bispecific antibody engagement with CD3-positive effector cells include SP-34 (Pessano et al., EMBO J (1985) 4:337-344), OKT3 (Kung et al., Science (1979) 206: 347-349), UCHT1 (Beverley PCL, Callard R E Eur J Immunol (1981) 11:329), 12F6 (Wong J T and Colvin R B, J Immunol (1987) 139:1369-1374), and humanized and/or affinity engineered variants of all (e.g. Shalaby et al., J Exp Med (1992) 175:217-225). Other affinity scaffolds, such as VHH domains, may also be used to engineer CD3 binding (e.g. WO/2015/095412). Other configurations, such as tri-specific or tetra-specific antibodies, for example, are also contemplated.

B. Single-Chain Variable Fragment (scFv)

Fv fragments comprise an association of $V_H$ and $V_L$ chains. This association may be noncovalent, as described in Inbar et al. Proc Natl Acad. Sci. USA 69:2659-62 (1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are described, for example, by Whitlow and Filpula, Methods 2:97-105 (1991); Bird et al., Science 242:423-426 (1988); Pack et al., Bio/Technology 11:1271-77 (1993); and U.S. Pat. No. 4,946,778. The resulting polypeptides can fold back on themselves to form antigen-binding monomers, or they can form multimers (e.g., dimers, trimers, or tetramers), depending on the length of a flexible linker between the two variable domains (Kortt et al., Prot Eng 10:423 (1997); Kortt et al, Biomol Eng 18:95-108 (2001)). By combining different $V_L$ and $V_H$-comprising polypeptides, one can form multimeric scFvs that bind to different epitopes (Kriangkum et al., (2001) Biomol. Eng. 18:31-40). Techniques developed for the production of single chain antibodies include those described in U.S. Pat. No. 4,946,778; Bird, Science 242:423 (1988); Huston et al. Proc Natl Acad Sci USA 85:5879 (1988); Ward et al. Nature 334:544 (1989), de Graaf et al. Methods Mol Biol. 178:379-87 (2002). Single chain antibodies derived from binding provided herein include, but are not limited to, scFvs comprising one or more variable domain sequences, or one or more CDR sequences from one or more variable domain sequences, disclosed herein.

C. Chimeric Antigen Receptor (CAR) and TCR Fusion Proteins (TFP)

Chimeric antigen receptors (CARs) are fusion proteins comprising antigen recognition moieties and T cell-activation domains. Exemplary CARs are provided by U.S. Pat. Nos. 8,399,645 and 7,638,325. Other exemplary recombinant receptors, including CARs, recombinant T-cell receptors (TCRs), TCR fusion proteins (TFPs), as well as methods for engineering and introducing the receptors into cells, include those described in Int'l Pat. Appl. Nos. WO2017/096329, WO2000/14257, WO2013/126726, WO2012/129514, WO2014031687, WO2013/166321, and WO2013/071154, WO2013/123061, and WO/2014055668; U.S. Pat. App. Nos. US2002131960, US2013287748, and US20130149337; U.S. Pat. Nos. 6,451,995, 7,446,190, 7,638,325, 8,252,592, 8,339,645, 8,398,282, 7,446,179, 6,410,319, 7,070,995, 7,265,209, 7,354,762, 7,446,191, 8,324,353, and 8,479,118; European Pat. App. No. EP2537416; and Sadelain et al. Cancer Discov. April 3(4): 388-398 (2013); Davila et al. PLoS ONE 8(4): e61338 (2013); Turtle et al. Curr. Opin. Immunol. October 24(5): 633-39 (2012); and Wu et al. Cancer, March 18(2): 160-75 (2012). In an embodiment, the binding agent is a TFP as described in U.S. patent Ser. No. 15/419,398.

D. Amino Acid Substitutions

As discussed herein, minor variations in the amino acid sequences of the binding agents are contemplated as being encompassed by the present disclosure, providing that the variations in the amino acid sequence maintain at least 75%, more preferably at least 80%, 90%, 95%, and most preferably 99% sequence identity to the variable domains, or at least 50, 55, 60, 65, 70, 75, 80, 85, 90 or 95% sequence identity to single CDR regions for constructs disclosed here, so long as the binding affinity to the PHOX2B:HLA complex is functionally maintained. For example, the binding agent may comprise one or more amino acid substitutions relative to a CDR sequence provided herein. The binding agents may also comprise one or more amino acid substitutions in a framework region. In some embodiments, the binding agent may have no more than 2 amino acid substitutions in the CDR-L1, no more than 2 amino acid substitutions in the CDR-L2, no more than 3 amino acid substitutions in the CDR-L3, no more than 2 amino acid substitutions in the CDR-H1, no more than 2 amino acid substitutions in the CDR-H2, or no more than 4 amino acid substitutions in the CDR-H3, relative to any one or more of the CDR amino acid sequences provided herein. In some embodiments, the binding agent comprises an amino acid substitution in a framework region. For example, as a person skilled in the art would appreciate, routine site-directed or random mutagenesis techniques can be performed to alter the amino acid sequence of any one of the binding agents described herein in order to, for example, alter binding affinity (e.g., affinity maturation), reduce susceptibility to proteolysis or oxidation, or confer or modify other physicochemical or functional properties of the binding agents.

In some embodiments, the amino acid substitutions are conservative amino acid substitutions. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More particular families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Examples of conservative amino acid substitutions are provided below in Table 1.

TABLE 1

Exemplary conservative amino acid changes

| Original amino acid | Exemplary substitutions | Preferred substitutions |
|---|---|---|
| Ala | Val; Leu; Ile | Val |
| Arg | Lys; Gln; Asn | Lys |
| Asn | Gln; His; Asp, Lys; Arg | Gln |
| Asp | Glu; Asn | Glu |

TABLE 1-continued

| Exemplary conservative amino acid changes | | |
|---|---|---|
| Original amino acid | Exemplary substitutions | Preferred substitutions |
| Cys | Ser; Ala | Ser |
| Gln | Asn; Glu | Asn |
| Glu | Asp; Gln | Asp |
| Gly | Ala | Ala |
| His | Asn; Gln; Lys; Arg | Arg |
| Ile | Leu; Val; Met; Ala; Phe; Norleucine | Leu |
| Leu | Norleucine; Ile; Val; Met; Ala; Phe | Ile |
| Lys | Arg; Gln; Asn | Arg |
| Met | Leu; Phe; Ile | Leu |
| Phe | Trp; Leu; Val; Ile; Ala; Tyr | Tyr |
| Pro | Ala | Ala |
| Ser | Thr | Thr |
| Thr | Val; Ser | Ser |
| Trp | Tyr; Phe | Tyr |
| Tyr | Trp; Phe; Thr; Ser | Phe |
| Val | Ile; Leu; Met; Phe; Ala; Norleucine | Leu |

The present disclosure also contemplates non-conservative amino acid substitutions in a binding agent of the disclosure, provided that the binding agent is still capable of specifically binding to an HLA-A*24:02/PHOX2B complex, an HLA-A*23:01/PHOX2B complex or an HLA-B*14:02/PHOX2B complex. Thus, in some embodiments, the amino acid substitutions are non-conservative amino acid substitutions.

Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Particular amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known, such as Bowie et al., Science 253:164 (1991) or[86]. Thus, the foregoing examples demonstrate that those of skill in the art can recognize sequence motifs and structural conformations that may be used to define structural and functional domains in accordance with the antibodies described herein.

Particular amino acid substitutions are those which: (1) reduce susceptibility to proteolysis, (2) reduce susceptibility to oxidation, (3) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991); and Thornton et al. Nature 354:105 (1991).

Routine techniques can be used to introduce amino acid substitutions in CDRs to, for example, improve binding affinity. Such substitutions may be made in CDR "hotspots," i.e., residues encoded by codons that undergo mutation at high frequency during the somatic maturation process (see, e.g., Chowdhury, Methods Mol. Biol. 207:179-196 (2008)), and/or residues that contact the antigen, with the resulting variant being tested for binding affinity. Alternatively, or additionally, affinity maturation may be performed. Affinity maturation by constructing and reselecting from secondary libraries has been described, e.g., in Hoogenboom et al., Methods in Molecular Biology 178:1-37 (O'Brien et al., ed., Human Press, Totowa, NJ, (2001)). In some embodiments of affinity maturation, diversity is introduced into the variable region coding sequences chosen for maturation by any of a variety of methods (e.g., error-prone PCR, chain shuffling, or oligonucleotide-directed mutagenesis). A secondary library is then created. The library is then screened to identify any variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis, described below, or modelling. CDR-H3 and CDR-L3 in particular can be used for random mutagenesis and affinity maturation.

In certain embodiments, substitutions, insertions, or deletions may occur within one or more CDRs so long as such alterations do not substantially reduce the ability of the binding agent to bind an HLA-A*24:02/PHOX2B complex, an HLA-A*23:01/PHOX2B complex or an HLA-B*14:02/PHOX2B complex. In some embodiments, the binding agent comprising the amino acid substitutions binds to an HLA-A*24:02/PHOX2B complex, an HLA-A*23:01/PHOX2B complex or an HLA-A*24:02/PHOX2B complex, an HLA-A*23:01/PHOX2B complex or an HLA-B*14:02/PHOX2B complex with a similar affinity to the binding agent without the substitutions. Such substitutions may, for example, be outside of antigen-contacting residues in the CDRs. In some embodiments, the binding agent comprising the amino acid substitutions binds to an HLA-A*24:02/PHOX2B complex, an HLA-A*23:01/PHOX2B complex or an HLA-B*14:02/PHOX2B complex with a higher affinity than the binding agent without the substitutions. In some embodiments, the binding agent comprising the amino acid substitutions binds to an HLA-A*24:02/PHOX2B complex, an HLA-A*23:01/PHOX2B complex or an HLA-B*14:02/PHOX2B complex with a lower affinity than the binding agent without the substitutions. In certain embodiments, each CDR either is unaltered, or contains no more than one, two, three, or four amino acid substitutions. In some embodiments, the substitutions are conservative substitutions.

A useful method for identification of residues or regions of a binding agent that may be targeted for mutagenesis is called "alanine scanning mutagenesis" as described by Cunningham, Science 244:1081-1085 (1989). In this method, a residue or group of target residues (e.g., charged residues such as Arg, Asp, His, Lys, and Glu) are identified and replaced by a neutral amino acid such as alanine to determine whether the interaction of the binding agent with its antigen is affected. Further substitutions may be introduced at the amino acid locations demonstrating functional sensitivity to the initial substitutions. Alternatively, or additionally, a crystal structure of an antigen-binding agent complex can be used to identify contact points between the binding agent and antigen. Such contact residues and neighbouring residues may be targeted or eliminated as candidates for substitution. Variants may be screened to determine whether they contain the desired properties.

IV. Nucleic Acids

According to an aspect of the disclosure there is also provided an isolated polynucleotide comprising a nucleic acid sequence encoding the binding agent as described herein. Also provided is an expression vector, comprising the polynucleotide operably linked to a cis-acting regulatory element. The expression vector of some embodiments of the disclosure includes additional sequences which render this vector suitable for replication and integration in prokaryotes, eukaryotes, or preferably both (e.g., as a shuttle vector). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the disclosure includes a signal sequence for secretion or presentation of the binding agent from a host cell in which it is placed. Preferably the signal sequence for this purpose is a mammalian signal sequence.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated. Preferably, the promoter utilized by the expression vector is active in the specific cell population transformed. Examples of cell type-specific and/or tissue-specific promoters include promoters such as albumin that is liver specific (Pinkert et al. Genes Dev. 1:268-277 (1987)), lymphoid specific promoters (Calame et al. Adv. Immunol. 43:235-275 (1988)); in particular promoters of T-cell receptors (Winoto et al. EMBO J. 8:729-733 (1989)) and immunoglobulins; (Banerji et al. Cell 33:729-740 (1983)), neuron-specific promoters such as the neurofilament promoter (Byrne et al. Proc. Natl. Acad. Sci. USA 86:5473-5477 (1989)), pancreas-specific promoters (Edlunch et al. Science 230:912-916 (1985)) or mammary gland-specific promoters such as the milk whey promoter (U.S. Pat. No. 4,873,316 and European Application Publication No. EP0264166). In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the disclosure include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983.

Polyadenylation sequences can also be added to the expression vector in order to increase the efficiency of TCRL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the disclosure include those derived from SV40.

In addition to the elements already described the expression vector of some embodiments of the disclosure may contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Also provided are cells which comprise the polynucleotides/expression vectors as described herein. Such cells are typically selected for high expression of recombinant proteins (e.g., bacterial, plant or eukaryotic cells e.g., CHO, HEK-293 cells), but may also be host cells having a specific immune effector activity (e.g., T cells or NK cells) when for instance the CDRs of the TCRL are implanted in a T Cell Receptor or CAR transduced in said cells which are used in adoptive cell therapy.

V. Diagnostic Applications

The high specificity of the binding agent renders it particularly suitable for diagnostic and therapeutic applications. According to an aspect of the present disclosure, there is provided a method of detecting a cell presenting an HLA-restricted peptide antigen of interest. The method comprises contacting the cell with the binding agent (e.g., antibody) of the present disclosure having specificity to the HLA-restricted peptide antigen of interest. The contacting is effected under conditions which allow immunocomplex formation, wherein a presence of the immunocomplex or the level thereof is indicative of the cell presenting the HLA-restricted peptide antigen of interest.

The term "detecting," as used herein, refers to the act of detecting, perceiving, uncovering, exposing, visualizing or identifying a cell. The precise method of detecting is dependent on the detectable moiety to which the antibody is attached.

Single cells may be used for detection as well as a plurality of cells. For instance the cells may be from any biological sample such as cell lines, primary cells (e.g., tumor cultures), and cellular samples (e.g., surgical biopsies including incisional or excisional biopsy, fine needle aspirates and the like). Methods of biopsy retrieval are well known in the art. The above-mentioned detection method can be harnessed to the diagnosis of diseases (such as cancer) which are characterized by above normal presentation or different tissue distribution of the HLA-peptide complex.

As used herein the term "diagnosing" refers to classifying a disease, determining a severity of a disease (grade or stage), monitoring progression, forecasting an outcome of the disease and/or prospects of recovery.

The subject may be a healthy subject (e.g., human) undergoing a routine well-being check-up. Alternatively, the subject may be at risk of the disease. The method may be used to monitor treatment efficacy. The binding agent may comprise, that is, be attached to, a detectable moiety. Alternatively or additionally, the binding agent (or a complex comprising same) may be identified indirectly such as by using a secondary antibody. The contacting may be effected in vitro (i.e., in a cell line, primary cells), ex vivo, or in vivo.

VI. Pharmaceutical Compositions, Formulations and Dosages

Pharmaceutical compositions according to the present disclosure, and for use in accordance with the present disclosure, may comprise, in addition to the active ingredient, (i.e., the binding agent), a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, or by injection, e.g., cutaneous, subcutaneous, or intravenous.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

In one embodiment, the composition is a pharmaceutical composition (e.g., formulation, preparation, medicament) comprising a binding agent, as described herein, and a pharmaceutically acceptable carrier, diluent, or excipient.

In one embodiment, the composition is a pharmaceutical composition comprising at least one binding agent, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilizers, solubilizers, surfactants (e.g., wetting agents), masking agents, coloring agents, flavoring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash) Synapse Information Resources, Inc., Endicott, New York, USA (2001), Remington's Pharmaceutical Sciences, 20th edition, pub. Lippincott, Williams & Wilkins, (2000); and Handbook of Pharmaceutical Excipients, 2nd edition (1994).

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

It will be appreciated by one of skill in the art that appropriate dosages of the binding agent, and compositions comprising the binding agent, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of binding agent and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In some embodiments, the binding agent or composition containing the same is administered once per week for a therapeutically effective period of time. In some embodiments, the binding agent or composition containing the same is administered once per day for a therapeutically effective period of time. In some embodiments, the binding agent or composition containing the same is administered once per month for a therapeutically effective period of time. In some embodiments, the binding agent or composition containing the same is administered once per year for a therapeutically effective period of time.

In general, a suitable dose of the binding agent is in the range of about 100 ng to about 25 mg (more typically about 1 μg to about 10 mg) per kilogram body weight of the subject per day. Where the composition comprises a salt, an ester, an amide, a prodrug, or the like, the amount administered is calculated on the basis of the parent compound and so the actual weight to be used is increased proportionately.

VII. Treatment

The binding agents of the disclosure (e.g., antibodies, CARs) are especially useful for the treatment of cancer. In particular embodiments, the cancer is characterized by expression of PHOX2B. Types of cancers to be treated with the binding agents of the disclosure include, but are not limited to, hematological cancers, solid tumors, and non-solid tumors. Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma and brain metastases). Adult tumors/cancers and pediatric tumors/cancers are also included.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as aprophylactic measure (i.e., prophylaxis, prevention) is also included.

The term "therapeutically-effective amount," as used herein, pertains to that amount of binding agent, or a material such as an antibody-drug conjugate, composition or dosage form comprising an active binding agent, which is effective for producing some desired therapeutic effect when administered in accordance with a desired treatment regimen.

In some embodiments, the treatment reduces or inhibits tumor growth for at least 6, 12, 24, 36, or 48 months. In some embodiments, the treatment enhances an immune response against the tumor.

The subject/patient may be an animal or any species of mammal, including, without limitation, a horse, a dog, a cat, a pig, or a primate. In a particular embodiment, the subject/patient is a human.

VIII. Examples

The following examples are included to demonstrate particular embodiments. It should be appreciated by those of skill in the art that the techniques disclosed in the examples that follow represent techniques discovered by the inventor to function well in the practice of embodiments, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

ReD library panning. The Ruby scFv library (>$10^{11}$ diversity) was constructed using human germline IGLV1-51, IGLV3-1 and IGLV6-57 scaffolds paired with the IGHV3-23 scaffold, as described by Beasley et al.[56], with fully synthetic amino acid diversity in both $V_L$ and $V_H$ CDR3 loops.

The Ruby scFv library, and its combination and use with the Retained Display platform for antibody screening, are described by WO/2011/075761 (Protein display), WO/2013/023251 (Soluble polypeptides), and WO/2013/000023 (Method of Protein display).

The Ruby library was panned for two rounds using PHOX2B (43-51) A*24:02 MHC complex bound to MyOne Streptavidin C1 Dynabeads (ThermoFisher, Cat: 65002). Panned library output were transferred into the ReD cell-display platform[56] and cells were permeabilized using 0.5% n-octyl β-d-thioglucopyranoside (Anatrace, Cat: 0314) and labeled using recombinant PHOX2B pMHC complex ligated to fluorophores excitable by 405 nm and 488 nm lasers. Cells that were positive for target binding were isolated using the FACSMelody sorter (Becton-Dickinson).

After two rounds of positive selection for binding to PHOX2B A*24:02 MHC complex two further FACS rounds were conducted using counter-labelled A*24:02 MHC complexes with unrelated peptides. After four rounds of FACS individual colonies were picked and grown in 96-well plates before scFv induction, cell permeabilization, and PHOX2B MHC labelling and detection by CytoFLEX (Beckman Coulter).

Clones that were identified as binding specifically to the PHOX2B (43-51) MHC complex were sequenced and unique scFvs were expressed as fusions to the AviTag™ biotinylation motif in *E. coli*. Biotinylated scFv protein was released via permeabilization with 0.5% n-octyl β-d-thio-glucopyranoside and purified to ~90% purity on Nickel NTA agarose resin (ABT, Cat: 6BCL-NTANi).

Binding kinetics. Affinity measurements were performed using a BLItz™ system (ForteBio, USA) and analyzed using the BLItz Pro™ software. Streptavidin biosensors (ForteBio, Cat: 18-5019) were loaded with AviTag™-biotinylated scFv, blocked with biotin, washed in PBS, and then associated with pMHC ligand in PBS.

Steady-state binding assay. An equilibrium binding assay to target pMHCs was also established using MyOne Streptavidin C1 Dynabeads. Briefly, 50 micrograms of Streptavidin C1 Dynabeads were incubated with excess biotinylated scFv before being blocked with free biotin and washed in PBS. Fluorophore-labelled pMHC complex was added to a concentration of 3.5 nM and incubated for 1 hour at 4° C. followed by 10 minutes at 25° C. Binding of the free MHC complex to the beads was quantitated by the CytoFLEX at 488 nm (ex)/525 nm (em). Binding was normalized to beads without scFv and with unrelated control MHC complex.

This bead-binding assay was used to quantitate the binding of scFv to MHC complexes with alanine-scan substitutions of the PHOX2B peptides as well as to a plate of 95 unrelated 9-mer peptide A*24:02 MHC complexes and the degree of cross-reactivity of binding of MHC complexes with peptides identified as having high homology to the PHOX2B peptide by eXpitope 2.0.

Viral production and transduction of Jurkat and primary T cells. Retrovirus for transduction of Jurkats and primary CD4/8 T cells was produced using Platinum-A (Plat-A) cells, a retroviral packaging cell line. Cells were plated in 6-well plates at $7\times10^5$ cells/well and transfected with 2.5 μg of the appropriate TCR or CAR construct in the retroviral vector pMP71 using Lipofectamine 3000 (Life Technologies, Invitrogen). After 24 hours, medium was replaced with IMDM-10% FBS or AIM-V-10% FBS for Jurkat cells or primary cells, respectively. Supernatants were harvested and filtered with 0.2 mM filters after 24 hours incubation.

A second-generation lentiviral system was used to produce replication-deficient lentivirus. The day preceding transfection, 15 million HEK 293T cells were plated in a 15-cm dish. On the day of transfection, 80 μL Lipofectamine 3000 (Life Technologies, Invitrogen) was added to 3.5 mL room-temperature Opti-MEM medium (Gibco). Concurrently, 80 μL P3000 reagent (Thermo Fisher Scientific), 12 μg psPAX2 (Gag/Pol), 6.5 μg pMD2.6 (VSV-G envelope), and a matching molar quantity of transfer plasmid were added to 3.5 mL room-temperature Opti-MEM medium. Virus supernatant was collected after 24 and 48 hours later and briefly centrifuged at 300 g and passed through a 0.45 μM syringe.

Jurkat cells were plated in 6-well plates pre-treated with 1 mL well/Retronectin (20 mg/mL, Takara Bio. Inc.) at $1\times10^6$ cells/well and spinoculated with 2 mL of retroviral supernatant at 800×g for 30 min at RT. After 24 hours, cells were harvested, and grown in IMDM-10% FBS.

Primary T cells were thawed and activated in culture for 3 days in the presence of 100 U/ml IL-2 and anti-CD3/CD28 beads (Dynabeads, Human T-Activator CD3/CD28, Life Technologies) at a 3:1 bead:T cell ratio. On days 4 and 5, activated cells were plated in 6-well plates pre-treated with 1 mL well/Retronectin (20 mg/mL, Takara Bio. Inc.) at $1\times10^6$ cells/well and spinoculated with 2 mL of retroviral supernatant at 2400 rpm for 2 hours at 32° C. On day 6, cells were harvested and washed, beads were magnetically removed, and cells were expanded in AIM-V-10% FBS supplemented with 25 U/ml IL-2.

Primary human T cells were thawed and activated in culture for 1 day in the presence of 5 ng/ml recombinant IL-7, 5 ng/ml recombinant IL-15, and anti-CD3/CD28 beads (Dynabeads, Human T-Activator CD3/CD28, Life Technologies) at a 3:1 bead:T cell ratio in G-Rex system vessels (Wilson Wolf). On day 2, thawed lentiviral vector was added to cultured T cells with 10 μg/mL Polybrene (Millipore Sigma), and 24 hours later vessels were filled with complete AIM-V medium supplemented with indicated concentrations of IL-7 and IL-15. On day 10, cells were harvested and washed. Activation beads were magnetically removed, and cell viability was determined before freezing.

Human neuroblastoma cell lines were plated in 6-cm dishes, and 2 mL of thawed lentiviral vector produced with transfer plasmid pLenti-CMV-eGFP-Puro (Addgene plasmid #17448) was added with 10 μg/mL Polybrene (Millipore Sigma). Cells were selected for eGFP expression using flow-assisted cell sorting (BD FACSJazz, BD Biosciences) followed by 10 μg/mL puromycin selection.

Selective Cross-Reactive Antigen Presentation (sCRAP) prediction. Tumor antigens were compared against the entire normal human proteome on the matched HLA (85,915,364 total normal peptides among HLA 84 HLAs). Each residue in the same position of the tumor and human peptides was assigned a score for perfect match, similar amino acid classification, or different polarity, scoring five, two, or negative two respectively. Similarity scores were calculated based on amino acid classification and hydrophobicity was determined using residues one and three through eight and excluding MHC anchor residues. Next, the maximum normal tissue RPKM values were identified from 1643 normal tissues in GTEx. Normal peptides were compared to a database of normal tissue immunopeptidomes[67]. The overall cross-reactivity score for each normal peptide was then calculated using the following equation:

$$\frac{\sum_{i=3}^{n} Pi}{b * E\max}$$

where n is the peptide length, P is the score of each amino acid of the normal peptide as compared to the tumor antigen, b is the pMHC binding affinity of the normal peptide, and $E_{max}$ is the maximum normal tissue expression The algorithm is available at marisshiny.research.chop.edu/sCRAP.

Tetramer/dextramer staining and flow cytometric analysis. Surface expression and binding of CAR-transduced Jurkat cells and primary T cells was measured by staining with PE- or APC-conjugated dextramers carrying NB antigen peptide-MHC (Immudex). Cells were harvested from culture, washed with 2 ml PBS at 800×g for 5 min, incubated with 1 μl dextramer for 10 min in the dark, washed again, and resuspended in 300 ul PBS for analysis. Typically, $5\times10^5$ cells were used for staining, and analyzed on a BD LSR II (BD Biosciences) or an Attune Acoustic Focusing Cytometer (Applied Biosystems, Life Technologies).

Cross-reactivity pMHC screen. Potential cross-reactive peptides (GenScript) were suspended at a 200 μM working concentration. For each test, 0.5 μL of peptide was added to 5 μL HLA-A*24:02 empty loadable tetramer (Tetramer Shop) before incubating on ice for 30 minutes, or using TAPBR peptide exchange as previously described[68]. Following preparation, pMHC tetramers were used to stain cells (described above).

Incucyte Cytotoxicity Assay. $0.5\times10^5$ tumor cell targets were co-incubated with varying ratios of transduced primary cells ($5\times10^5$, $2.5\times10^5$, $1\times10^5$, $0.5\times10^5$, and $2.5\times10^4$ for 10:1, 5:1, 2:1, 1:1, and 1:2 effector:target (E:T) ratios, respectively) in 96-well plates at 37° C. in the presence of 0.05 μM caspase-3/7 red (Incucyte, Essence BioScience). Plates ran on the Incucyte for 24-72 hours and measured for apoptosis activity via caspase cleavage and comparison of relative confluency. Following the assay, supernatants were collected for ELISA. Total GFP integrated intensity (Total GCU×$\mu m^2$/Image) was assessed as a quantitative measure of live, GFP+ tumor cells. Values were normalized to the t=0 measurement.

Cytokine Secretion Assays. Cell supernatant collected from cell cytotoxicity assays was thawed and plated in triplicate for each condition. IFN-γ and IL-2 levels were determined using ELISA kits according to the manufacturer's protocol (BioLegend).

Expression, refolding, and purification of recombinant peptide/HLA molecules. HLA-A*02:01 and HLA-A*24:02 constructs for bacterial expression were cloned into pET24a+ plasmid. DNA plasmids encoding HLA-A*02:01 (heavy chain), HLA-A*24:02 (heavy chain), and human β2M (light chain) were transformed into *E. coli* BL21-DE3 (Novagen), expressed as inclusion bodies and refolded using previously described methods[71]. *E. coli* cells were grown in autoinduction media for (16-18 hours)[72]. Afterward, the *E. coli* cells were harvested by centrifugation and resuspended with 25 mL BugBuster (Milipore Sigma) per liters of culture. The cell lysate was sonicated and subsequently pelleted by centrifugation (5,180×g for 20 minutes at 4° C.) to collect inclusion bodies. The inclusion bodies were washed with 25 mL of wash buffer (100 mM Tris pH 8.0, 2 mM EDTA, and 0.01% v/v deoxycholate), sonicated, and pelleted by centrifugation. A second wash was done using 25 mL of Tris-EDTA buffer (100 mM Tris pH 8.0 and 2 mM EDTA). The solution was once again resuspended by sonication then centrifuged. The inclusion bodies were then solubilized by resuspension with 6 mL of resuspension buffer (100 mM Tris pH 8.0, 2 mM EDTA, 0.1 mM DTT, and 6 M guanidine-HCl). Solubilized inclusion bodies of the heavy and light chain were mixed in a 1:3 molar ratio and then added dropwise over 2 days to 1 L of refolding buffer (100 mM Tris pH 8.0, 2 mM EDTA, 0.4 M arginine-HCl, 4.9 mM L-glutathione reduced, and 0.57 mM L-glutathione oxidized) containing 10 mg of synthetic peptide at >98% purity confirmed by mass-spec (Genscript). Refolding was allowed to proceed for 4 days at 4° C. without stirring. Following this incubation period, the refolding mixture was dialyzed into the size-exclusion buffer (25 mM Tris pH 8.0 and 150 mM NaCl). After dialysis, the sample was concentrated first using a Labscale Tangential Flow Filtration system and then using an Amicon Ultra-15 Centrifugal 10 kDa MWCO Filter Unit (Millipore Sigma), to a final volume of 5 mL. Purification was performed using size-exclusion chromatography on a HiLoad 16/600 Superdex 75 column. After size-exclusion, the sample was further purified by anion exchange chromatography using a MonoQ 5/50 GL column and a 0-100% gradient of buffer A (25 mM Tris pH 8.0 and 50 mM NaCl) and buffer B (25 mM Tris pH 8.0 and 1 M NaCl). The purified protein was exhaustively exchanged into 20 mM sodium phosphate pH 7.2 and 50 mM NaCl. The final sample was validated using SDS-PAGE to confirm the formation of a pMHC complex containing both the heavy and light chains.

Immunohistochemistry. CD3 (Dako A0452), PHOX2B (Abcam ab183741), and HLA-ABC (Abcam ab70328) antibodies were used to stain formalin fixed paraffin embedded tissue slides. Staining was performed on a Bond Max automated staining system (Leica Biosystems). The Bond Refine polymer staining kit (Leica Biosystems, DS9800) was used. The standard protocol was followed with the exception of the primary antibody incubation which was extended to 1 hour at room temperature. CD3, PHOX2B, and HLA-ABC antibodies were at 1:100, 1:500, and 1:1200 dilutions respectively. Antigen retrieval was performed with E1 (Leica Biosystems) retrieval solution for 20 min (E2 for PHOX2B). Slides were rinsed, dehydrated through a series of ascending concentrations of ethanol and xylene, then coverslipped. Stained slides were then digitally scanned at 20× magnification on an Aperio CS-O slide scanner (Leica Biosystems).

Murine PC-CAR T cell preclinical trials. NOD SCID Gamma (NSG) female (6-8 weeks of age) mice from Jackson Laboratories (stock number 005557) were used to propagate subcutaneous xenografts. All mice were maintained under barrier conditions and experiments were conducted using protocols and conditions the IACUC at the Children's Hospital of Philadelphia. Treatment was initiated via lateral tail intravenous injection. Dose administered was 100 ul per animal of vehicle or CAR T cells as a single treatment. Treatment was administered when tumor volumes reached 150 $mm^3$-250 $mm^3$. Tumor volume and survival were monitored bi-weekly measurements until the tumors reached a size of 2.0 $cm^3$ or mice showed signs of graft versus host disease. Animals were removed from study and studies terminated following onset of GVHD when animals display hunched posture, rapid breathing, urine staining, weight loss and a body condition score of 2, as determined by visual inspection. Onset of GVHD defined as urine staining and weight loss of 20% or weight loss of 10-15% if accompanied by hunched posture, labored breathing, or poor body condition.

Example 2—Results

PC-CAR T cell engineering for PHOX2B. Due to the lack immunogenicity of self-antigens, the inventors pursued development of scFv-based CARs rather than engineered T cell receptors (TCRs) for PHOX2B after no high affinity TCRs were identified in multiple screens. They reasoned that immunogenicity could be induced to otherwise immunogenically inert pMHCs using synthetic, peptide-centric receptors.

Figure 1B:
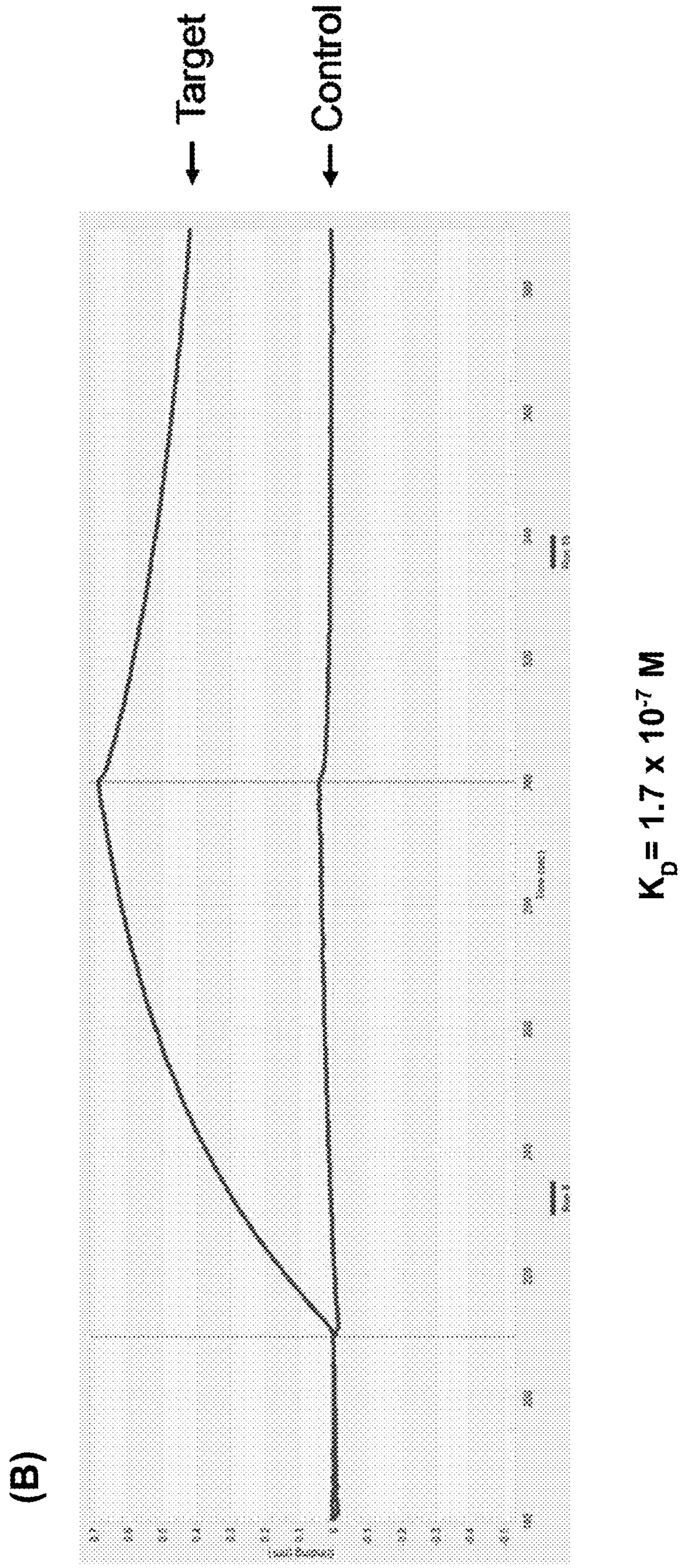
Figure 2A:
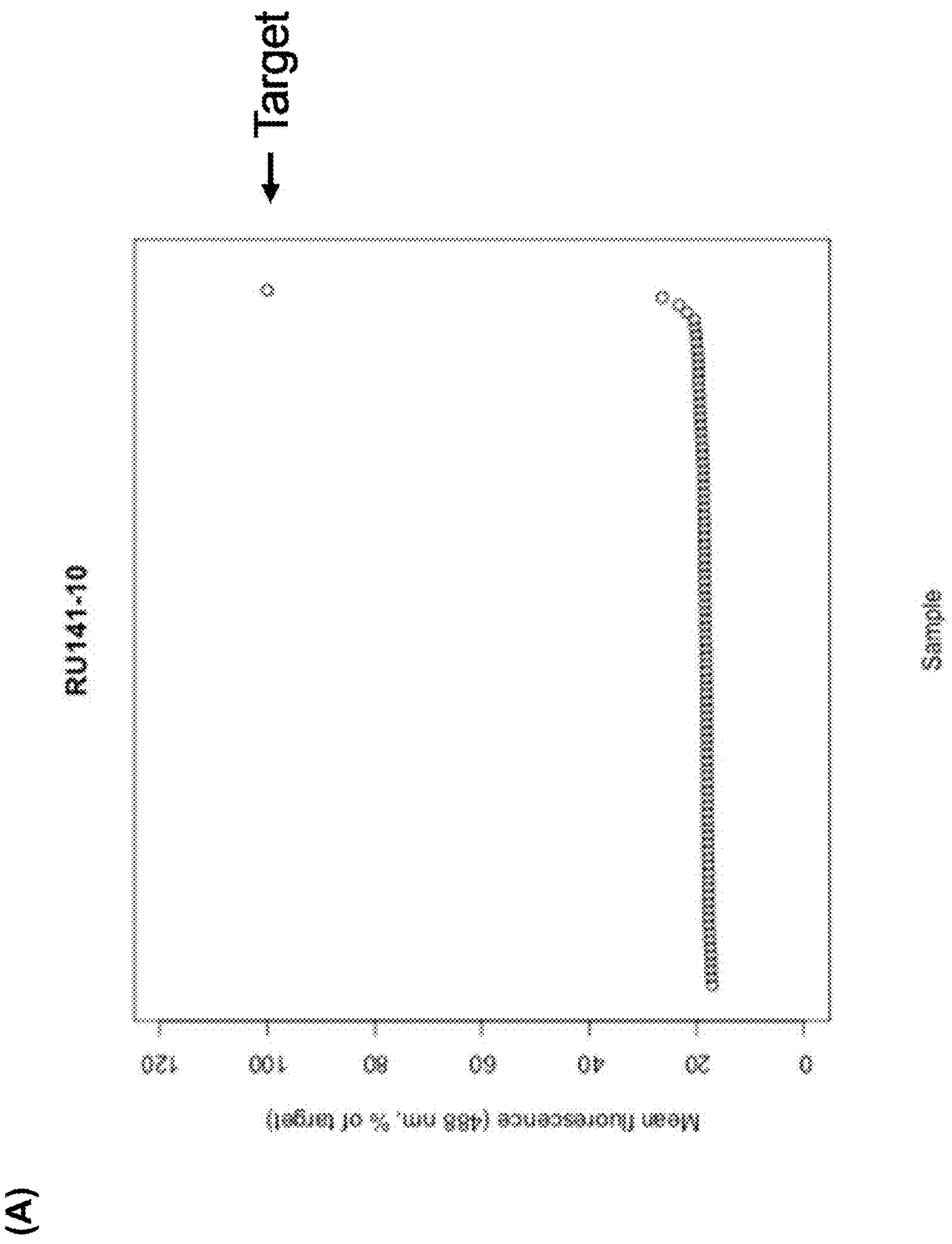
FIGS. 2A-B. Specificity array analysis of clones 10 and 302. The figures depict bead-based binding assays demonstrating the pMHC-specificity of each scFv for the target PHOX2B (43-51) complex vs 95 unrelated complexes. The binding is normalized to the target complex (shown by arrow).
Figure 2B:
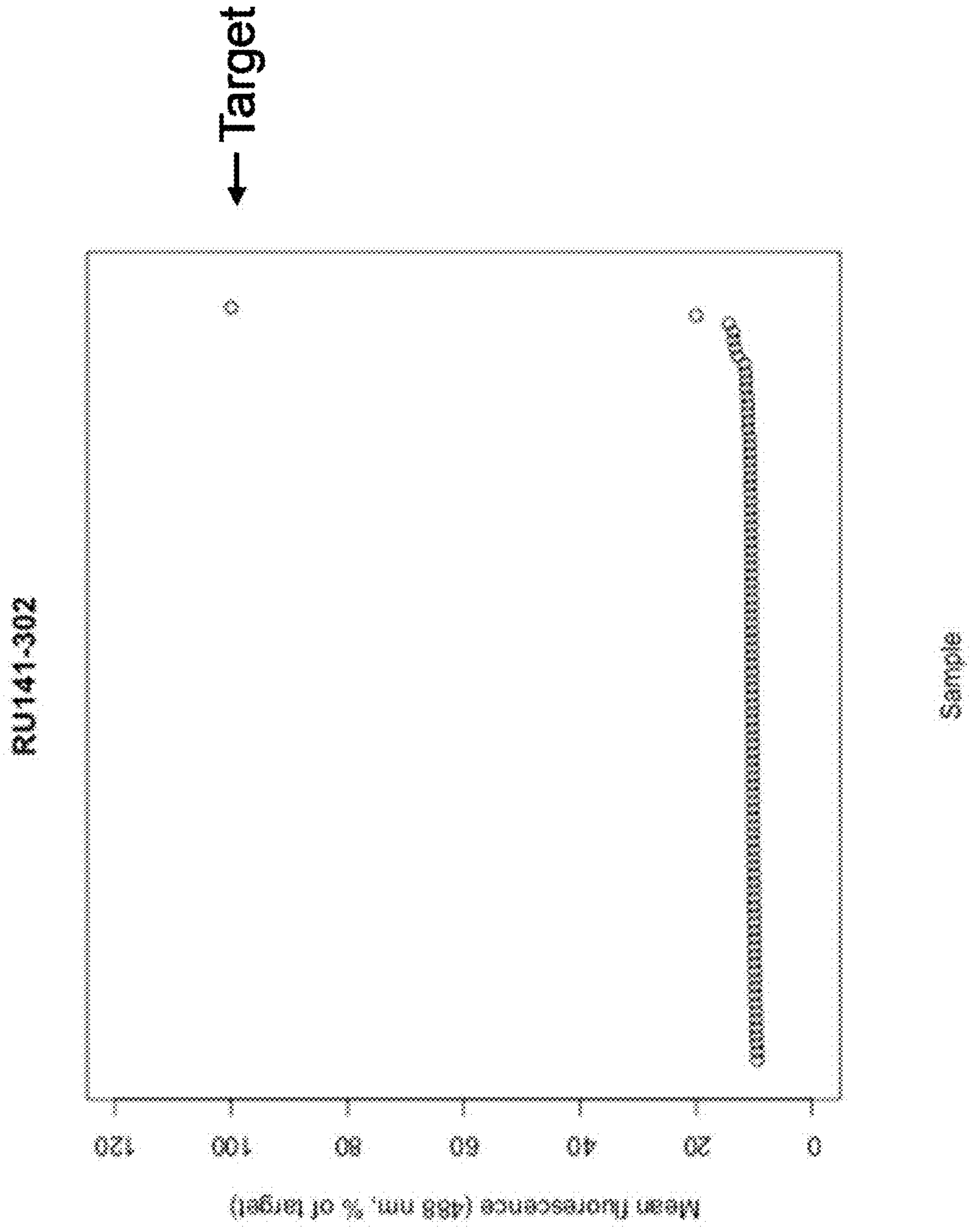
Figure 3A:
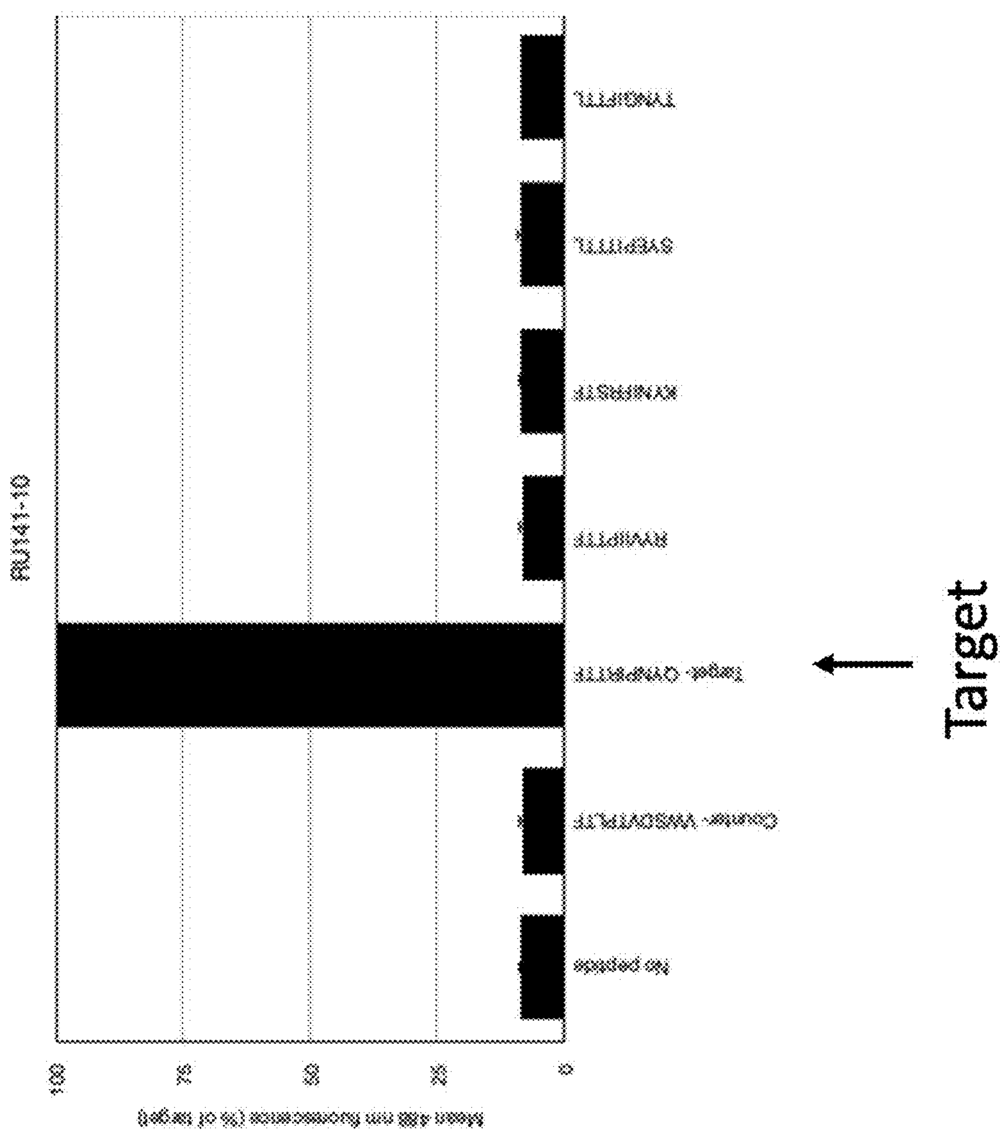
FIGS. 3A-B. Cross-reactivity analysis of clones 10 and 302 to homologous peptides. The figures depict bead-based binding assays demonstrating the pMHC-specificity of each scFv for the target PHOX2B (43-51) complex vs peptides from the proteome and immunopeptidome that are highly homologous to the target peptide. The binding is normalized to the target complex (shown by arrow).
Figure 3B:
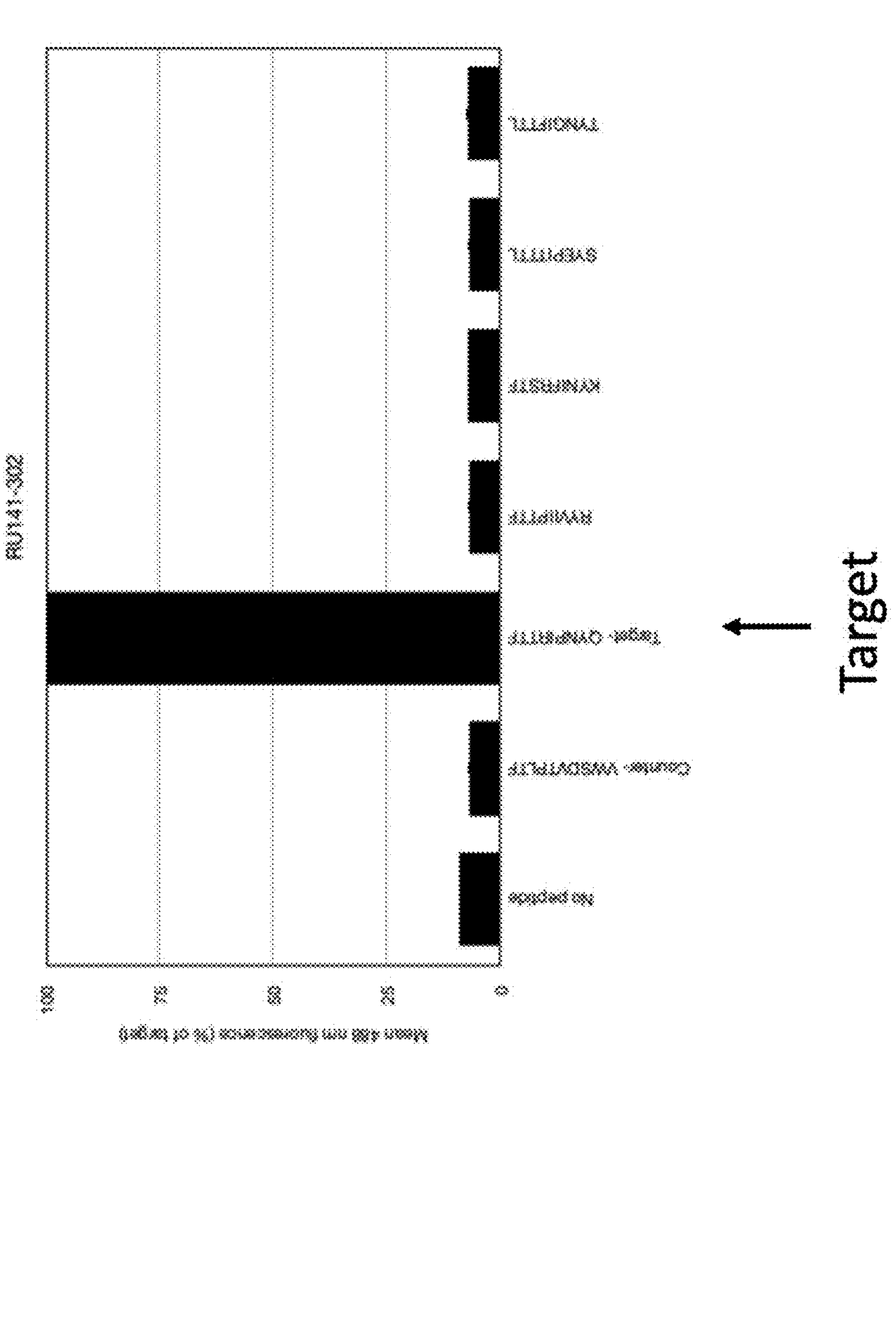
Figure 4:
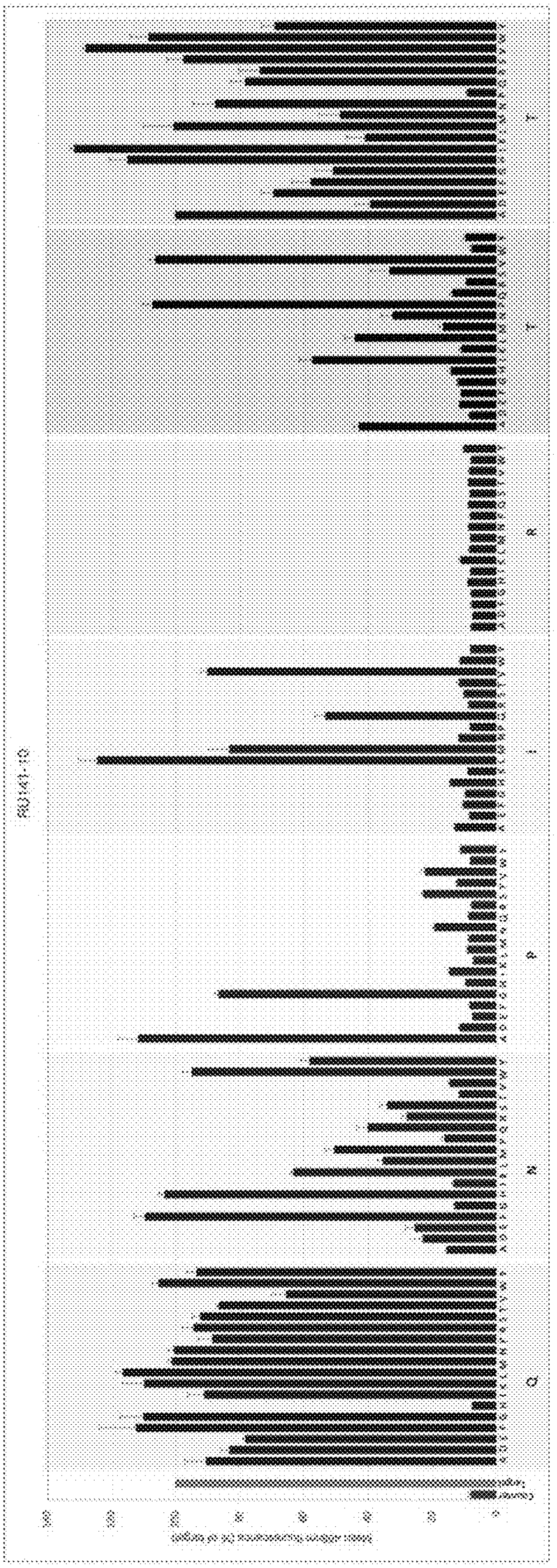
FIG. 4. Binding of PHOX2B (43-51) X-scan peptides to clone 10 scFv. The figure depicts bead-based binding assays demonstrating the binding to complexes loaded with single-residue variants of the PHOX2B (43-51) target peptide. Each non-anchor position of the target peptide was substituted for all other natural amino acids (minus cysteine) to demonstrate the tolerance of clone 10 for substitution at each position. The binding is normalized to the target and a control complex.
Figure 5:
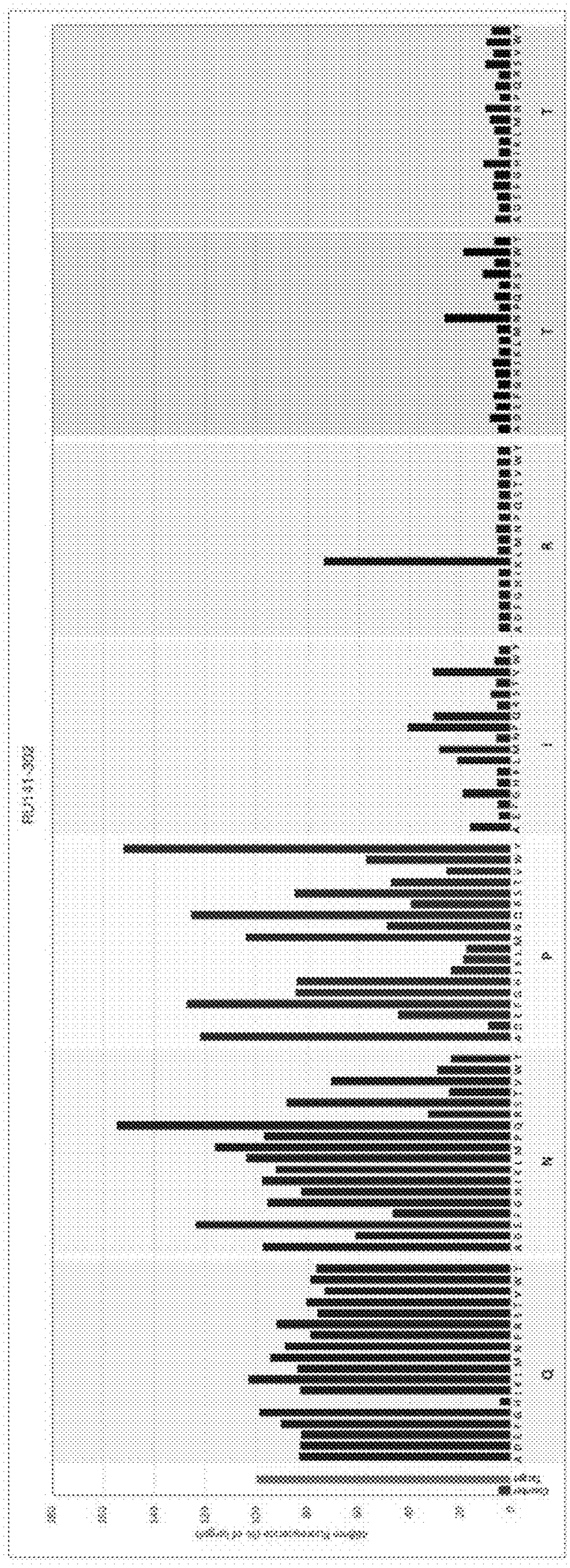
FIG. 5. Binding of PHOX2B (43-51) X-scan peptides to clone 302 scFv. The figure depicts bead-based binding assays demonstrating the binding to complexes loaded with single-residue variants of the PHOX2B (43-51) target peptide. Each non-anchor position of the target peptide was substituted for all other natural amino acids (minus cysteine) to demonstrate the tolerance of clone 302 for substitution at each position The binding is normalized to the target and a control complex.

To screen for PHOX2B peptide-specific clones, the inventors used the Retained Display[56] (ReD) system, a protein display platform that enables the flow-cytometric selection of pMHC-binding scFvs in permeabilized bacterial cells, with a $>10^{11}$-member scFv library. Two clones, 10 (SEQ ID NO: 3) and 302 (SEQ ID NO: 12), were among those isolated and further characterized. FIGS. 1A and 1B show the binding kinetics of scFv protein of clones 10 and 302 to the target PHOX2B (43-51) MHC complex vs binding to an unrelated complex, and also demonstrating the very slow kinetic off-rate of clone 10 ($k_d=7.6\times10^{-4}$/sec). The clones were further characterized by binding against a panel of 95 unrelated peptides and four highly similar peptides (RYVIIPTTF (SEQ ID NO: 61), KYNIFRSTF (SEQ ID NO: 62), SYEPITTTL (SEQ ID NO: 63), TYNGIFTTL (SEQ ID NO: 64)), assembled as HLA-A*24:02 complexes, relative to the target PHOX2B (43-51) complex. FIGS. 2A-B demonstrate that both clones, 10 (FIG. 2A) and 302 (FIG. 2B), display no detectable binding to the panel of 95 unrelated pMHC complexes. In a further display of specificity to the target complex, FIGS. 3A-B shows that both clones, 10 (FIG. 3A) and 302 (FIG. 3B), display highly selective binding to the PHOX2B target pMHC and no detectable binding to 4 peptides that were identified from the human proteome with homology to the target. Two of these peptides, RYVIIPTTF (SEQ ID NO: 61) and KYNIFRSTF (SEQ ID NO: 62), have also been identified using mass spectrometry as presented in vivo by the immunopeptidome (world-wide-web at iedb.org). To resolve the interaction between the scFv and the PHOX2B MHC complex and also to define the sensitivity of specific binding of the clones for the substitution of different amino acids at each position of the target peptide, an 'X-scan' mutagenesis of the PHOX2B target peptide sequentially mutated to 18 natural amino acids (other than cysteine) at positions 1, 3, 4, 5, 6, 7 and 8 (i.e., the non-anchor positions) was performed. FIG. 4 shows that clone 10 has tolerances for Phe/His/Lys/Trp/Tyr at position 3 (Asn for PHOX2B), but strongly prefers the PHOX2B target identity for positions 4, 5 and 7 and has an absolute restriction for Arg at position 5. FIG. 5 shows that Clone 302 shows a very specific footprint over positions 5, 6, 7 and 8 with restrictions on position 4. This strong interaction of the binding agents of the invention with 4+ residues of the PHOX2B target peptide highlights the superior selectivity of PC-CARs as compared to the 3-4 residues that typically interact with the TCR[58].

To address cross-reactivity with pMHC in normal tissues, the inventors developed an algorithm to predict potential selective Cross-Reactive Antigen Presentation (sCRAP; marisshiny.research.chop.edu/sCRAP) on the same HLA allotype (FIGS. 25A-C), allowing pre-emptive selectivity filtering in early stages of scFv screening without the need of a prior alanine scan or receptor[57]. They benchmarked the sCRAP algorithm by testing its ability to predict the cross-reactivity of the MAGE-A3 peptide presented on HLA-A*01:01, whose targeting using an affinity-enhanced TCR previously resulted in the fatal cross-reaction with another peptide derived from the TITIN protein presented on HLA-A*01:01 in myocardial tissues[15]. The inventors predicted the cross-reactivity of MAGE-A3 with the TITIN peptide as the 4$^{th}$ ranked prediction out of 1,143,861 potential self-peptides presented in heart tissue (FIGS. 26A-B).

The inventors then screened their panel of PHOX2B-directed CARs against the top seven pMHC predicted by sCRAP (FIG. 6), thus eliminating cross-reactive CARs and prioritizing those with the highest degree of target selectivity. The inventors identified clone 10LH CAR (SEQ ID NO: 21) and clone 302LH CAR (SEQ ID NO: 22) as possessing the highest specificity profile for further development.

Figure 7:
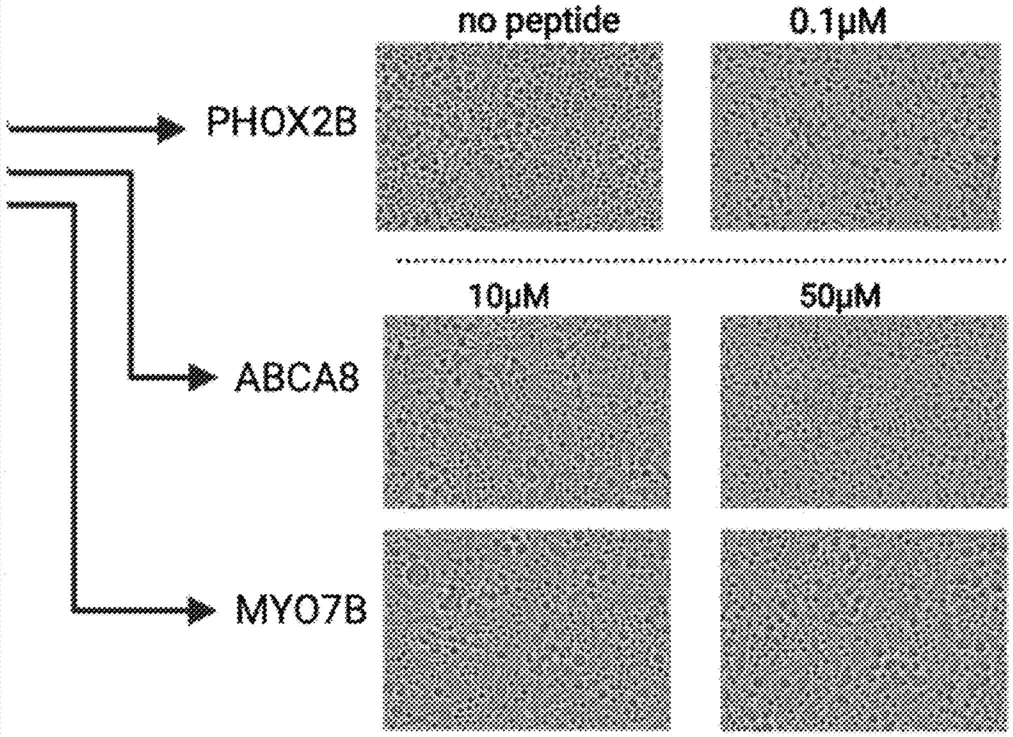
FIG. 7. Functional demonstration of target selectivity by clone 10 LH CAR. The figure demonstrates the binding of the clone 10 LH CAR to predicted cross-reactivity peptides. For two peptides with demonstrated tetramer binding, ABCA8 and MYO7B, functional screening on peptide-pulsed SW620 cells shows CAR killing only through ABCA8 at supraphysiological concentration of 50 μM as compared to PHOX2B killing at 0.1 μM. ABCA8 and MYO7B were not detected in the normal tissue immunopeptidome, and none of the peptides predicted by sCRAP that were detected in the normal immunopeptidome (FDFTI, SLC23A2, and TNS4) demonstrate binding to 10LH.

To test the functional significance of the binding to potential off-target pMHCs predicted by sCRAP, the inventors pulsed HLA-matched/PHOX2B negative SW620 colon adenocarcinoma cells with the PHOX2B peptide and potential cross-reactive peptides across a range of concentrations (FIG. 7). Pulsing with the PHOX2B peptide resulted in complete cytotoxicity when co-cultured with 10LH at the lowest tested concentration of 0.1 μM. 10LH CAR T cells did not induce cytotoxicity with the most cross-reactive predicted peptide ABCA8 at 10 μM, and only induced killing at the supraphysiological concentration of 50 μM. The second most cross-reactive peptide with 10LH (MYO7B) showed no CAR cytotoxicity at concentration up to 50 μM. Neither ABCA8 nor MYO7B has been detected in normal tissue immunopeptidome[11], and none of the peptides previously detected in the normal tissue immunopeptidome display any cross-reactivity with PC-CAR 10LH. These screens demonstrate the utility of sCRAP to pre-emptively identify off-target effects, efficiently screen their functional consequences, and identify binders with highly selective binding to tumor targets.

Figure 9A:
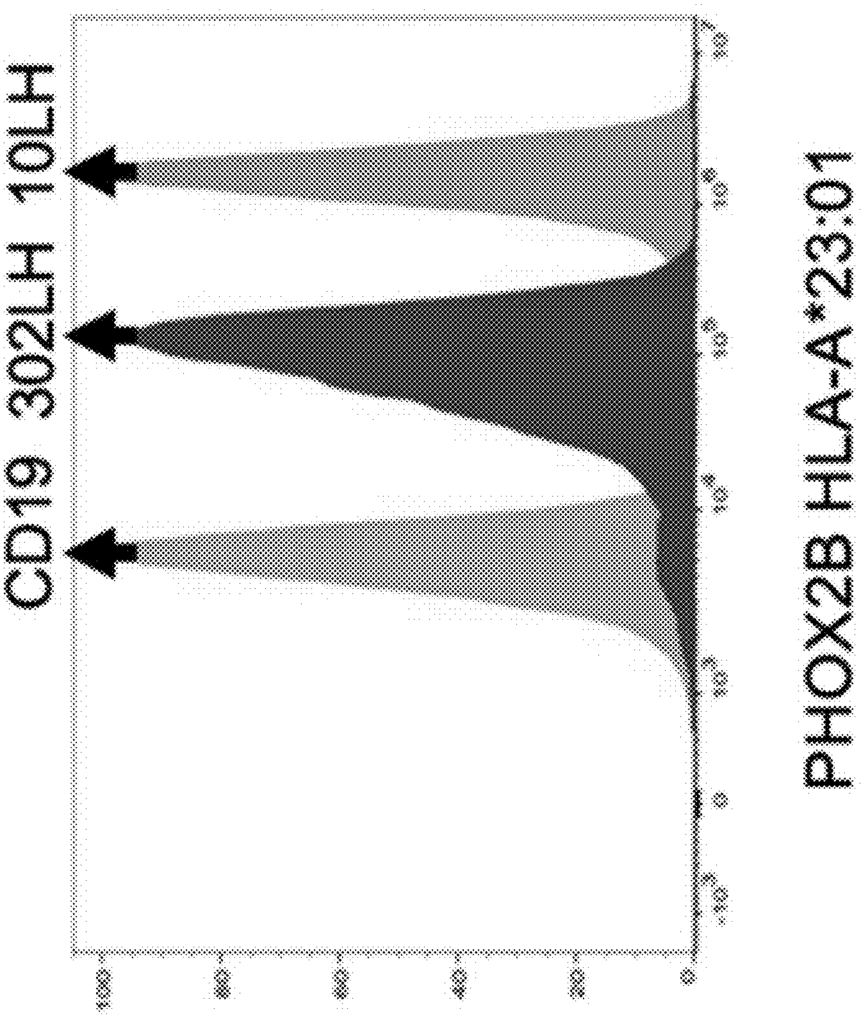
FIGS. 9A-B. Cross-HLA recognition of the PHOX2B peptide.
Figure 9B:
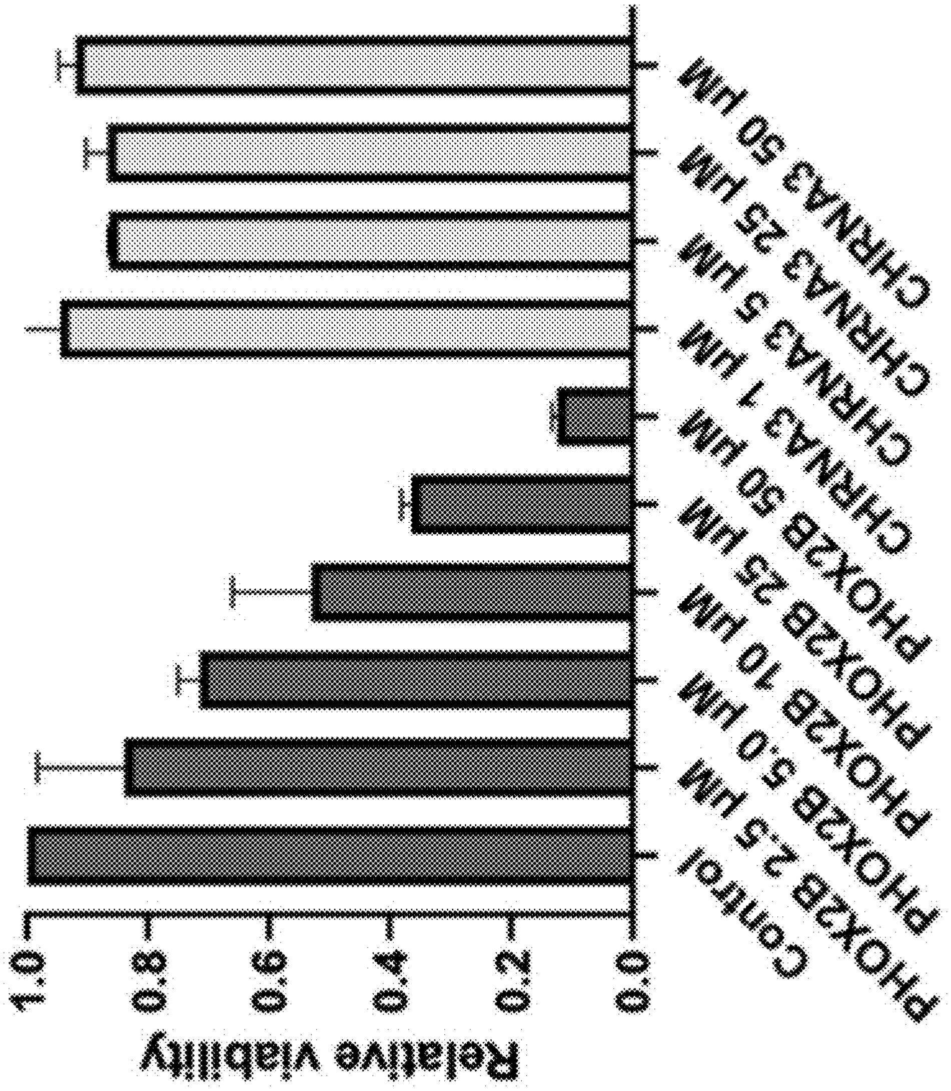

PC-CAR T cells break HLA restriction imposed on conventional TCRs. Given the prerequisite of antigen processing and presentation necessary for detection of a given MHC peptide by immunopeptidomics, the inventors hypothesized that identical peptides could be presented on additional HLA allotypes capable of binding a peptide's anchor resides, and that some of these peptides could be presented in a similar enough conformation to be recognized by peptide-centric scFv binders. They used their population-scale antigen presentation tool ShinyNAP[7] to identify additional HLA allotypes that could present the same PHOX2B peptide, identifying 8 additional HLAs predicted to bind the PHOX2B 9-mer. The inventors then used their pMHC structural modeling software, RosettaMHC[59], to model the 3D conformation and binding free energy of peptides presented by additional HLA alleles, identifying HLA-A*23:01 and HLA-B*14:02 as top-scoring candidates for recognition by PC-CARs of the PHOX2B peptide originally discovered on HLA-A*24:02. After validating binding of QYNPIRTTF (SEQ ID NO: 1) to these alternate allotypes the inventors measured the ability of 10LH to recognize these pMHCs, finding that in addition to HLA-A*24:02, 10LH binds with high affinity to the PHOX2B 9mer QYNPIRTTF (SEQ ID NO: 1) presented by HLA-A*23:01 and HLA-B*14:02 (FIGS. 8A-C). The inventors also found that though QYNPIRTTF (SEQ ID NO: 1) binds to HLA-C*07:02, 10LH had 17.4-fold lower binding to HLA-C*07:02. To demonstrate functionally relevant recognition of their prediction of PHOX2B presentation on HLA-A*23:01, the inventors pulsed the HLA-A*23:01/PHOX2B$^{-}$ melanoma cell line WM873 with the QYNPIRTTF (SEQ ID NO: 1) peptide, showing induction of antigen-specific killing in peptide-pulsed cells and no cytotoxicity in cells pulsed with mismatched peptide (FIGS. 9A-B). HLA-A*23:01 is the most common non-A2 allele in people of African ancestry, highlighting the potential of PC-CARs to expand clinical application to underserved populations. These findings demonstrate the potential to significantly expand the eligible patient population receiving peptide-centric scFv-based immunotherapies.

Figure 10:
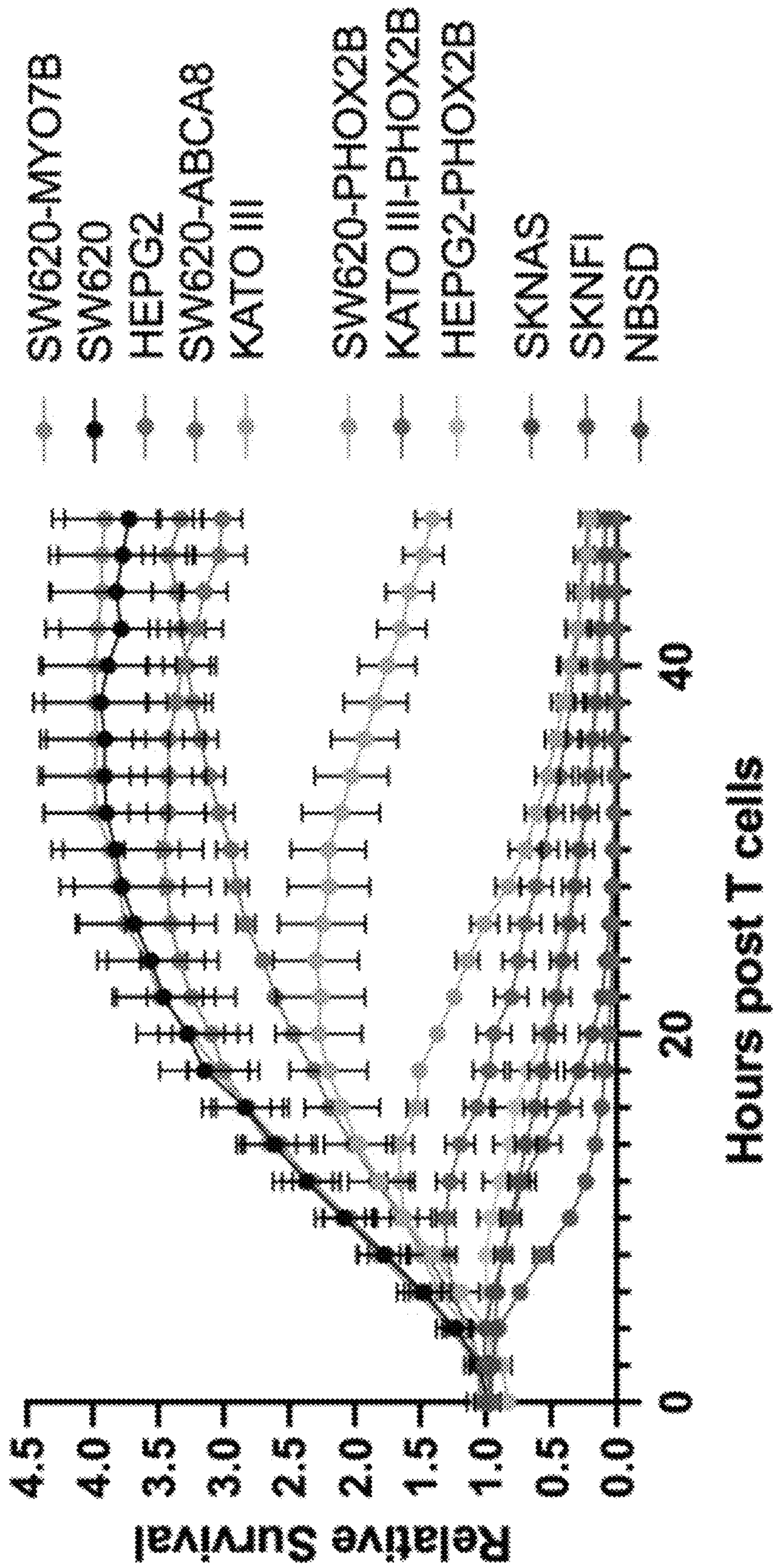
FIG. 10. PHOX2B-specific PC-CAR T cells induce potent tumor killing in neuroblastoma lines in vitro. The figure demonstrates that clone 10LH CAR induces specific killing and IFN-γ release in neuroblastoma cells expressing HLA-A*24:02 and HLA-A*23:01 and PHOX2B (SKNAS, NBSD, and SKNFI), but not in HLA-A*24:02/PHOX2B$^-$ non-neuroblastoma tumor cells (SW620, HEPG2, and KATO III), unless PHOX2B peptide is added. No T cell activity was observed in SW620 when pulsed with 10 μM of predicted cross-reactive peptides ABCA8 or MYO7B. Cytotoxicity was visualized by loss of green fluorescence in GFP-transduced cancer cells and IFN-γ release measured by ELISA. The order of the listed cells on the right is the same as the final right hand data point for each.
Figure 11:
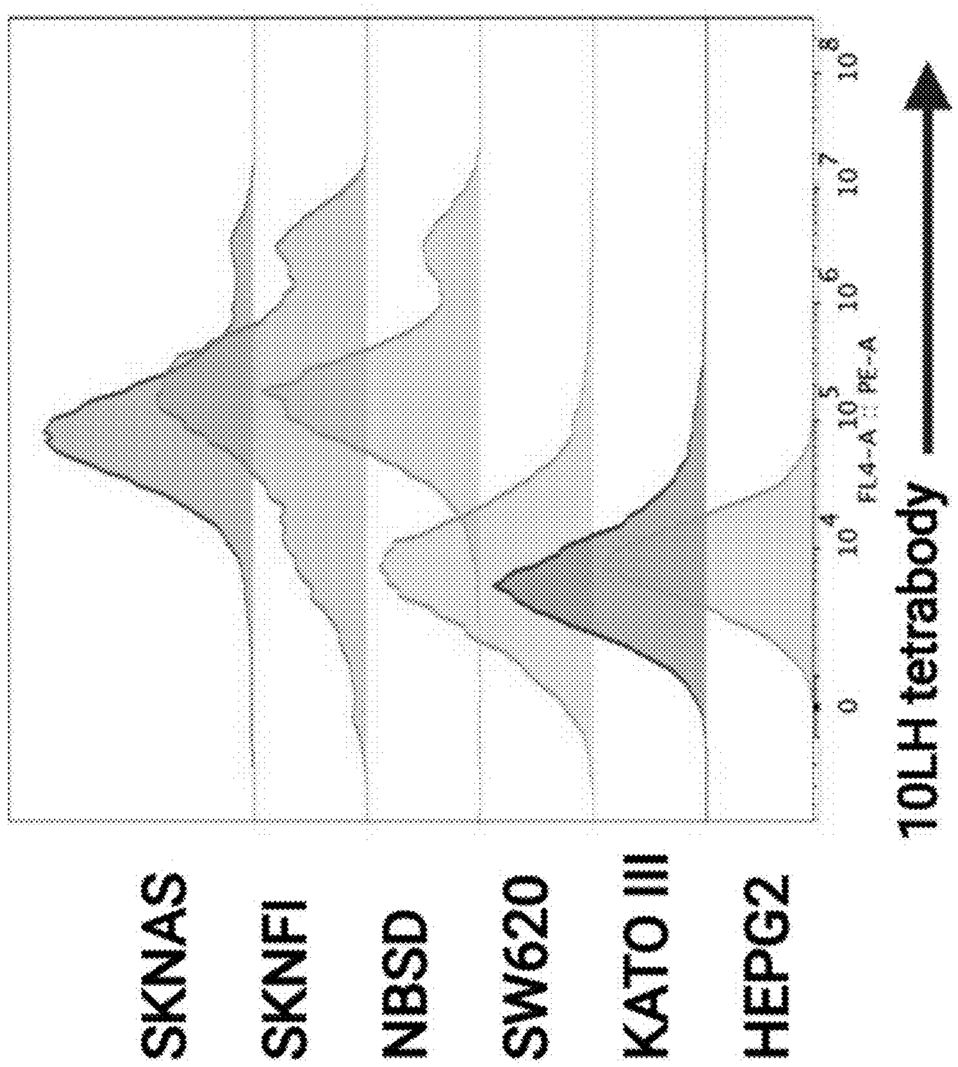
FIG. 11. Antibodies specific to PHOX2B 43-51 MHC stain PHOX2B positive neuroblastoma cells in vitro. The figure demonstrates staining of cancer cells with tetramerized 10LH scFv allows detection of PHOX2B pMHC on neuroblastoma cells but not in HLA-matched controls.

PHOX2B-directed PC-CAR T cells have potent antitumor activity in neuroblastoma preclinical models. The inventors next tested the on-target killing potential of 10LH using available HLA-A*24:02 and HLA-A*23:01 neuroblastoma cell lines (SKNAS, NBSD, and SKNFI) and showed complete tumor cell killing and potent IFN-γ release after 24 hours at 5:1 effector to target ratio (E:T) (FIG. 10). They tested the functional cross-reactivity of PC-CARs against the milieu of peptides presented by off-target tissues, showing no activity in three HLA-A*24:02 cell lines that do not express PHOX2B (SW620; colorectal adenocarcinoma, KATO III gastric adenocarcinoma, and HEPG2 hepatocellular carcinoma). To validate the specificity of PC-CARs killing, the inventors pulsed HLA-matched, PHOX2B negative cancer cell lines with the PHOX2B peptide as well as forcibly over-expressing PHOX2B. They demonstrated specific killing only in cells pulsed with PHOX2B peptide and those transduced with full length PHOX2B mRNA, and not in cells pulsed with a non-specific CHRNA3, ABCA8, and MYO7B peptides presented on the same HLA, nor in cells transduced with full length PRAME mRNA, demonstrating that native PHOX2B is processed and presented on MHC where it is specifically recognized by PC-CARs. To detect PHOX2B pMHC on the cell surface, the inventors generated a tetramerized 10LH scFv and stained on- and off-target cell lines, showing significant surface PHOX2B pMHC in neuroblastoma cells and not in HLA-matched controls (FIG. 11), suggesting that these reagents have the potential to be used to assess the presence of antigen in biopsied tissue samples. They also found that CARs flagged as cross-reactive by sCRAP demonstrate significant cross-reactivity, validating the functional consequences of cross-reactivities by their algorithm (data not shown).

Figure 12:
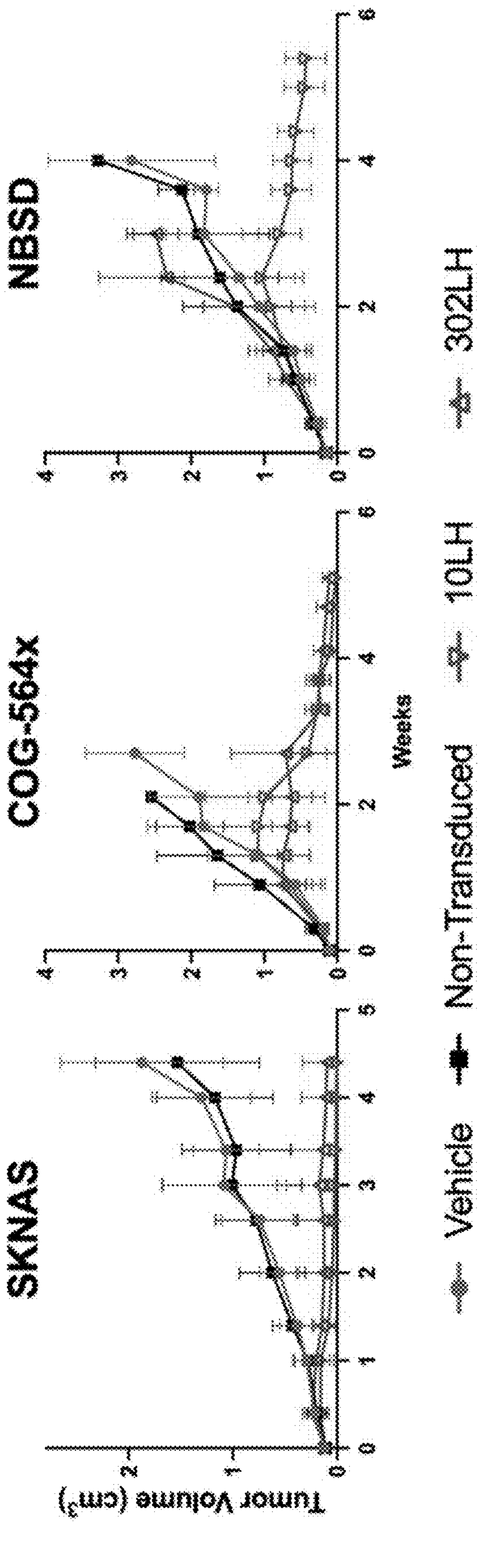
FIG. 12. PHOX2B-specific PC-CAR T cells induce potent tumor killing in vivo and break conventional HLA restriction. PHOX2B-specific PC-CAR T cells induce potent tumor killing in mice engrafted with neuroblastoma PDX tumors including the extremely fast-growing line COG-564x and HLA-A*23:01 line NBSD. Six mice enrolled per arm; data shown from one of two in vivo studies for each PDX line.
Figure 13:
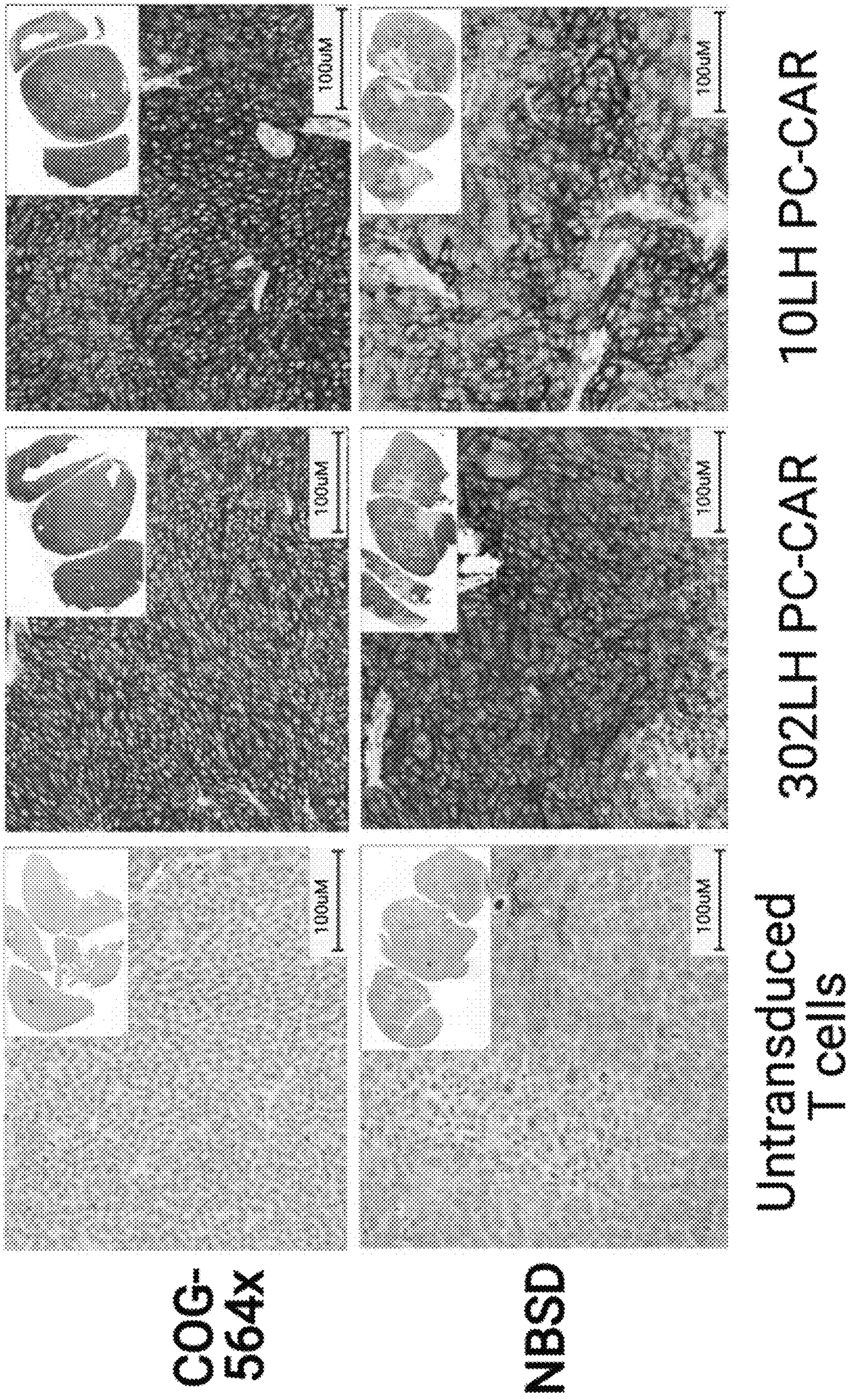
FIG. 13. PHOX2B-specific PC-CAR T cells induce MHC upregulation in MHC-low neuroblastoma models in vivo. Treatment with 10LH and 302LH PC-CARs potently upregulate HLA expression in PDX tumors collected from mice reaching tumor burden as compared to mice treated with untransduced T cells (COG-564x collected 11 days post-treatment; NBSD collected 14 days post-treatment for UT and 17 days post-treatment for 10LH and 302LH).
Figure 14A:
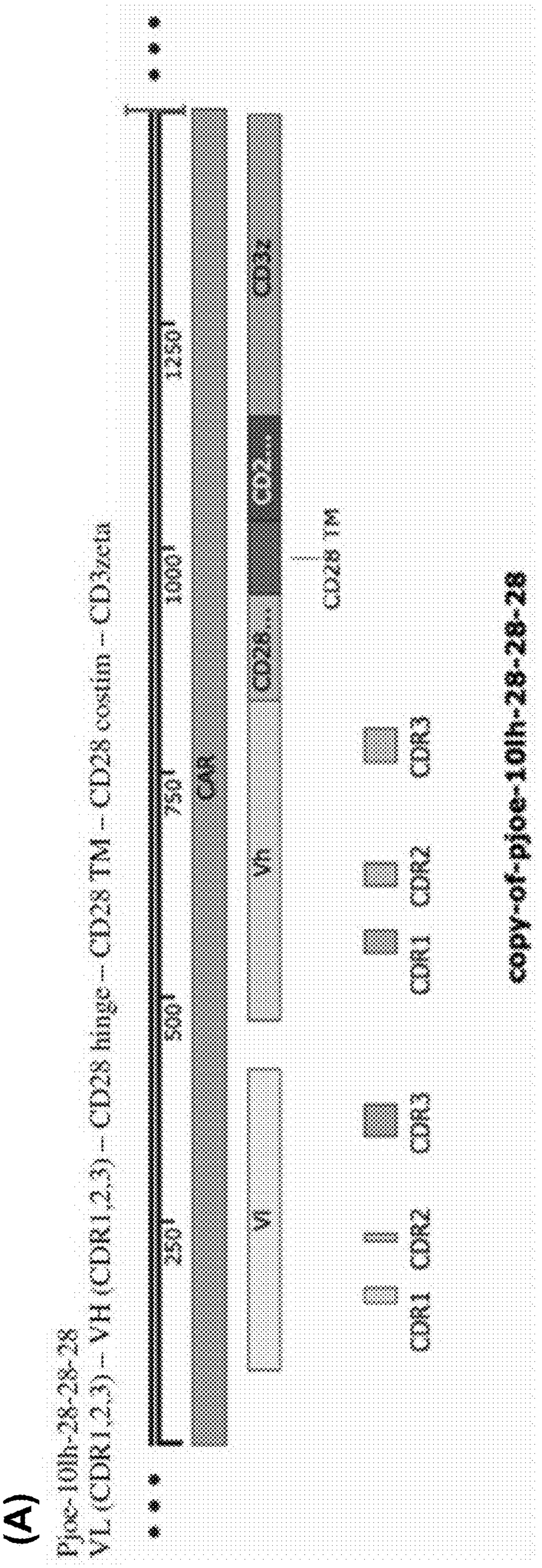
FIGS. 14. A-H. Constructs for various chimeric receptors.
Figure 14B:
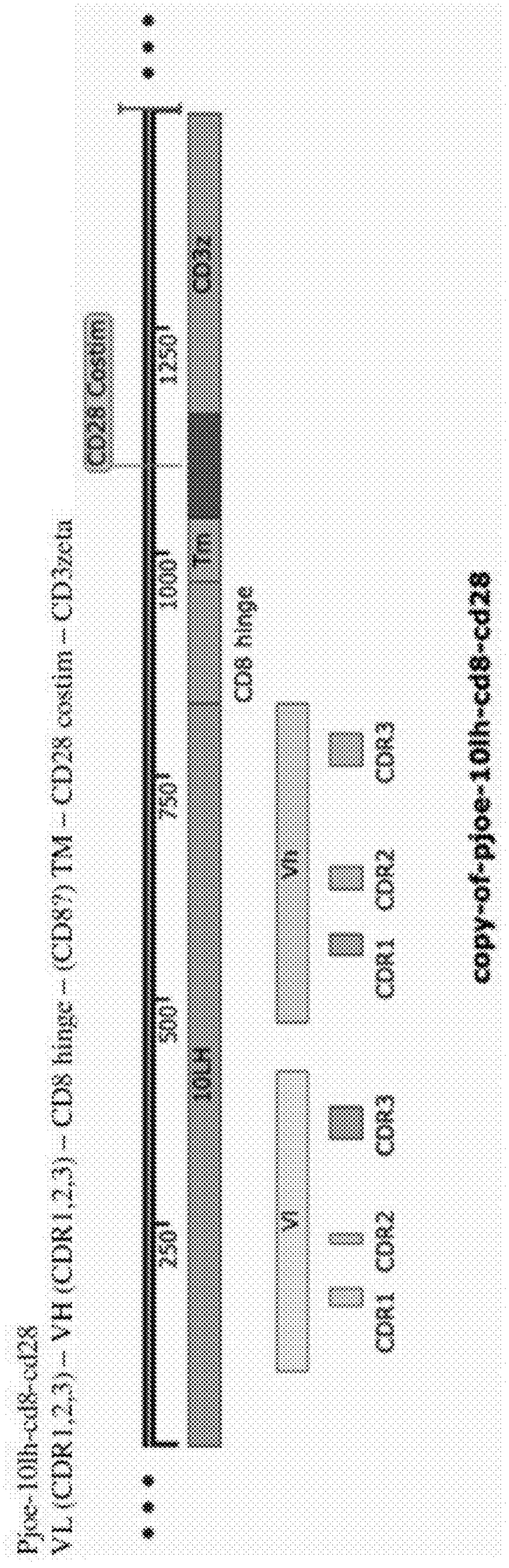
Figure 14C:
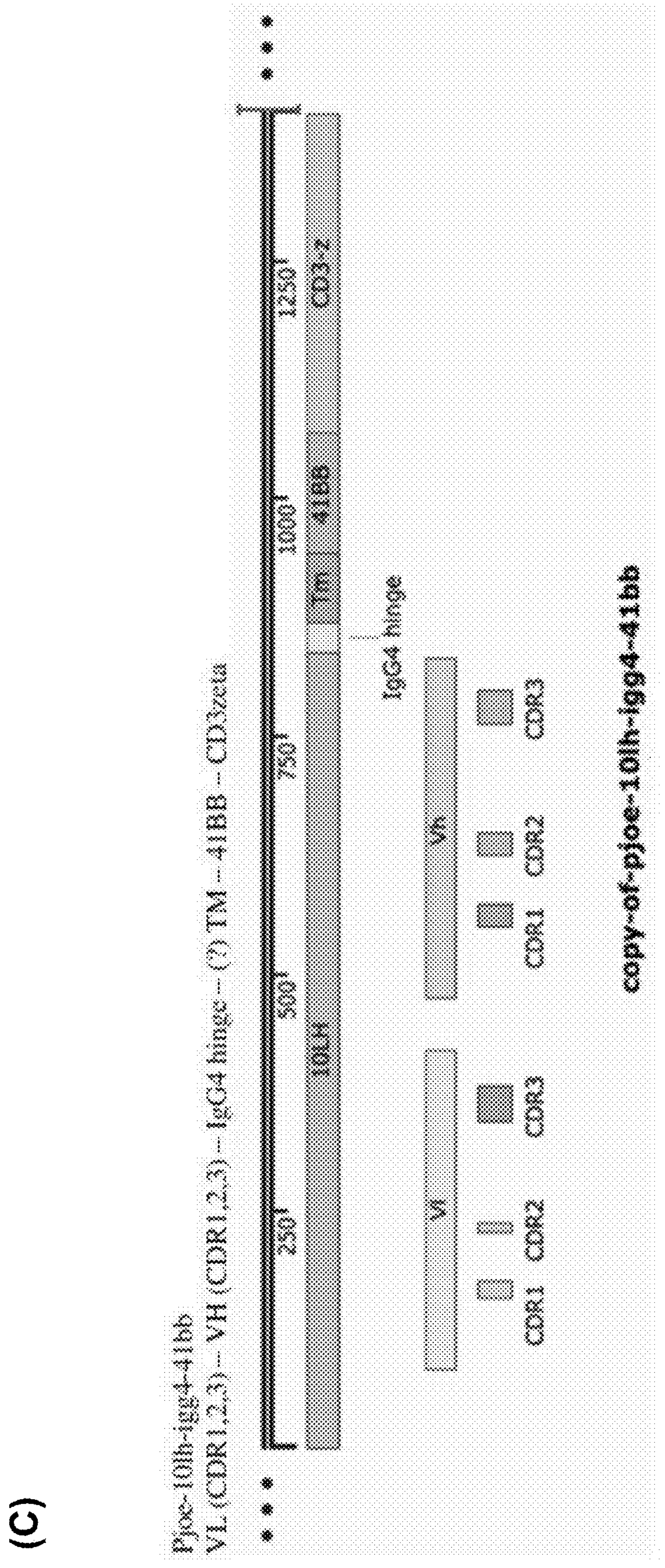
Figure 14D:
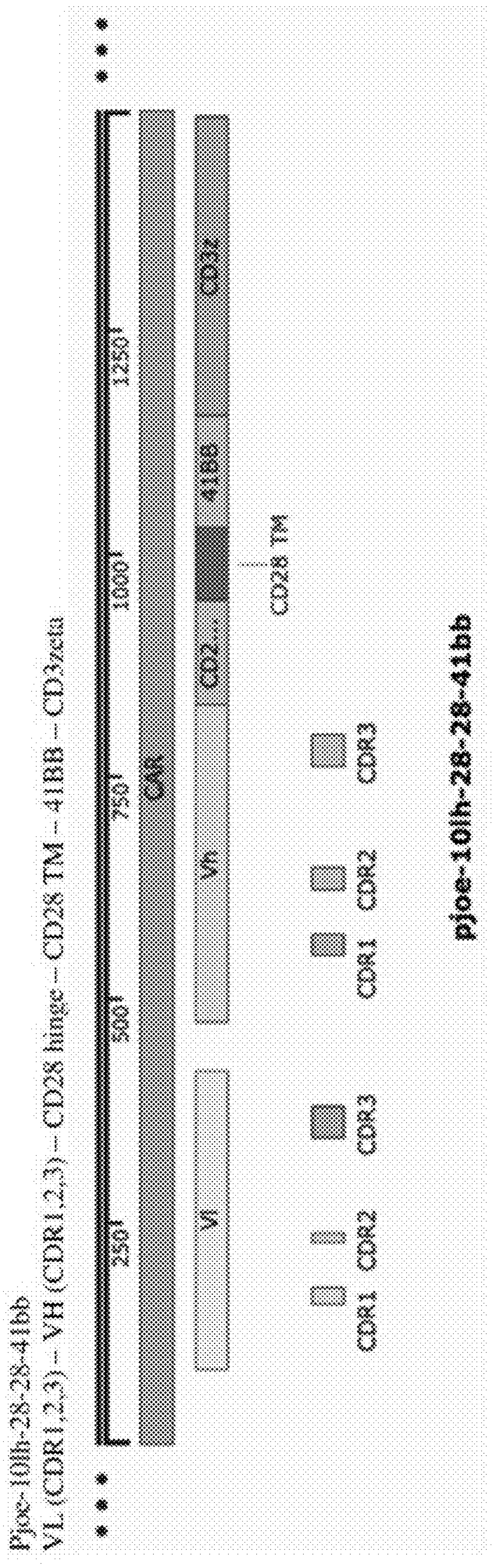
Figure 14E:
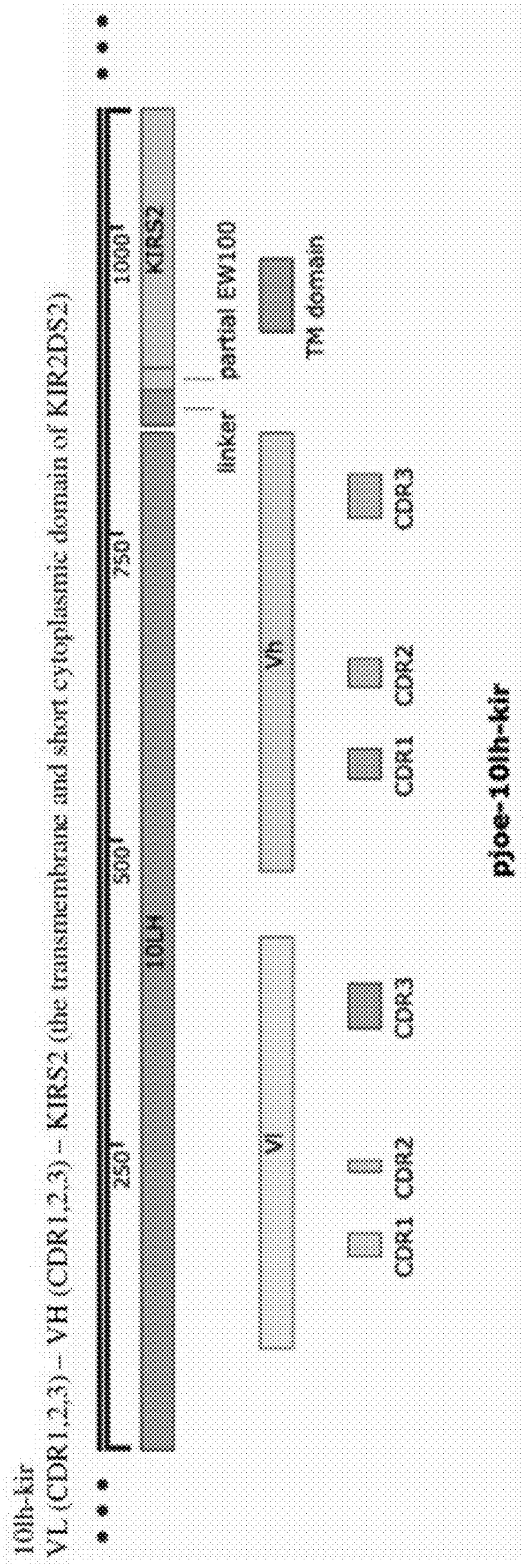
Figure 14F:
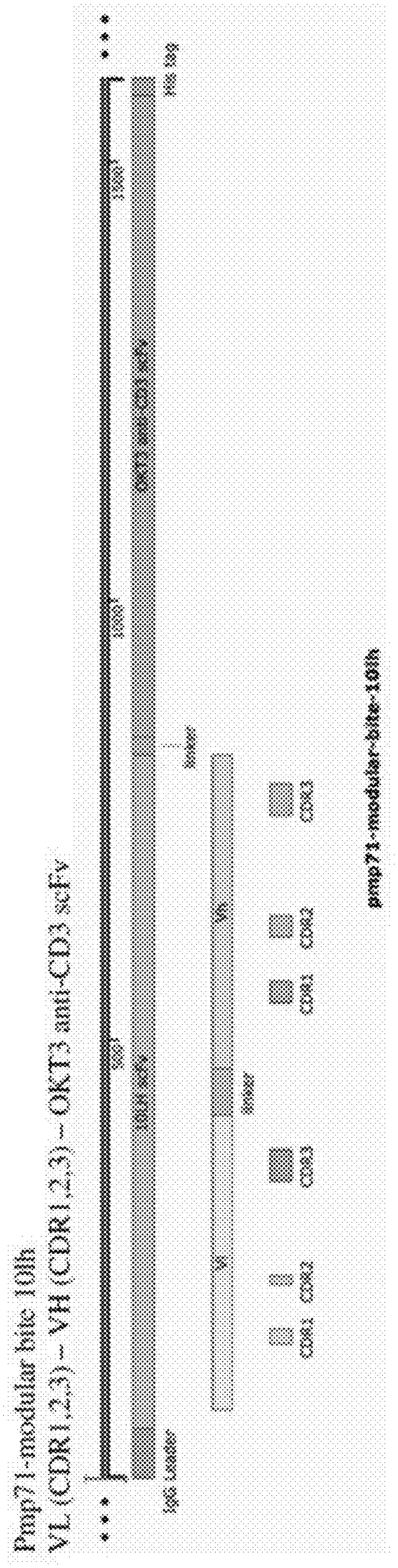
Figure 14G:
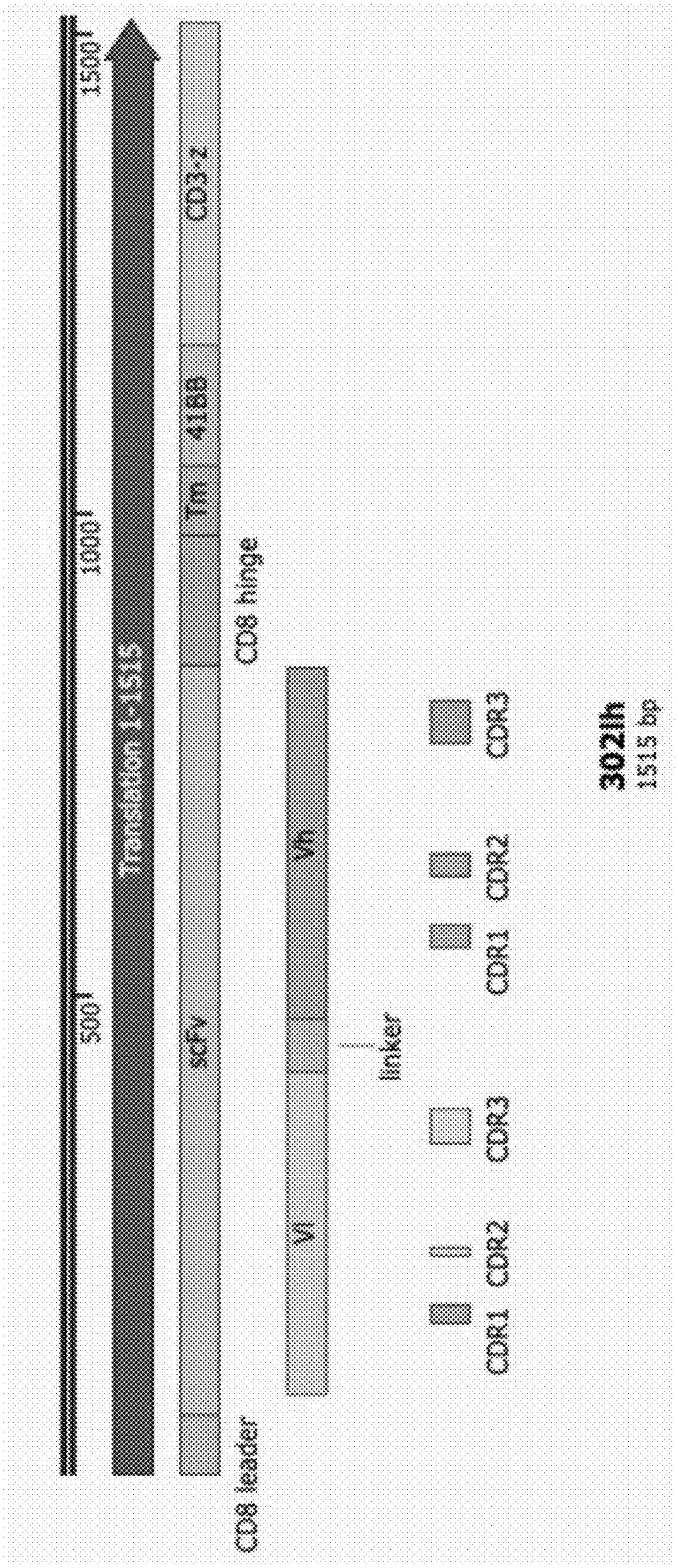
Figure 14H:
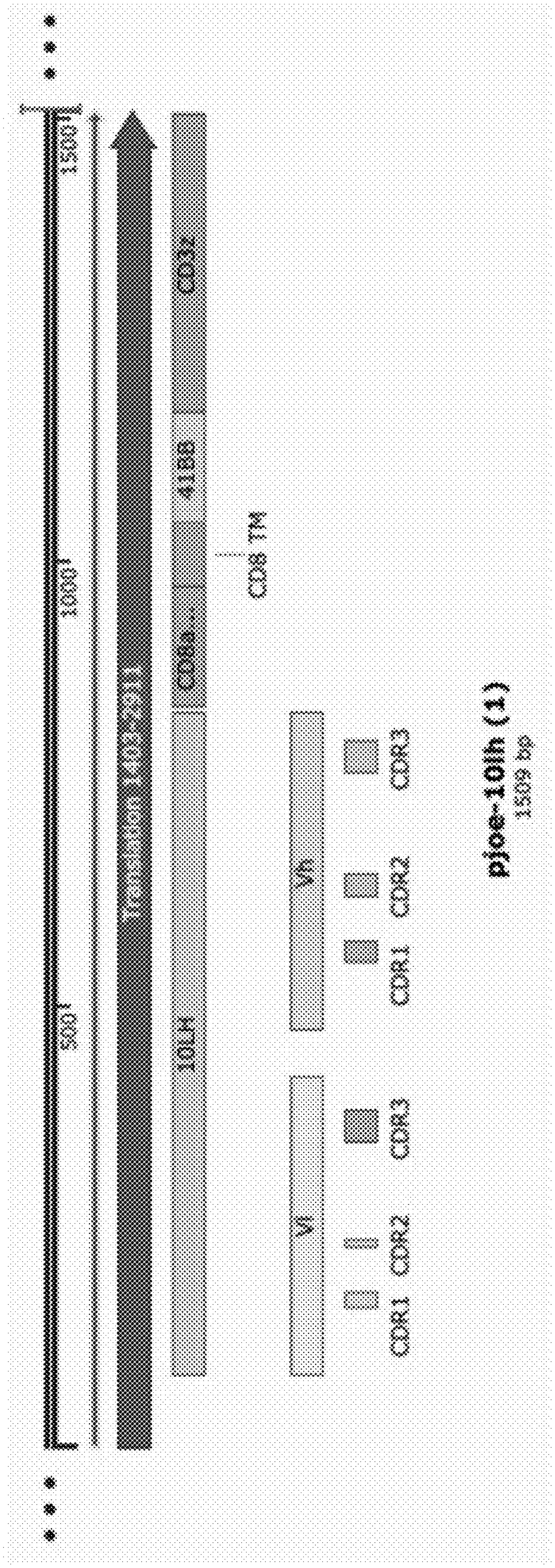
Figure 15A:
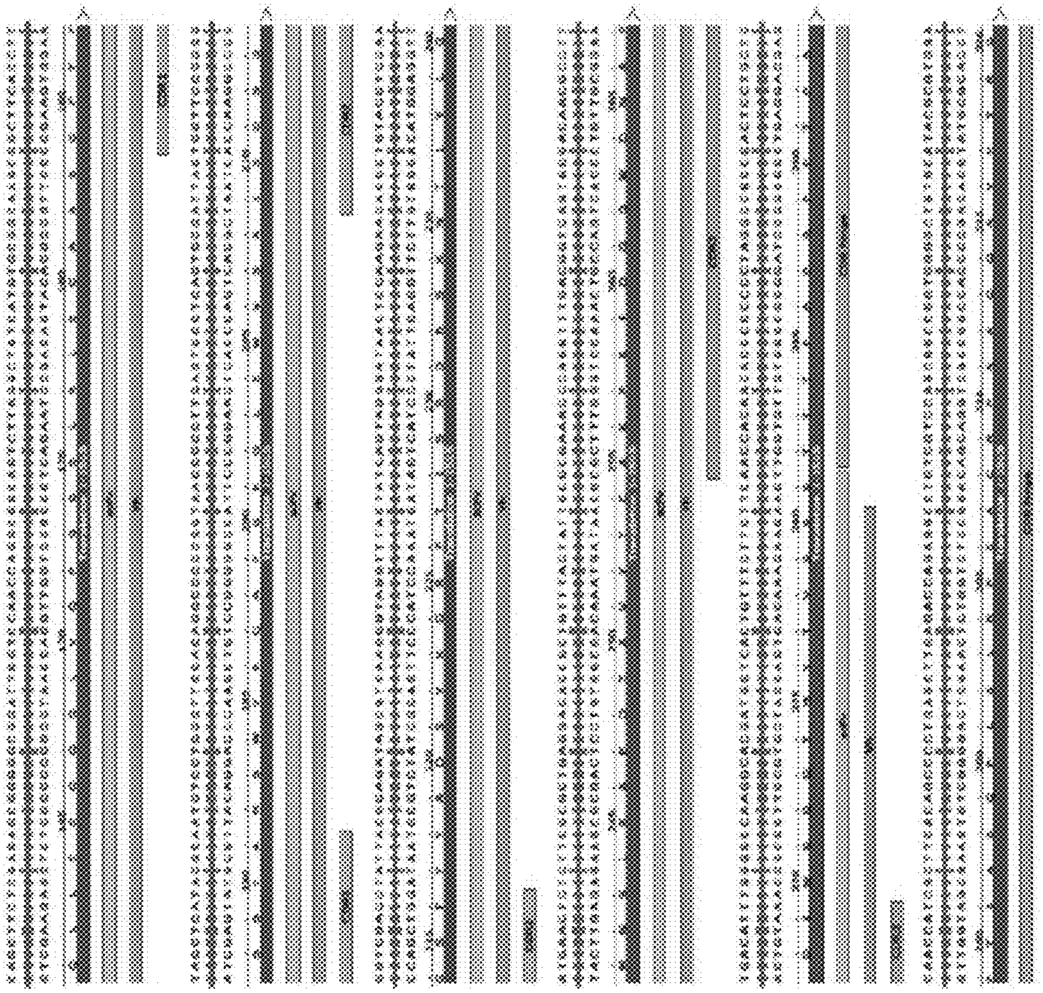
FIGS. 15A-B. Sequences for chimeric receptors.
Figure 15B:
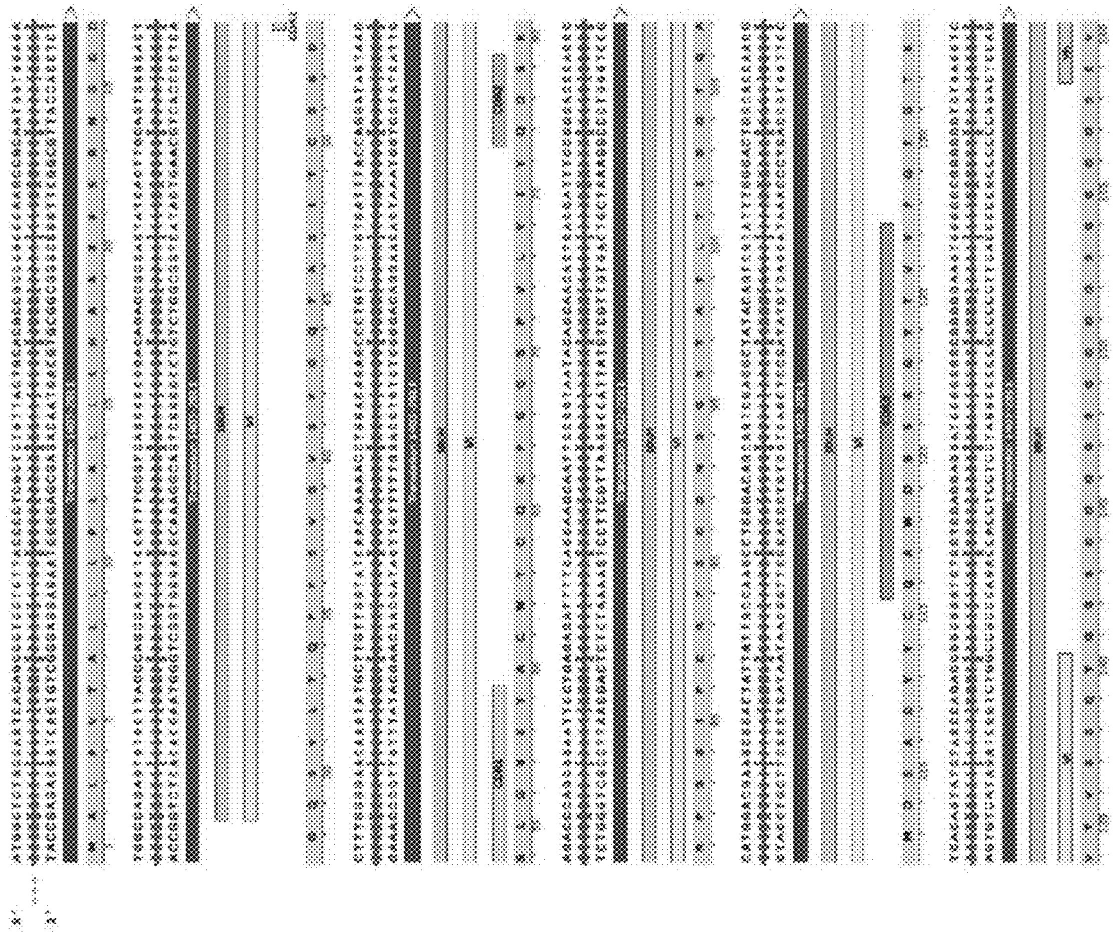

The inventors next treated immunodeficient mice engrafted with HLA-A*24:02 (SKNAS and COG-564x) and HLA-A*23:01 (NBSD) xenografts with $10^6$ 10LH and 302LH transduced CAR T cells once tumors reached 100 $mm^3$-250 $mm^3$. Both 10LH and 302LH PC-CAR treated mice showed complete tumor responses in both HLA-A*24:02 xenografts (FIG. 12), but only for the 10LH-treated mice in the HLA-A*23:01 NBSD xenografts. This correlated directly with the relative affinity of these two constructs against the PHOX2B peptide presented on HLA-A*23:01 (FIG. 9A), suggesting that a threshold affinity or distinct mode of binding by different scFvs may contribute to the ability to recognize the peptide in slightly altered conformations when presented by different HLA alleles. The inventors also observed that CAR treatment induced striking upregulation of MHC in tumors. The COG-564x PDX model was generated from a post-mortem blood-draw from a patient with high-risk MYCN amplified neuroblastoma who had suffered multiple relapses and shows an extremely rapid tumor growth rate in mice. In this experiment, one mouse treated with the 10LH construct had a tumor reach endpoint size of 2 $cm^3$ just one week after PC-CAR T cell therapy and was available for analysis, while all other tumors in this arm nearly reached endpoint size and then all regressed. The lone COG-564x and NBSD tumors that reached endpoint showed significant PC-CAR T cell infiltrate and dramatic upregulation of MHC expression compared to endpoint tumors treated with non-transduced CAR T cells (FIG. 13). This upregulation is likely due to the potent IFN-γ release as measured in vitro, suggesting that these therapies can activate T cell expansion at low antigen density to initiate a feed-forward cascade that increases MHC and antigen presentation.

Figure 16A:
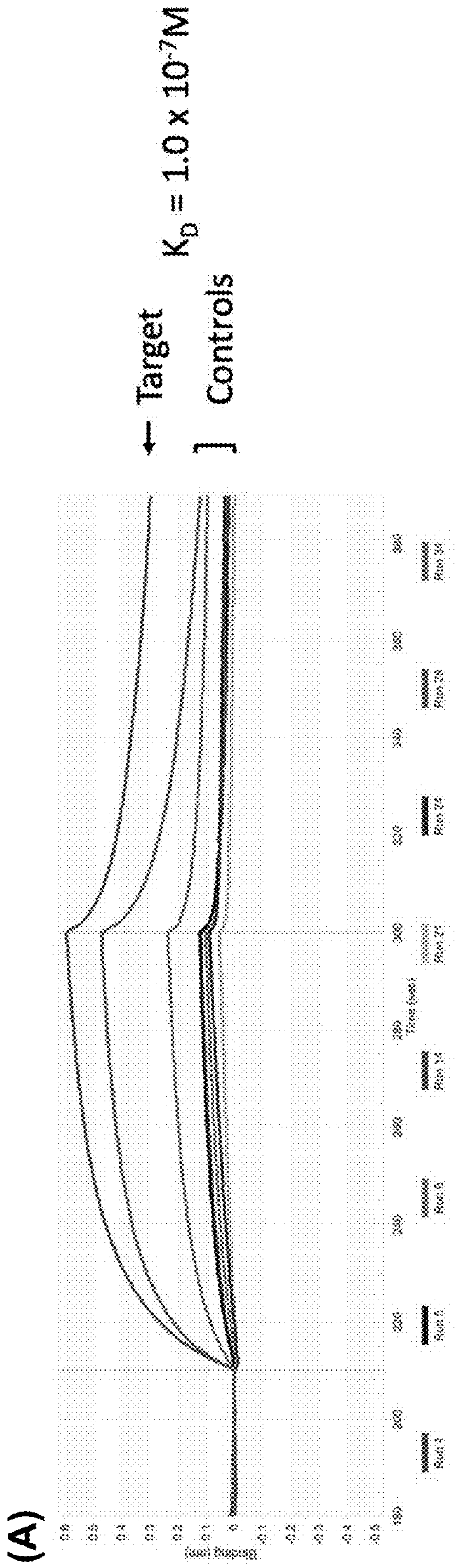
FIGS. 16A-B. Kinetic analysis of clones 9 and 1114. The figures depict the association and dissociation of soluble PHOX2B (43-51) A*24:02 complex with scFv of clone 9 or clone 1114, as measured by bio-layer interferometry (BLI). The binding PHOX2B (43-51) complex (200 nM) is overlaid with non-specific complexes (200 nM) control that differ by one residue from the target PHOX2B complex. Arrow labelled 'Target' shows scFv binding to the PHOX2B (43-51) MHC complex. Arrow labelled 'Controls' shows scFv binding to control peptides (NYTPIRTTF (SEQ ID NO: 52), LYNPIRTTF (SEQ ID NO: 53), QYQPLRTTF (SEQ ID NO: 54), QYNPIKTTF (SEQ ID NO: 55), QYNPLQTTF (SEQ ID NO: 56), QYNPLKTTF (SEQ ID NO: 57), QYNAIRTTF (SEQ ID NO: 58)).
Figure 16B:
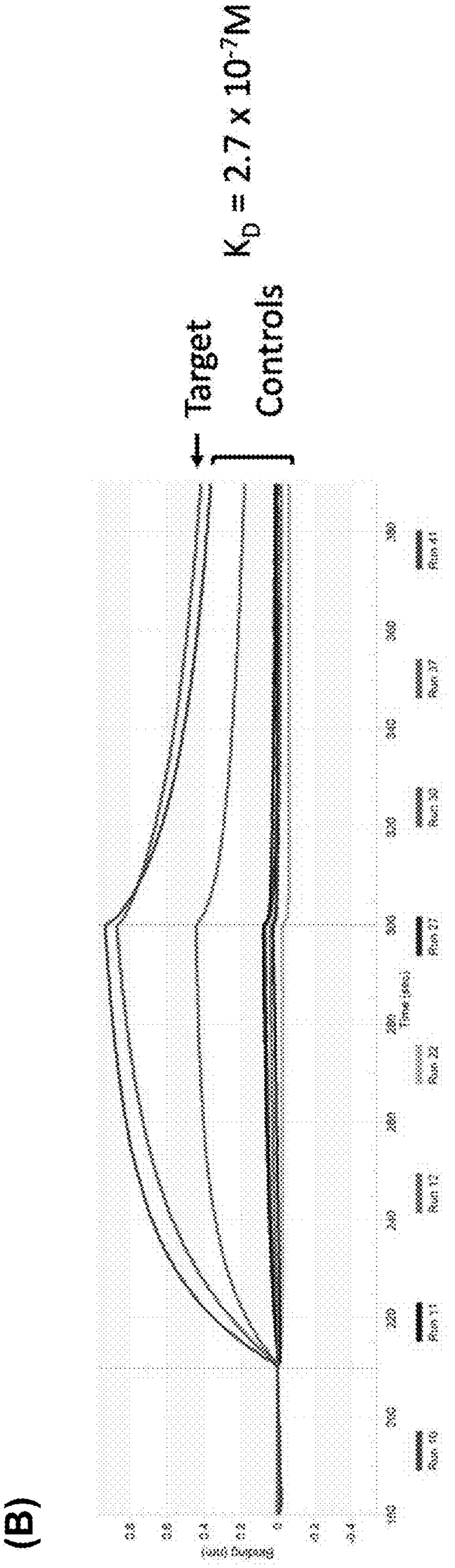
Figure 17:
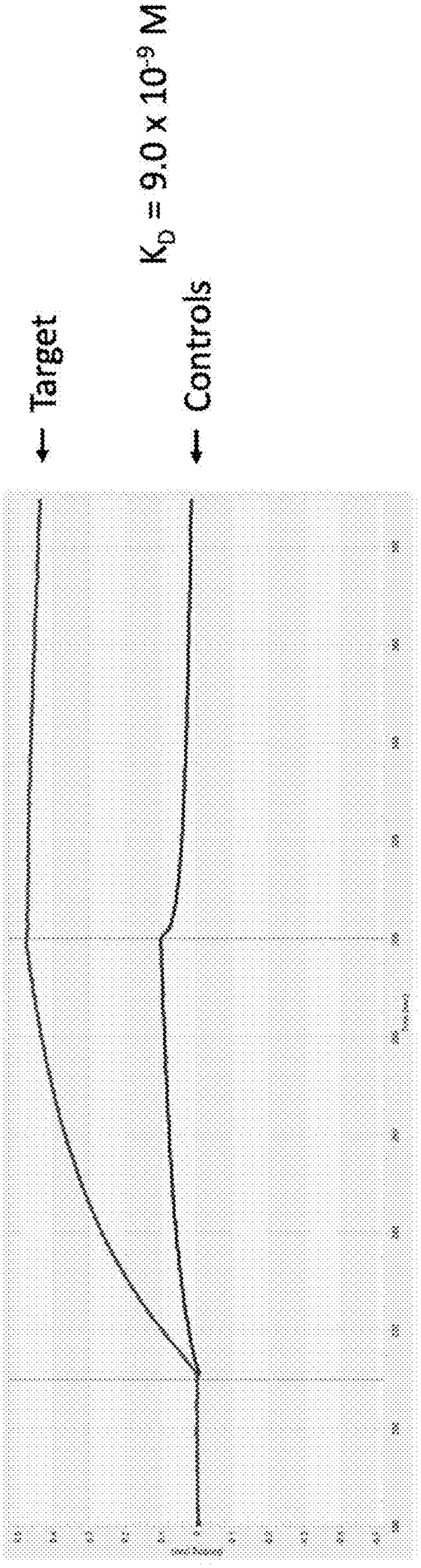
FIG. 17. Kinetic analysis of clone 1113. The figure depicts the association and dissociation of soluble PHOX2B (43-51) A*24:02 complex with scFv of clone 1113, as measured by bio-layer interferometry (BLI). The binding PHOX2B (43-51) complex (200 nM) is overlaid with a non-specific complexes (3×200 nM) control that demonstrates specific binding only to the PHOX2B (43-51) complex. Arrow labelled 'Target' shows scFv binding to the PHOX2B (43-51) MHC complex. Arrow labelled 'Controls' shows scFv binding to three pMHC complexes with unrelated peptides.
Figure 18A:
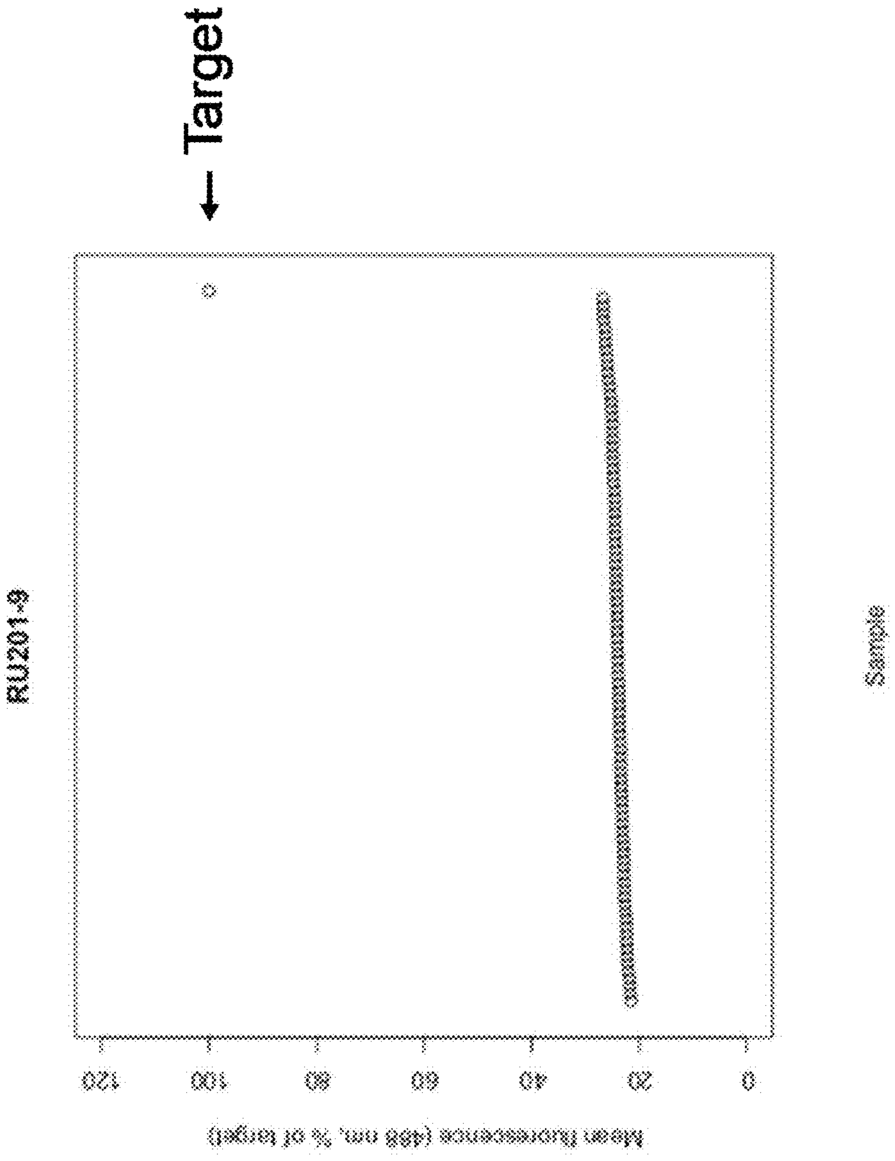
FIGS. 18A-B. Specificity array analysis of clones 9 and 1113. The figures depict bead-based binding assays demonstrating the pMHC-specificity of each scFv for the target PHOX2B (43-51) complex vs 95 unrelated complexes. The binding is normalized to the target complex (shown by arrow).
Figure 18B:
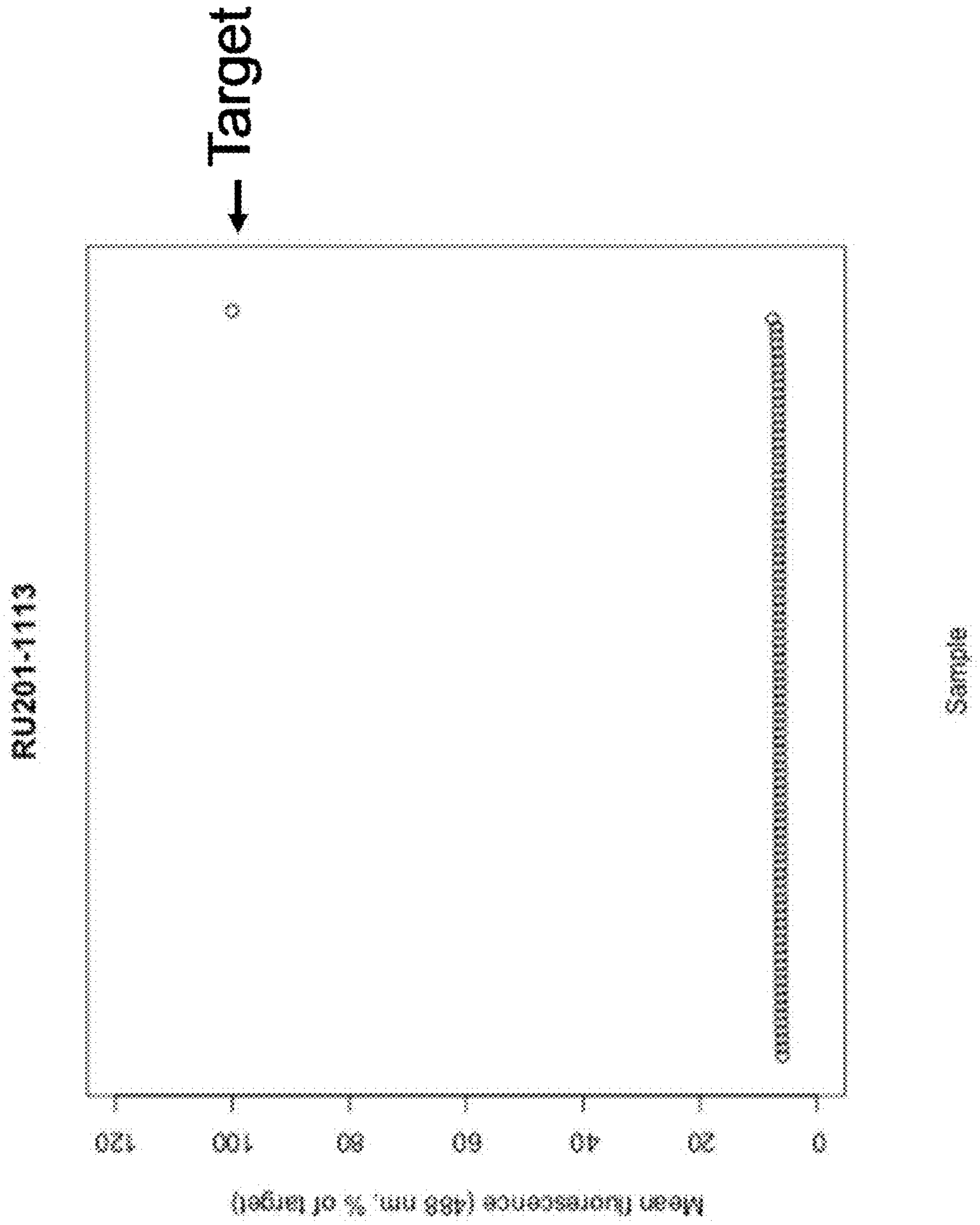
Figure 19:
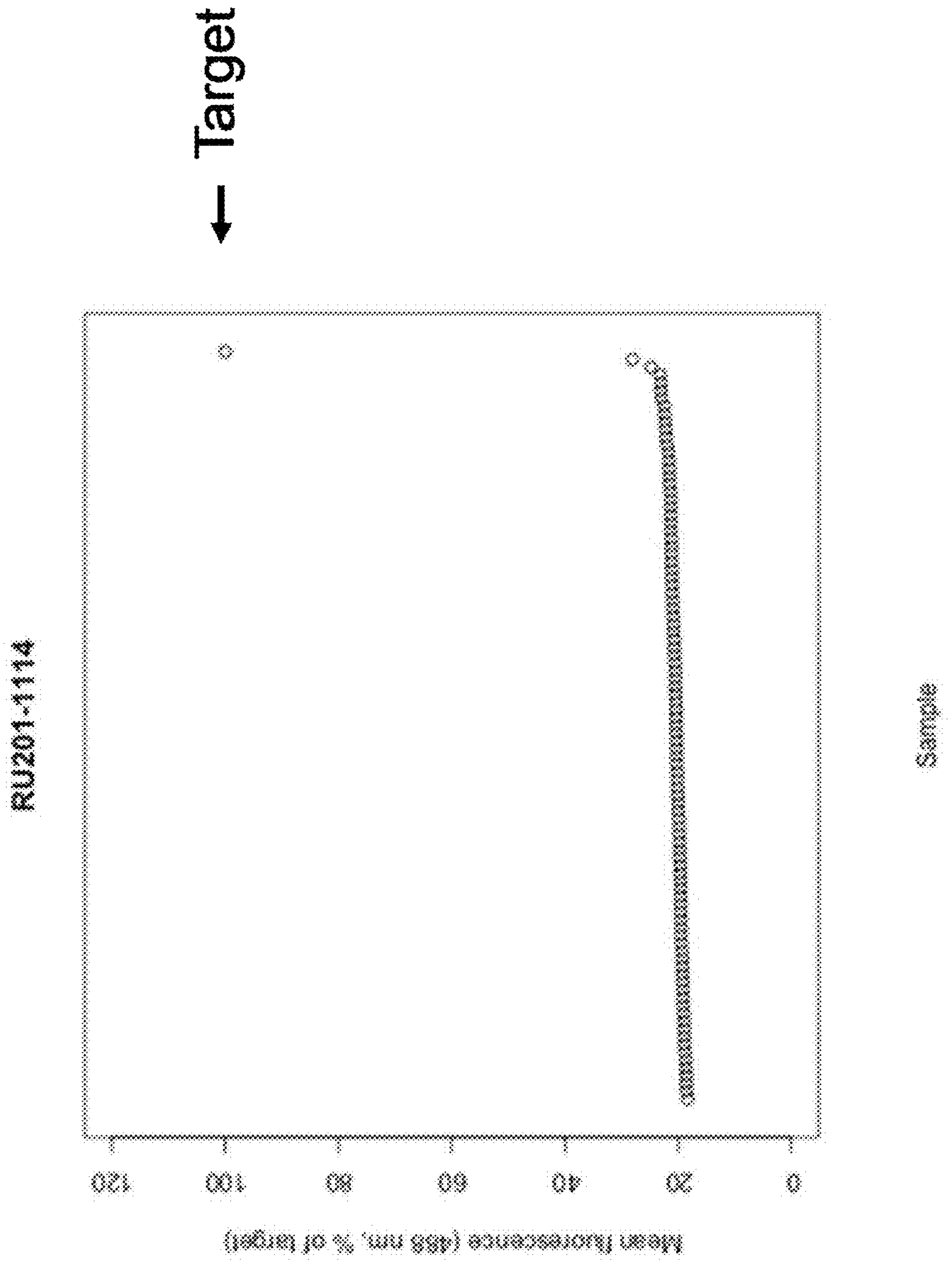
FIG. 19. Specificity array analysis of clone 1114. The figure depicts bead-based binding assays demonstrating the pMHC-specificity of clone 1114 scFv for the target PHOX2B (43-51) complex vs 95 unrelated complexes. The binding is normalized to the target complex (shown by arrow).
Figure 20A:
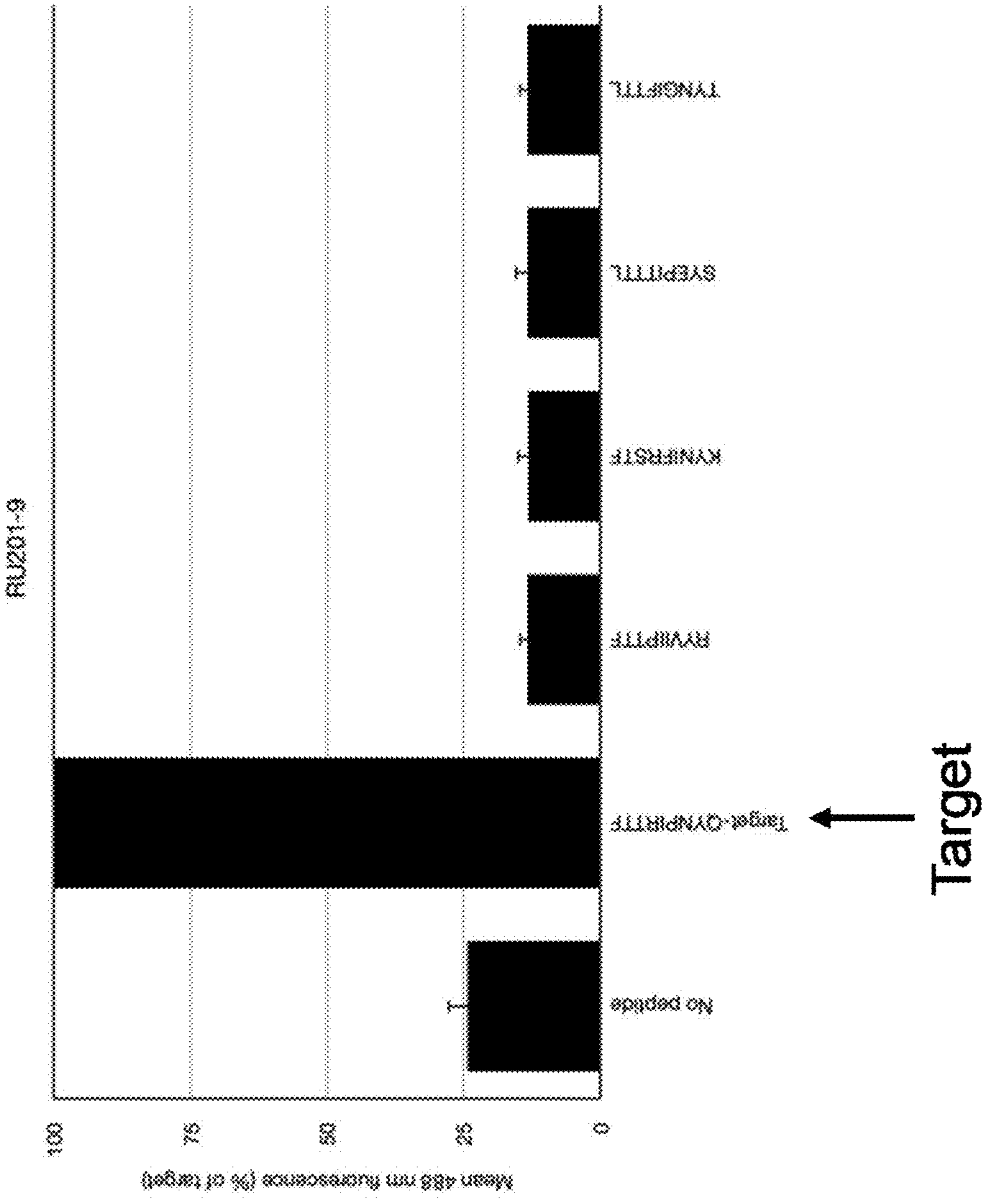
FIGS. 20A-B. Cross-reactivity analysis of clones 9 and 1113 to homologous peptides. The figures depict bead-based binding assays demonstrating the pMHC-specificity of each scFv for the target PHOX2B (43-51) complex vs peptides from the proteome and immunopeptidome that are highly homologous to the target peptide. The binding is normalized to the target complex (shown by arrow).
Figure 20B:
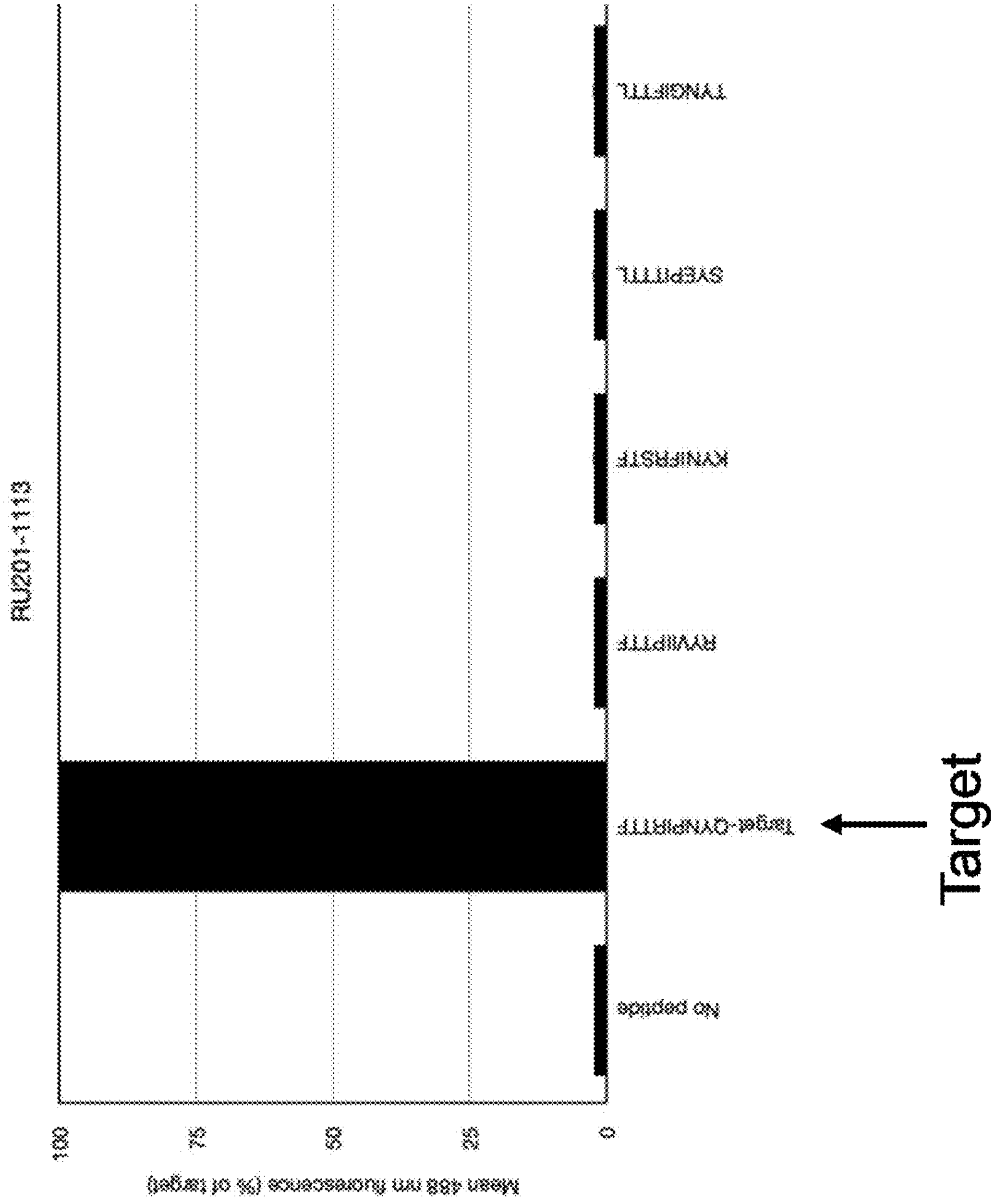
Figure 21:
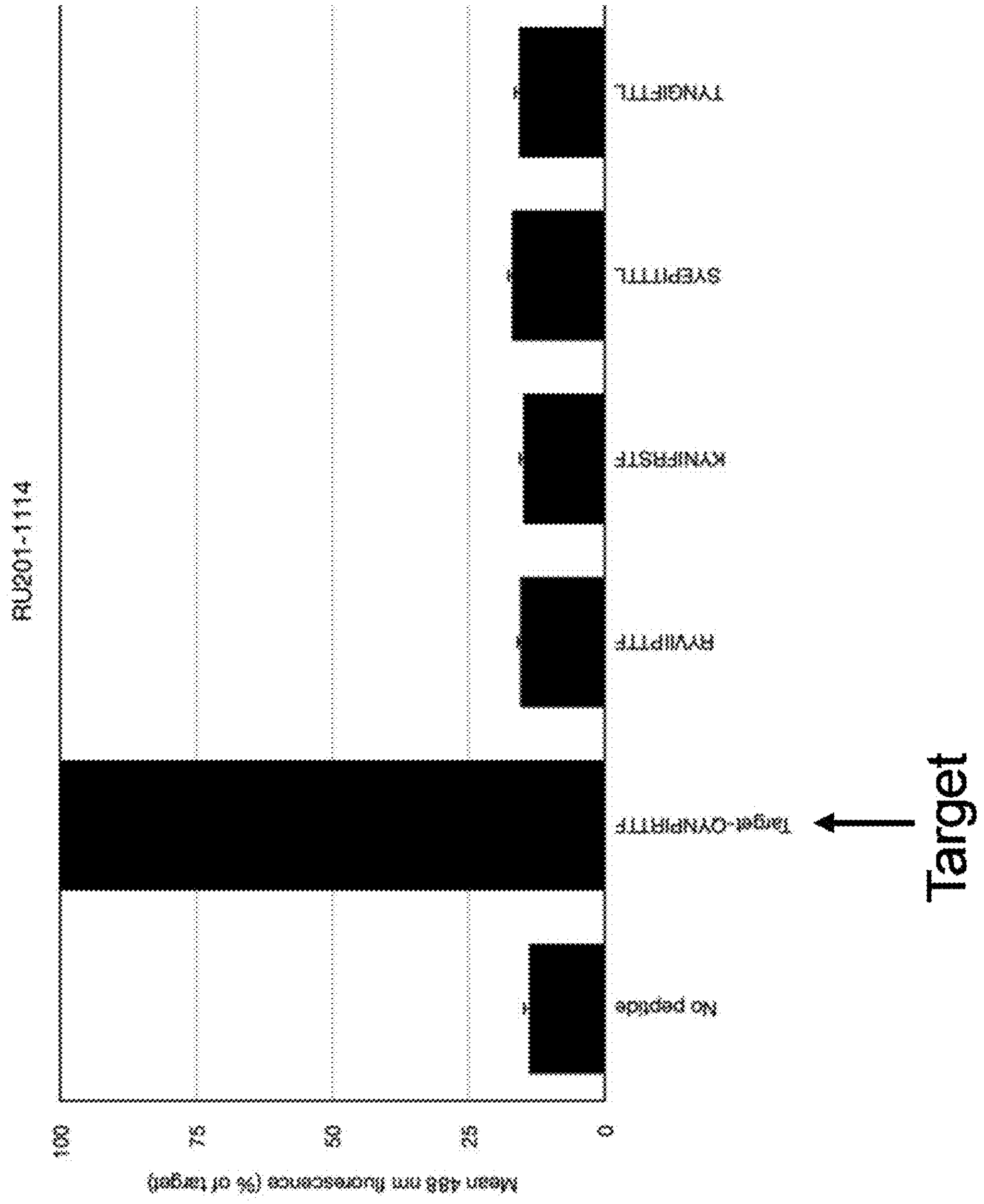
FIG. 21. Cross-reactivity analysis of clone 1114 to homologous peptides. The figure depicts bead-based binding assays demonstrating the pMHC-specificity of clone 1114 scFv for the target PHOX2B (43-51) complex vs peptides from the proteome and immunopeptidome that are highly homologous to the target peptide. The binding is normalized to the target complex (shown by arrow).

In vitro characterization of clones 9, 1113 and 1114. scFv clones 9 (SEQ ID NO: 23), 1113 (SEQ ID NO: 32) and 1114 (SEQ ID NO: 41) were also isolated from the ReD library as binding to the PHOX2B (43-51) A*24:02 MHC complex. These were characterised for their binding kinetics to the target complex by biolayer interferometry against non-target complexes (FIGS. 16A-B and FIG. 17), as well as to 95 unrelated A*24:02 MHC complexes, demonstrating specific binding to the PHOX2B target complex. They were further analysed for binding to homologous peptides, two of which, RYVIIPTTF (SEQ ID NO: 61) and KYNIFRSTF (SEQ ID NO: 62), have also been identified using mass spectrometry as presented in vivo by the immunopeptidome (world-wide-web at iedb.org) (FIGS. 20A-B and FIG. 21). To resolve the interaction between each scFv and the PHOX2B MHC complex and also to define the sensitivity of specific binding of the clones for the substitution of different amino acids at each position of the target peptide, an 'X-scan' mutagenesis of the PHOX2B target peptide sequentially mutated to 18 natural amino acids (other than cysteine) at positions 1, 3, 4, 5, 6, 7 and 8 (i.e. the non-anchor positions) was performed.

Figure 22:
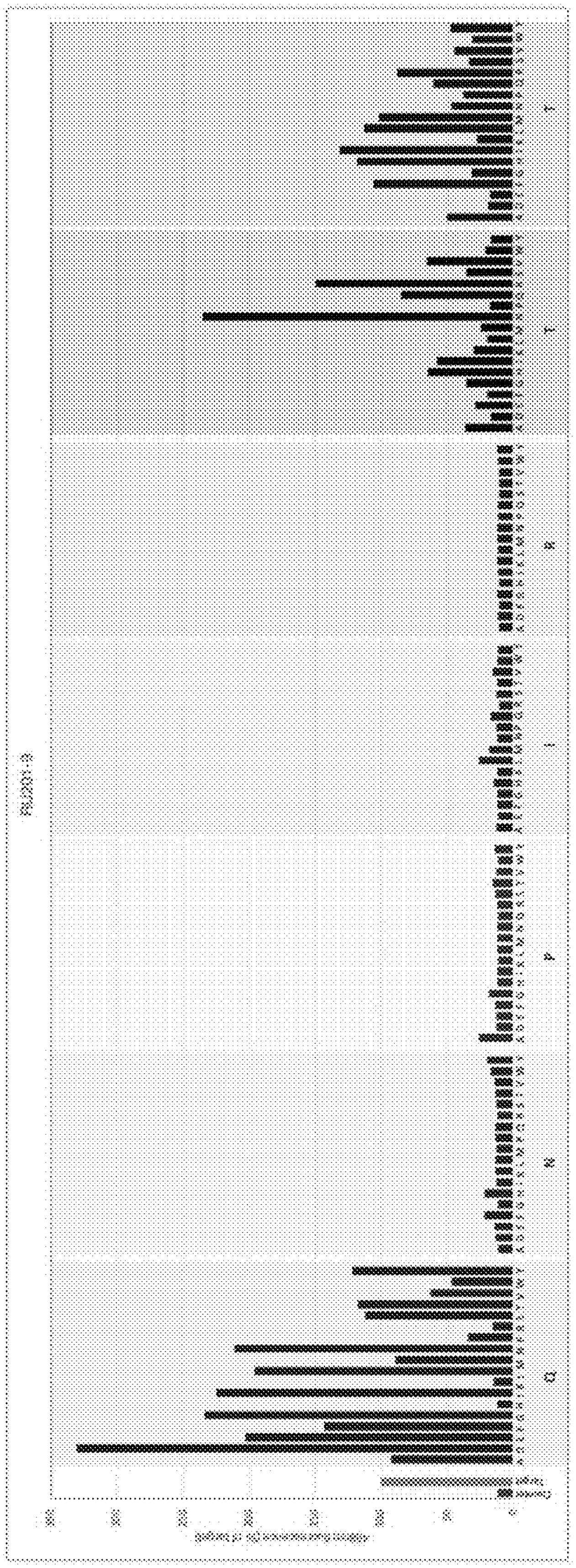
FIG. 22. Binding of PHOX2B (43-51) X-scan peptides to clone 9 scFv. The figure depicts bead-based binding assays demonstrating the binding to complexes loaded with single-residue variants of the PHOX2B (43-51) target peptide. Each non-anchor position of the target peptide was substituted for all other natural amino acids (minus cysteine) to demonstrate the tolerance of clone 9 for substitution at each position. The binding is normalized to the target and a control complex.
Figure 23:
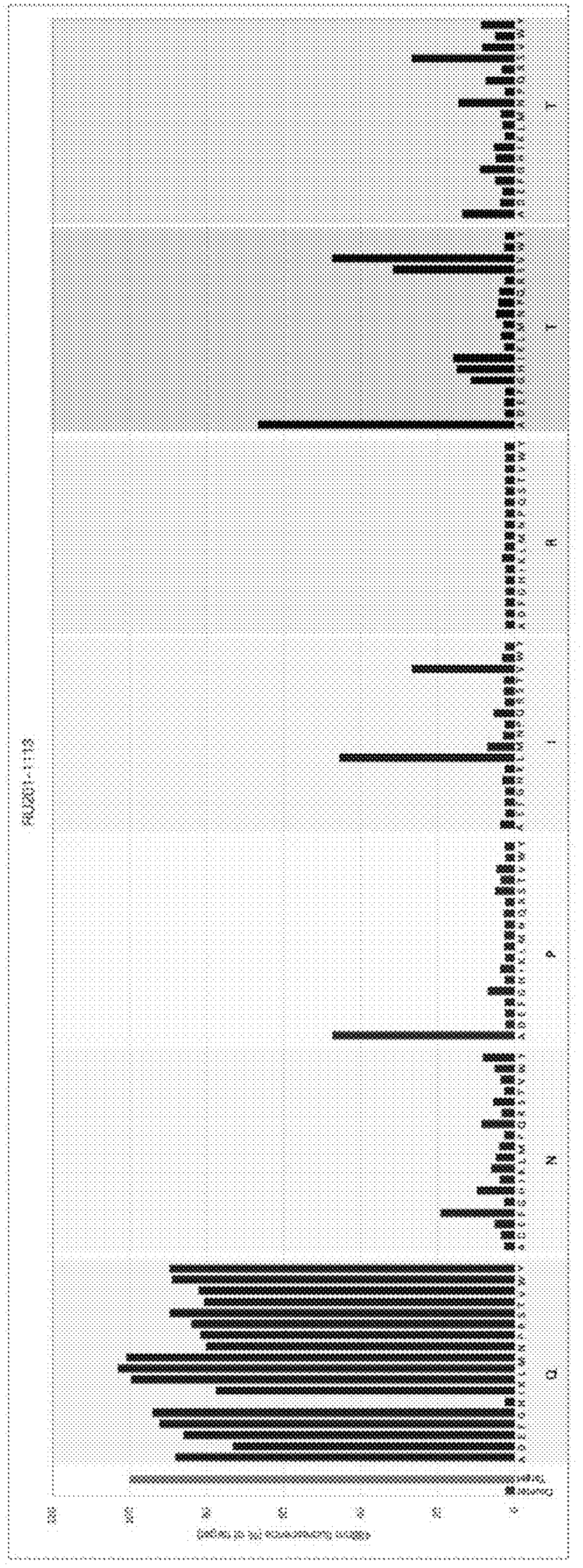
FIG. 23. Binding of PHOX2B (43-51) X-scan peptides to clone 1113 scFv. The figure depicts bead-based binding assays demonstrating the binding to complexes loaded with single-residue variants of the PHOX2B (43-51) target peptide. Each non-anchor position of the target peptide was substituted for all other natural amino acids (minus cysteine) to demonstrate the tolerance of clone 1113 for substitution at each position The binding is normalized to the target and a control complex.
Figure 24:
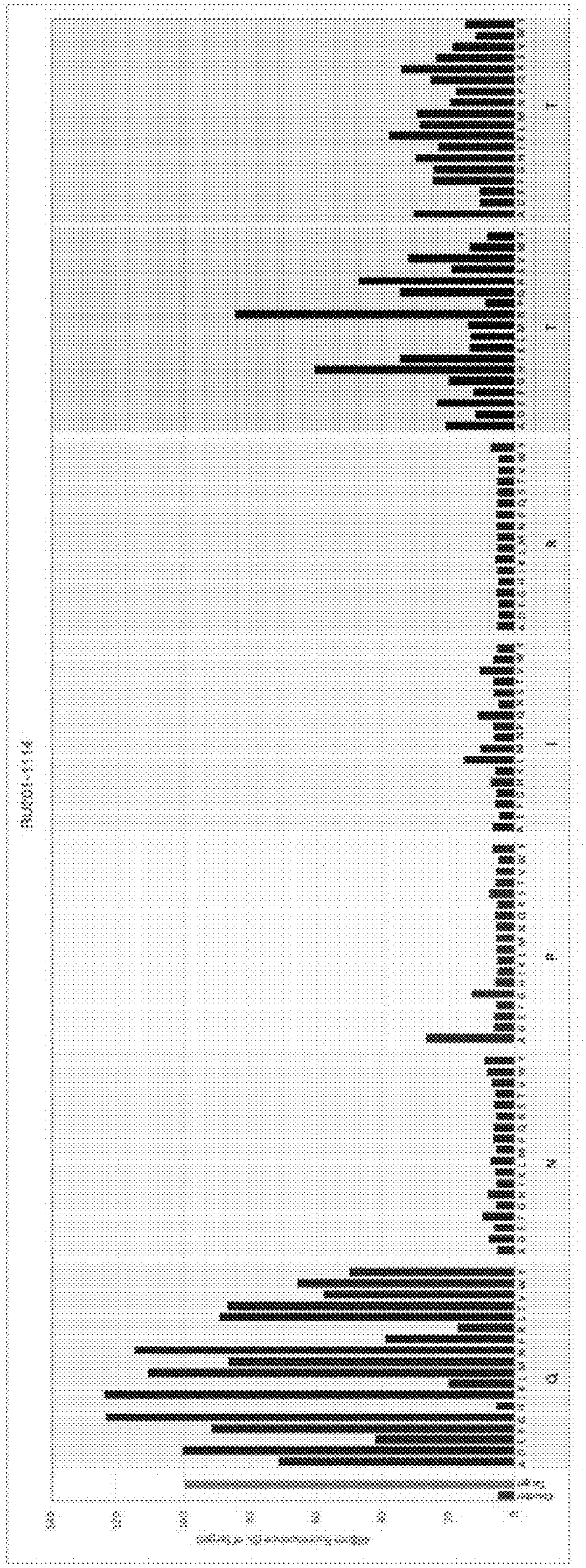
FIG. 24. Binding of PHOX2B (43-51) X-scan peptides to clone 1114 scFv. The figure depicts bead-based binding assays demonstrating the binding to complexes loaded with single-residue variants of the PHOX2B (43-51) target peptide. Each non-anchor position of the target peptide was substituted for all other natural amino acids (minus cysteine) to demonstrate the tolerance of clone 1114 for substitution at each position The binding is normalized to the target and a control complex.
Figure 27:
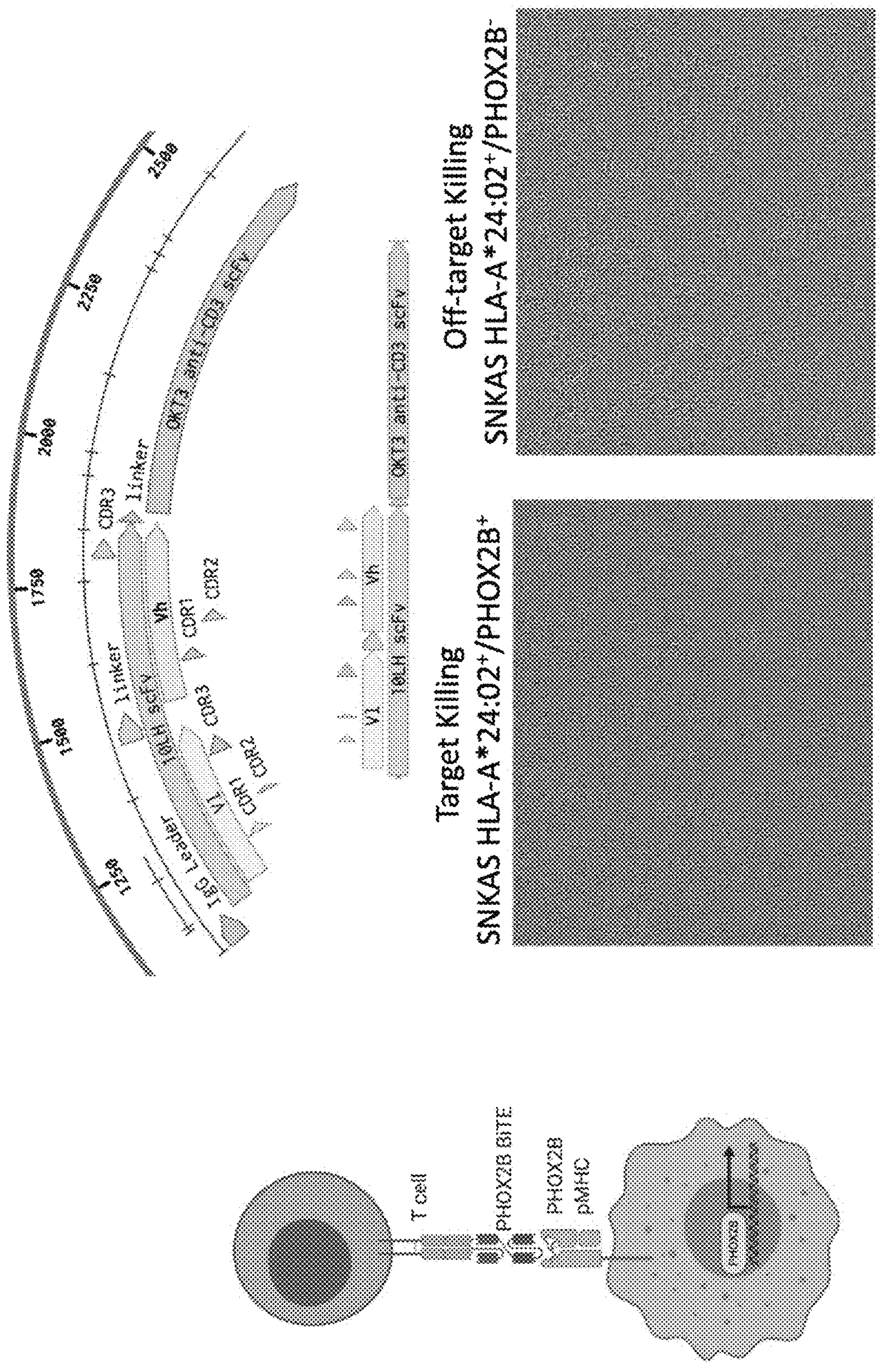
FIG. 27. 10LH BiTE data and construct design schematic. IgG leader is followed by 10LH scFv, a GDDDDKS-linker, followed by OKT3 (anti-CD3) scFv, and a 6×His tag.

FIG. 22 shows that clone 9 stringently interacts with positions 3, 4, 5 and 6, and also restricts amino acid identity at positions 1, 7 and 8 of the PHOX2B target peptide. FIG. 23 shows that clone 1113 stringently interacts with positions 3, 4, 5, 6, 7 and 8 of the target peptide. FIG. 24 shows that clone 1114 stringently interacts with positions 3, 4, 5, and 6 of the target peptide and also restricts binding identity at positions 7 and 8.

Sequence homology between CDR3 of clones 9 and 1114 establishes a binding motif. FIGS. 22 and 24 demonstrate that clones 9 and 1114 show a close pairwise preference for the MHC target peptide amino acid identity in the X-scans through each position. Examining the sequence of these clones shows that the light chain variable domain CDR3 loops have the same length and a consensus of QAWDS[L/I]G[V/N][N/M]TVV (SEQ ID NO: 50). Similarly, the heavy chain variable domain CDR3 loops have the same length and a consensus of ASE[A/Y][Y/T][S/N]AFDI (SEQ ID NO: 51). This CDR3 length conservation and identity, combined with the close similarity of the X-scans, shows that these clones represent two related solutions to binding the PHOX2B target with high specificity. Other binding solutions with close CDR identity may be found by CDR mutation scanning of both $V_L$ and $V_H$ domains, or diversified $V_L$ domain swapping with the $V_H$ domains of clones 9 (SEQ ID NO: 25), 10 (SEQ ID NO: 5), 302 (SEQ ID NO: 14), 1113 (SEQ ID NO: 34) and 1114 (SEQ ID NO: 43), with methods known to the art and described above.

Figure 28:
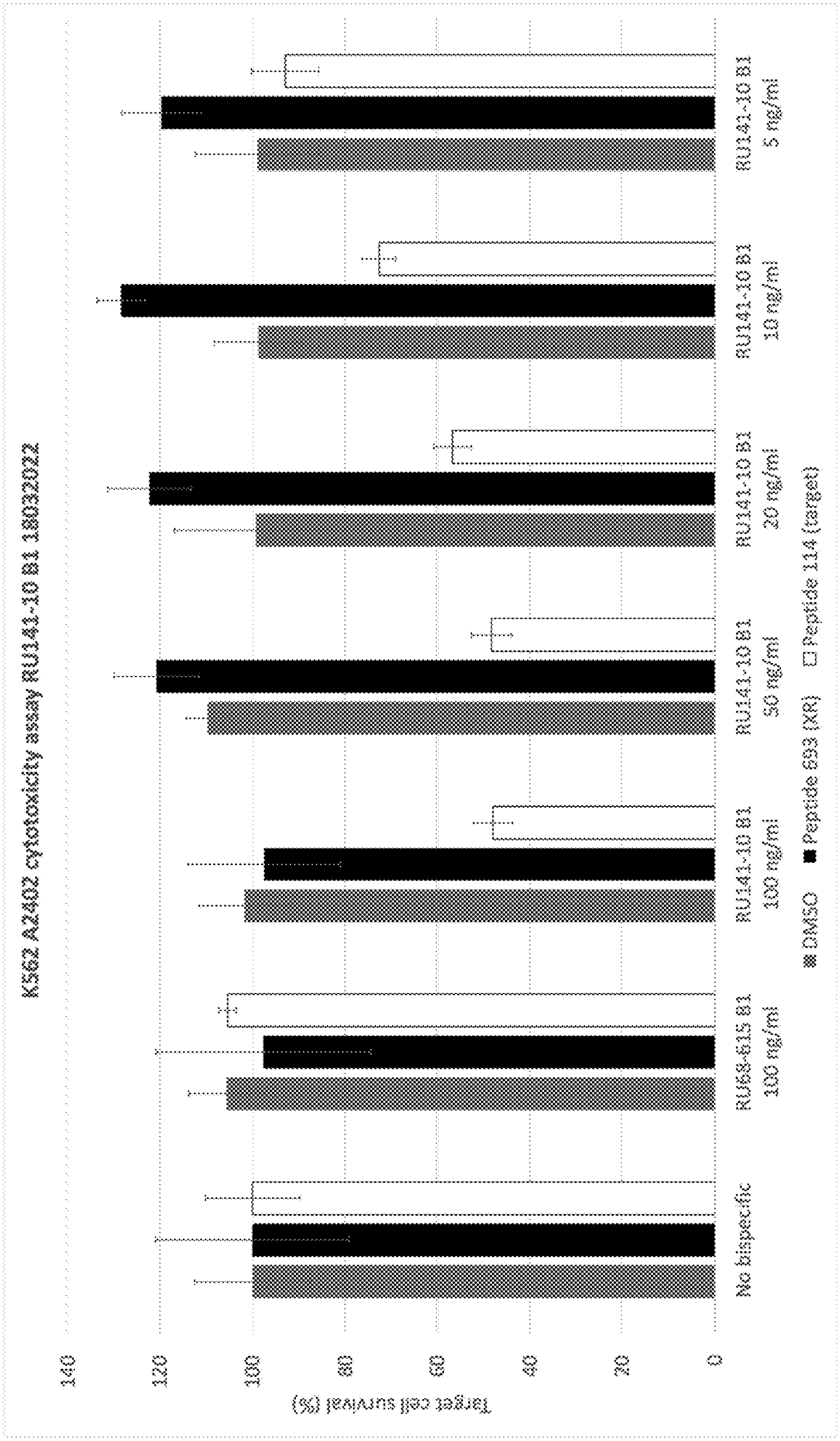
FIG. 28. PHOX2B-specific bispecific antibody mediated cytotoxicity of HLA-A*24:02 expressing cell lines in vitro. Demonstrates that clone 10 induces specific killing of K562 HLA-A*24:02 stably transfected cells treated with exogenous PHOX2B target peptide (white bar), but not irrelevant peptide (black bar) or DMSO negative control (grey bar) treated conditions. Cytotoxicity was quantitated by loss of GFP-expressing target cells.

In vitro characterization of bispecific antibody. FIG. 28 demonstrates cytotoxicity of clone 10 against K562 cells stably transfected with human HLA-A*24:02 expression construct treated with PHOX2B target peptide (114) at a concentration of 1 μM but not a equivalent concentration of a closely related irrelevant peptide (693 XR, RYVIIPTTF (SEQ ID NO: 61)) or an equivalent volume of dimethyl sulfoxide (DMSO, negative control). The cytotoxicity was measured by incubating K562 cells with peptide for 3 hours at 28° C., the K562 cells were incubated with activated human primary $CD3^+$ T cells (effectors) with or without purified bispecific antibody of clone 10 (RU141-10) at concentrations 100 ng/ml, 50 ng/ml, 20 ng/ml, 10 ng/ml and 5 ng/ml, or 100 ng/ml of irrelevant (RU68-615) bispecific control antibody. Effector and target cells were incubated at a ratio of 3:1, respectively. After 24 hours of co-incubation at 37° C., surviving K562 target cells were quantified by flow cytometry and relative percentage of surviving cells calculated by reference to experiments lacking bispecific antibodies. No cytotoxicity was observed for conditions with the no bispecific control or the RU86-615 irrelevant bispecific control when incubated with either PHOX2B target peptide (114), irrelevant peptide (693 XR, RYVIIPTTF (SEQ ID NO: 61)) or DMSO (negative control).

Figure 29A:
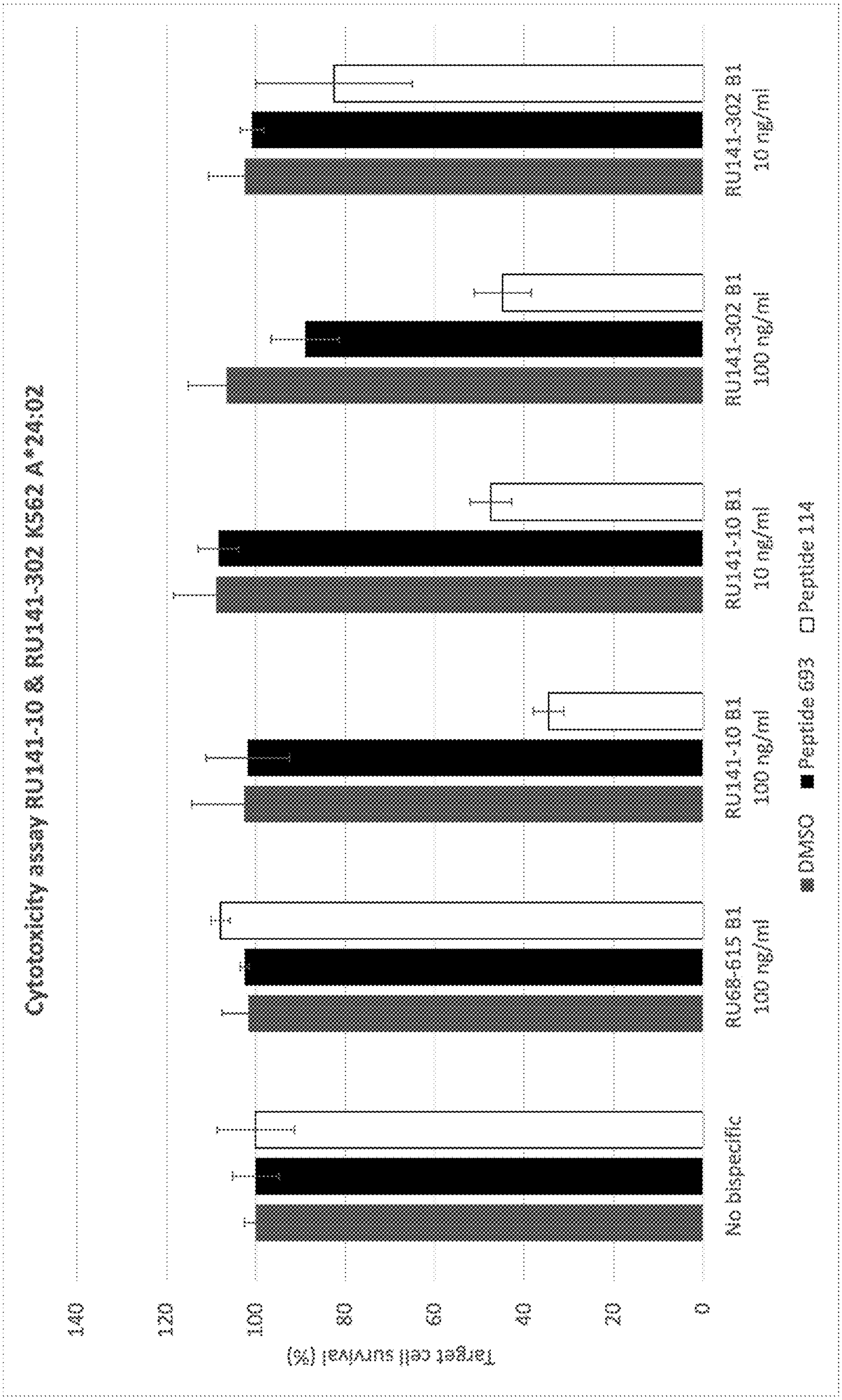
FIG. 29A. demonstrates that clone 10 and clone 302 induces specific killing of K562 HLA-A*24:02 stably transfected cells treated with exogenous PHOX2B target peptide (white bar), but not irrelevant peptide (black bar) or DMSO negative control (grey bar) treated conditions.
Figure 29B:
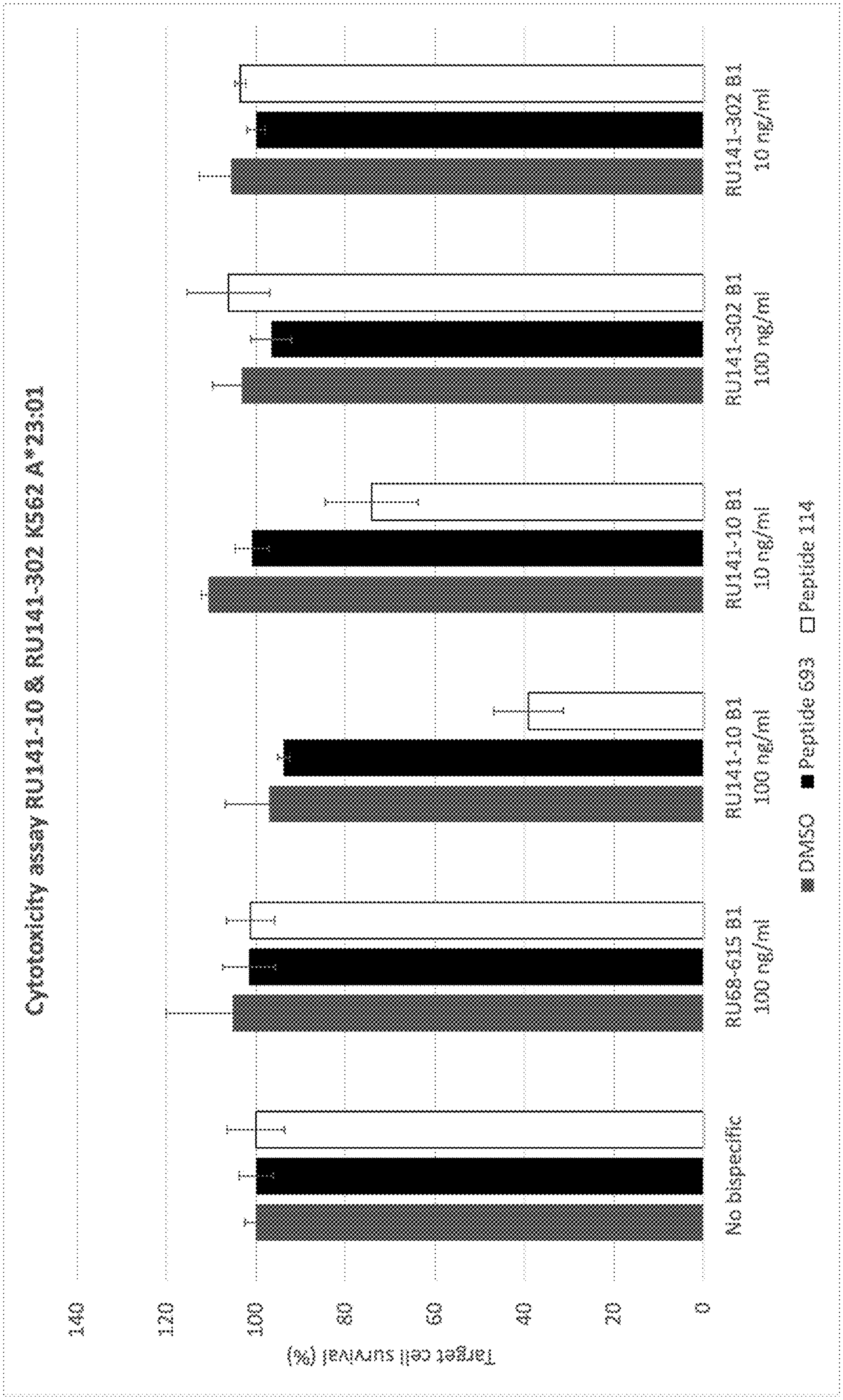
FIG. 29B. demonstrates that clone 10 but not clone 302 induces specific killing of K562 HLA-A*23:01 stably transfected cells treated with exogenous PHOX2B target peptide (white bar), but not irrelevant peptide (black bar) or DMSO negative control (grey bar) treated conditions. Cytotoxicity was quantitated by loss of GFP-expressing target cells.

FIG. 29 compares cytotoxicity of clone 10 and 302 against K562 cells stably transfected with human HLA-A*24:02 (FIG. 29A) or human HLA-A*23:01 (FIG. 29B) expression construct treated with either closely related irrelevant peptide (693 XR, RYVIIPTTF (SEQ ID NO: 61)) or PHOX2B target peptide (114) at a concentration of 1 μM, or an equivalent volume of dimethyl sulfoxide (DMSO, negative control). Following incubation of the K562 cells with peptide for 3 hours at 28° C., the K562 cells were incubated with activated human primary $CD3^+$ T cells (effectors) with or without purified bispecific antibody clone 10 (RU141-10) at concentration 100 ng/ml or 10 ng/ml, clone 302 (RU141-302) at concentration 100 ng/ml or 10 ng/ml, and irrelevant (RU68-615) bispecific control antibody at a concentration of 100 ng/ml. Effector and target cells were incubated at a ratio of 3:1, respectively. After 24 hours of co-incubation at 37° C., surviving K562 target cells were quantified by flow cytometry and relative percentage of surviving cells calculated by reference to experiments lacking bispecific antibodies.

Referring to FIG. 29, cytotoxicity was clearly observed under the conditions where bispecific clone 10 (RU141-10) at concentrations 100 ng/ml and 10 ng/ml, and bispecific clone 302 (RU141-302) at concentration 100 ng/ml, were incubated with stably transfected K562 cells expressing human HLA-A*24:02 pulsed with PHOX2B target peptide (114). In contrast, cytotoxicity was only observed for bispecific clone 10 (RU141-10) at concentrations 100 ng/ml and 10 ng/ml and not bispecific clone 302 (RU141-302) at concentrations 100 ng/ml and 10 ng/ml, when incubated with stably transfected K562 cells expressing human HLA-A*23:01 pulsed with PHOX2B target peptide (114). No cytotoxicity was observed for conditions with the no bispecific control or the RU86-615 irrelevant bispecific control when incubated with either PHOX2B target peptide (114), irrelevant peptide (693 XR, RYVIIPTTF (SEQ ID NO: 61)) or DMSO (negative control) with stably transfected K562 cells expressing human HLA-A*23:01 or stably transfected K562 cells expressing human HLA-A*24:02.

TABLE 1

Sequences of exemplary antigen-binding proteins

| Name | SEQ ID NO: | Sequence |
|---|---|---|
| PHOX2B peptide | 1 | QYNPIRTTF |
| PHOX2B | 2 | MYKMEYSYLNSSAYESCMAGMDTSSLASAYADFSS CSQASGFQYNPIRTTFGATSGCPSLTPGSCSLGTLRDH QSSPYAAVPYKLFTDHGGLNEKRKQRRIRTTFTSAQL KELERVFAETHYPDIYTREELALKIDLTEARVQVWFQ NRRAKFRKQERAAAAAAAAAKNGSSGKKSDSSRDD ESKEAKSTDPDSTGGPGPNPNPTPSCGANGGGGGGPS PAGAPGAAGPGGPGGEPGKGGAAAAAAAAAAAAA AAAAAAAGGLAAAGGPGQGWAPGPGPITSIPDSLGG PFASVLSSLQRPNGAKAALVKSSMF |
| Clone 10 (RU141-10) scFv | 3 | SRNGGDGQSVLTQPPSVSVSPGQTASITCSGDSLGNK YACWYQQKPGQSPVLVIYQDSKRPSGIPERFSGSNSG NTATLTISGTQAMDEADYYCQAWDSSRGYTVVFGT GTKVTVSSQTGGSGGGGSGGGGSGGGGSEVQLLESG GGLVQPGGSLRLSCAASGFTFDSYAMSWVRQAPGK GLEWVSAISGYGGSTYYADSVKGRFTISRDNSKNTL YLQMNSLRAEDTAVYYCAKYTYFLDAFDIWGQGTM VTVSSS |
| Clone 10 (RU141-10) scFv VL | 4 | QSVLTQPPSVSVSPGQTASITCSGDSLGNKYACWYQ QKPGQSPVLVIYQDSKRPSGIPERFSGSNSGNTATLTI SGTQAMDEADYYCQAWDSSRGYTVVFGTGTKVTV |
| Clone 10 (RU141-10) scFv VH | 5 | EVQLLESGGGLVQPGGSLRLSCAASGFTFDSYAMSW VRQAPGKGLEWVSAISGYGGSTYYADSVKGRFTISR DNSKNTLYLQMNSLRAEDTAVYYCAKYTYFLDAFDI WGQGTMVTVSS |
| Clone 10LH (Clone 10) VL CDR1 | 6 | DSLGNKY |
| Clone 10LH VL (Clone 10) CDR2 | 7 | QDSKRPS |
| Clone 10LH (Clone 10) VL CDR3 | 8 | QAWDSSRGYTVV |
| Clone 10LH (Clone 10) VH CDR1 | 9 | GFTFDSYA |
| Clone 10LH (Clone 10) VH CDR2 | 10 | SGYGGS |
| Clone 10LH (Clone 10) VH CDR3 | 11 | YTYFLDAFD |
| Clone 302 (RU141-302) scFv | 12 | SRNGGDGQSVLTQPPSVSVSPGQTASITCSGDKLGDK YACWYQQKPGQSPVLVIYQDSKRPSGIPERFSGSNSG NTATLTISGTQAMDEADYYCQAWDMVGSWTVVFG TGTKVTVSSQTGGSGGGGSGGGGSGGGGSEVQLLES GGGLVQPGGSLRLSCAASGFTFSSYAMSWVRQAPGK GLEWVSAISGSGGSTYYADSVKGRFTISRDNSKNTLY LQMNSLRAEDTAVYYCAKPRFDGQWDNAFDIWGQ GTMVTVSSS |

TABLE 1-continued

| Sequences of exemplary antigen-binding proteins | | |
|---|---|---|
| Name | SEQ ID NO: | Sequence |
| Clone 302 (RU141-302) VL | 13 | QSVLTQPPSVSVSPGQTASITCSGDKLGDKYACWYQ QKPGQSPVLVIYQDSKRPSGIPERFSGSNSGNTATLTI SGTQAMDEADYYCQAWDMVGSWTVVFGTGTKVTV |
| Clone 302 (RU141-302) VH | 14 | EVQLLESGGGLVQPGGSLRLSCAASGFTFSSYAMSW VRQAPGKGLEWVSAISGSGGSTYYADSVKGRFTISR DNSKNTLYLQMNSLRAEDTAVYYCAKPRFDGQWDN AFDIWGQGTMVTVSS |
| Clone 302LH VL CDR1 | 15 | DKLGDKY |
| Clone 302LH VL CDR2 | 16 | QDSKRPS |
| Clone 302LH VL CDR3 | 17 | QAWDMVGSWTVV |
| Clone 302LH VH CDR1 | 18 | GFTFSSY |
| Clone 302LH VH CDR2 | 19 | SGSGGS |
| Clone 302LH VH CDR3 | 20 | PRFDGQWDNAFDI |
| PHOX2B 10LH PC-CAR 4-1bb/CD3z | 21 | MALPVTALLLPLALLLHAARPSRNGGDGQSVLTQPP SVSVSPGQTASITCSGDSLGNKYACWYQQKPGQSPV LVIYQDSKRPSGIPERFSGSNSGNTATLTISGTQAMDE ADYYCQAWDSSRGYTVVFGTGTKVTVSSQTGGSGG GGSGGGGSGGGGSEVQLLESGGGLVQPGGSLRLSCA ASGFTFDSYAMSWVRQAPGKGLEWVSAISGYGGST YYADSVKGRFTISRDNSKNTLYLQMNSLRAEDTAVY YCAKYTYFLDAFDIWGQGTMVTVSSSSTTTPAPRPPT PAPTIASQPLSLRPEACRPAAGGAVHTRGLDFACDIYI WAPLAGTCGVLLLSLVITLYCKRGRKKLLYIFKQPFM RPVQTTQEEDGCSCRFPEEEEGGCELRVKFSRSADAP AYKQGQNQLYNELNLGRREEYDVLDKRRGRDPEMG GKPRRKNPQEGLYNELQKDKMAEAYSEIGMKGERR RGKGHDGLYQGLSTATKDTYDALHMQALPPR |
| PHOX2B 302LH PC-CAR 4-1bb/CD3z | 22 | MALPVTALLLPLALLLHAARPSRNGGDGQSVLTQPP SVSVSPGQTASITCSGDKLGDKYACWYQQKPGQSPV LVIYQDSKRPSGIPERFSGSNSGNTATLTISGTQAMDE ADYYCQAWDMVGSWTVVFGTGTKVTVSSQTGGSG GGGSGGGGSGGGGSEVQLLESGGGLVQPGGSLRLSC AASGFTFSSYAMSWVRQAPGKGLEWVSAISGSGGST YYADSVKGRFTISRDNSKNTLYLQMNSLRAEDTAVY YCAKPRFDGQWDNAFDIWGQGTMVTVSSSTTTPAPR PPTPAPTIASQPLSLRPEACRPAAGGAVHTRGLDFAC DIYIWAPLAGTCGVLLLSLVITLYCKRGRKKLLYIFK QPFMRPVQTTQEEDGCSCRFPEEEEGGCELRVKFSRS ADAPAYKQGQNQLYNELNLGRREEYDVLDKRRGRD PEMGGKPRRKNPQEGLYNELQKDKMAEAYSEIGMK GERRRGKGHDGLYQGLSTATKDTYDALHMQALPPR |
| Clone 9 (RU-201-9) scFv | 23 | SRNGGDGQSVLTQPPSVSVSPGQTASITCSGDSLGYK YACWYQQKPGQSPVLVIYQDSKRPSGIPERFSGSNSG NTATLTISGTQAMDEADYYCQAWDSLGVNTVVFGT GTKVTVSSQTGGSGGGGSGGGGSGGGGSEVQLLESG GGLVQPGGSLRLSCAASGFTFNYYAMSWVRQAPGK GLEWVSAISGYGGSTYYADSVKGRFTISRDNSKNTL YLQMNSLRAEDTAVYYCAKASEAYSAFDIWGQGTM VTVSSS |
| Clone 9 (RU-201-9) VL | 24 | QSVLTQPPSVSVSPGQTASITCSGDSLGYKYACWYQ QKPGQSPVLVIYQDSKRPSGIPERFSGSNSGNTATLTI SGTQAMDEADYYCQAWDSLGVNTVVFGTGTKVTV |
| Clone 9 (RU-201-9) VH | 25 | EVQLLESGGGLVQPGGSLRLSCAASGFTFNYYAMSW VRQAPGKGLEWVSAISGYGGSTYYADSVKGRFTISR DNSKNTLYLQMNSLRAEDTAVYYCAKASEAYSAFDI WGQGTMVTVSS |

TABLE 1-continued

| Sequences of exemplary antigen-binding proteins | | |
|---|---|---|
| Name | SEQ ID NO: | Sequence |
| Clone 9 VL CDR1 | 26 | DSLGYKY |
| Clone 9 VL CDR2 | 27 | QDSKRPS |
| Clone 9 VL CDR3 | 28 | QAWDSLGVNTVV |
| Clone 9 VH CDR1 | 29 | GFTFNYYA |
| Clone 9 VH CDR2 | 30 | SGYGGS |
| Clone 9 VH CDR3 | 31 | ASEAYSAFDI |
| Clone 1113 (RU-201-1113) scFv | 32 | SRNGGDGQSVLTQPPSVSAAPGQKVTISCSGSSSNIG NNYVSWYQQLPGTAPKLLIYDNNKRPSGIPDRESGSK SGTSATLGITGLQTGDEADYYCGTWDHMGRNTVVF GTGTKVTVSSQTGGSGGGGSGGGGSGGGGSEVQLLE SGGGLVQPGGSLRLSCAASGFTFSDYAMSWVRQAPG KGLEWVSAISGTGGSTYYADSVKGRFTISRDNSKNTL YLQMNSLRAEDTAVYYCAKEFSVVNSAAFDIWGQG TMVTVSSS |
| Clone 1113 (RU-201-1113) VL | 33 | QSVLTQPPSVSAAPGQKVTISCSGSSSNIGNNYVSWY QQLPGTAPKLLIYDNNKRPSGIPDRESGSKSGTSATLG ITGLQTGDEADYYCGTWDHMGRNTVVFGTGTKVTV |
| Clone 1113 (RU-201-1113) VH | 34 | EVQLLESGGGLVQPGGSLRLSCAASGFTFSDYAMSW VRQAPGKGLEWVSAISGTGGSTYYADSVKGRFTISR DNSKNTLYLQMNSLRAEDTAVYYCAKEFSVVNSAA FDIWGQGTMVTVSS |
| Clone 1113 VL CDR1 | 35 | SSNIGNNY |
| Clone 1113 VL CDR2 | 36 | DNNKRPS |
| Clone 1113 VL CDR3 | 37 | GTWDHMGRNTVV |
| Clone 1113 VH CDR1 | 38 | GFTFSDYA |
| Clone 1113 VH CDR2 | 39 | SGTGGS |
| Clone 1113 VH CDR3 | 40 | EFSVVNSAAFDI |
| Clone 1114 (RU201-1114) scFv | 41 | SRNGGDGQSVLTQPPSVSVSPGQTASITCSGDKLGDK YACWYQQKPGQSPVLVIYQDSKRPSGIPERFSGSNSG NTATLTISGTQAMDEADYYCQAWDSIGNMTVVFGT GTKVTVSSQTGGSGGGGSGGGGSGGGGSEVQLLESG GGLVQPGGSLRLSCAASGFTFDYYAMSWVRQAPGK GLEWVSAISGYGGSTYYADSVKGRFTISRDNSKNTL YLQMNSLRAEDTAVYYCAKASEYT NAFDIWGQGIMVTVSSS |
| Clone 1114 (RU201-1114VL | 42 | QSVLTQPPSVSVSPGQTASITCSGDKLGDKYACWYQ QKPGQSPVLVIYQDSKRPSGIPERFSGSNSGNTATLTI SGTQAMDEADYYCQAWDSIGNMTVVFGTGTKVTV |
| Clone 1114 (RU201-1114VH | 43 | EVQLLESGGGLVQPGGSLRLSCAASGFTFDYYAMSW VRQAPGKGLEWVSAISGYGGSTYYADSVKGRFTISR DNSKNTLYLQMNSLRAEDTAVYYCAKASEYTNAFDI WGQGIMVTVSS |
| Clone 1114 VL CDR1 | 44 | DKLGDKY |
| Clone 1114 VL CDR2 | 45 | QDSKRPS |
| Clone 1114 VL CDR3 | 46 | QAWDSIGNMTVV |

TABLE 1-continued

| Sequences of exemplary antigen-binding proteins | | |
|---|---|---|
| Name | SEQ ID NO: | Sequence |
| Clone 1114 VH CDR1 | 47 | GFTFDYYA |
| Clone 1114 VH CDR2 | 48 | SGYGGS |
| Clone 1114 VH CDR3 | 49 | ASEYTNAFDI |
| Clones 9 and 1114 light chain variable domain CDR3 | 50 | QAWDS[L/I]G[V/N][N/M]TVV |
| Clones 9 and 1114 heavy chain variable domain CDR3 | 51 | ASE[A/Y][Y/T][S/N]AFDI |
| Control peptide 1 | 52 | NYTPIRTTF |
| Control peptide 2 | 53 | LYNPIRTTF |
| Control peptide 3 | 54 | QYQPLRTTF |
| Control peptide 4 | 55 | QYNPIKTTF |
| Control peptide 5 | 56 | QYNPLQTTF |
| Control peptide 6 | 57 | QYNPLKTTF |
| Control peptide 7 | 58 | QYNAIRTTF |
| MAGE-A3 peptide | 59 | EVDPIGHLY |
| Titin peptide | 60 | ESDPIVAQY |
| Unrelated peptide 1 | 61 | RYVIIPTTF |
| Unrelated peptide 2 | 62 | KYNIFRSTF |
| Unrelated peptide 3 | 63 | SYEPITTTL |
| Unrelated peptide 4 | 64 | TYNGIFTTL |
| CD8 leader | 65 | MALPVTALLLPLALLLHAARP |
| 10LH $V_L$ | 66 | SRNGGDGQSVLTQPPSVSVSPGQTASITCSGDSLGNK YACWYQQKPGQSPVLVIYQDSKRPSGIPERFSGSNSG NTATLTISGTQAMDEADYYCQAWDSSRGYTVVFGT GTKVTVSSQT |
| Linker | 67 | GGSGGGGSGGGGSGGGGS |
| 10LH $V_H$ | 68 | EVQLLESGGGLVQPGGSLRLSCAASGFTFDSYAMSW VRQAPGKGLEWVSAISGYGGSTYYADSVKGRFTISR DNSKNTLYLQMNSLRAEDTAVYYCAKYTYFLDAFDI WGQGTMVTVSSSS |
| CD8 hinge | 69 | TTTPAPRPPTPAPTIASQPLSLRPEACRPAAGGAVHTR GLDFACD |
| CD8 transmembrane | 70 | IYIWAPLAGTCGVLLLSLVITLYC |
| 4-1BB | 71 | KRGRKKLLYIFKQPFMRPVQTTQEEDGCSCRFPEEEE GGCEL |
| CD3-zeta | 72 | RVKFSRSADAPAYKQGQNQLYNELNLGRREEYDVL DKRRGRDPEMGGKPRRKNPQEGLYNELQKDKMAEA YSEIGMKGERRRGKGHDGLYQGLSTATKDTYDALH MQALPPR |
| 302LH $V_L$ | 73 | SRNGGDGQSVLTQPPSVSVSPGQTASITCSGDKLGDK YACWYQQKPGQSPVLVIYQDSKRPSGIPERFSGSNSG NTATLTISGTQAMDEADYYCQAWDMVGSWTVVFG TGTKVTVSSQT |

TABLE 1-continued

Sequences of exemplary antigen-binding proteins

| Name | SEQ ID NO: | Sequence |
|---|---|---|
| 302LH $V_H$ | 74 | EVQLLESGGGLVQPGGSLRLSCAASGFTFSSYAMSW VRQAPGKGLEWVSAISGSGGSTYYADSVKGRFTISR DNSKNTLYLQMNSLRAEDTAVYYCAKPRFDGQWDN AFDIWGQGTMVTVSSS |

TABLE 2

Sequences for PHOX2B 10LH PC-CAR 4-1bb/CD3z

MALPVTALLLPLALLLHAARPSRNGGDGQSVLTQPPSVSVSPGQTASITCSGDSLGN
KYACWYQQKPGQSPVLVIYQDSKRPSGIPERFSGSNSGNTATLTISGTQAMDEADYY
CQAWDSSRGYTVVFGTGTKVTVSSQTGGSGGGGSGGGGSGGGGSEVQLLESGGGL
VQPGGSLRLSCAASGFTFDSYAMSWVRQAPGKGLEWVSAISGYGGSTYYADSVKG
RFTISRDNSKNTLYLQMNSLRAEDTAVYYCAKYTYFLDAFDIWGQGTMVTVSSSST
TTPAPRPPTPAPTIASQPLSLRPEACRPAAGGAVHTRGLDFACDIYIWAPLAGTCGVL
LLSLVITLYCKRGRKKLLYIFKQPFMRPVQTTQEEDGCSCRFPEEEEGGCELRVKFSR
SADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR*
(SEQ ID NO: 21)

Clone 10LH
CD8 leader: MALPVTALLLPLALLLHAARP (SEQ ID NO: 65)

10LH $V_L$
SRNGGDGQSVLTQPPSVSVSPGQTASITCSGDSLGNKYACWYQQKPGQSPVLVIYQ
DSKRPSGIPERFSGSNSGNTATLTISGTQAMDEADYYC*QAWDSSRGYTVV*FGTGTKV
TVSSQT (SEQ ID NO: 66)

CDR1 DSLGNKY (SEQ ID NO: 6)

CDR2 QDSKRPS (SEQ ID NO: 7)

CDR3 *QAWDSSRGYTVV* (SEQ ID NO: 8)

Linker: GGSGGGGSGGGGSGGGGS (SEQ ID NO: 67)

10LH $V_H$
EVQLLESGGGLVQPGGSLRLSCAASGFTFDSYAMSWVRQAPGKGLEWVSAISGYG
GSTYYADSVKGRFTISRDNSKNTLYLQMNSLRAEDTAVYYCAK*YTYFLDAFDI*WGQ
GTMVTVSSSS (SEQ ID NO: 68)

CDR1 GFTFDSYA (SEQ ID NO: 9)

CDR2 SGYGGS (SEQ ID NO: 10)

CDR3 *YTYFLDAFD* (SEQ ID NO: 11)

CD8 hinge:
TTTPAPRPPTPAPTIASQPLSLRPEACRPAAGGAVHTRGLDFACD (SEQ ID NO: 69)

CD8 transmembrane:
IYIWAPLAGTCGVLLLSLVITLYC (SEQ ID NO: 70)

4-1BB:
KRGRKKLLYIFKQPFMRPVQTTQEEDGCSCRFPEEEEGGCEL (SEQ ID NO: 71)

CD3-zeta:
RVKFSRSADAPAYKQGQNQLYNELNLGRREEYDVLDKRRGRDPEMGGKPRRKNPQ
EGLYNELQKDKMAEAYSEIGMKGERRRGKGHDGLYQGLSTATKDTYDALHMQAL
PPR* (SEQ ID NO: 72)

TABLE 3

| PHOX2B 302LH PC-CAR 4-1bb/CD3z |
|---|
| MALPVTALLLPLALLLHAARPSRNGGDGQSVLTQPPSVSVSPGQTASITC SGDKLGDKYACWYQQKPGQSPVLVIYQDSKRPSGIPERFSGSNSGNTATL TISGTQAMDEADYYCQAWDMVGSWTVVFGTGTKVTVSSQTGGSGGGGSGG GGSGGGGSEVQLLESGGGLVQPGGSLRLSCAASGFTFSSYAMSWVRQAPG KGLEWVSAISGSGGSTYYADSVKGRFTISRDNSKNTLYLQMNSLRAEDTA VYYCAKPRFDGQWDNAFDIWGQGTMVTVSSSTTTPAPRPPTPAPTIASQP LSLRPEACRPAAGGAVHTRGLDFACDIYIWAPLAGTCGVLLLSLVITLYC KRGRKKLLYIFKQPFMRPVQTTQEEDGCSCRFPEEEEGGCELRVKFSRSA DAPAYKQGQNQLYNELNLGRREEYDVLDKRRGRDPEMGGKPRRKNPQEGL YNELQKDKMAEAYSEIGMKGERRRGKGHDGLYQGLSTATKDTYDALHMQA LPPR* (SEQ ID NO: 22) |
| CD8 leader: |
| MALPVTALLLPLALLLHAARP (SEQ ID NO: 65) |
| 302LH $V_L$ |
| SRNGGDGQSVLTQPPSVSVSPGQTASITCSG**DKLGDKY** ACWYQQKPGQSPVLVIY**QDSKRPS**GIPERFSGSNSGNT ATLTISGTQAMDEADYYC***QAWDMVGSWTVV***FGTGTK VTVSSQT (SEQ ID NO: 73) |
| **CDR1 DKLGDKY** (SEQ ID NO: 15) |
| **CDR2 QDSKRPS** (SEQ ID NO: 16) |
| ***CDR3 QAWDMVGSWTVV*** (SEQ ID NO: 17) |
| Linker: GGSGGGGSGGGGSGGGGS (SEQ ID NO: 67) |
| 302LH $V_H$ |
| EVQLLESGGGLVQPGGSLRLSCAAS**GFTFSSY** AMSWVRQAPGKGLEWVSAI**SGSGGS**TYYADSV KGRFTISRDNSKNTLYLQMNSLRAEDTAVYYC AK***PRFDGQWDNAFDI***WGQGTMVTVSSS (SEQ ID NO: 74) |
| **CDR1 GFTFSSY** (SEQ ID NO: 18) |
| **CDR2 SGSGGS** (SEQ ID NO: 19) |
| ***CDR3 PRFDGQWDNAFDI*** (SEQ ID NO: 20) |
| CD8 hinge: |
| TTTPAPRPPTPAPTIASQPLSLRPEACRPAAGGAVHTRGLDFACD (SEQ ID NO: 69) |
| CD8 transmembrane: |
| IYIWAPLAGTCGVLLLSLVITLYC (SEQ ID NO: 70) |
| 4-1BB: |
| KRGRKKLLYIFKQPFMRPVQTTQEEDGCSCRFPEEEEGGCEL (SEQ ID NO: 71) |
| CD3-zeta: |
| RVKFSRSADAPAYKQGQNQLYNELNLGRREEYDVLDKRRGRDPEMGGKPR RKNPQEGLYNELQKDKMAEAYSEIGMKGERRRGKGHDGLYQGLSTATKDT YDALHMQALPPR (SEQ ID NO: 72)* |

All of the compositions and methods disclosed and claimed herein can be made and executed without undue experimentation in light of the present disclosure. While the compositions and methods of this disclosure have been described in terms of particular embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

IX. References

The following references and any other reference cited herein, to the extent that they provide exemplary procedural or other details supplementary to those set forth herein, are specifically incorporated herein by reference.

1 Mirzaei, H. R., Rodriguez, A., Shepphird, J., Brown, C. E. & Badie, B. Chimeric Antigen Receptors T Cell Therapy in Solid Tumor: Challenges and Clinical Applications. *Front Immunol* 8, 1850-1850, doi:10.3389/fimmu.2017.01850 (2017).

2 Majzner, R. G. & Mackall, C. L. Clinical lessons learned from the first leg of the CAR T cell journey. *Nature Medicine* 25, 1341-1355, doi:10.1038/s41591-019-0564-6 (2019).

3 Tsherniak, A. et al. Defining a Cancer Dependency Map. *Cell* 170, 564-576.e516, doi:10.1016/j.cell.2017.06.010 (2017).

4 Germain, R. N. & Margulies, D. H. The biochemistry and cell biology of antigen processing and presentation. *Annu Rev Immunol* 11, 403-450, doi:10.1146/annurev.iy.11.040193.002155 (1993).

5 Crittenden, M. R. et al. Tumor cure by radiation therapy and checkpoint inhibitors depends on pre-existing immunity. *Scientific Reports* 8, 7012, doi:10.1038/s41598-018-25482-w (2018).

6 Yossef, R. et al. Enhanced detection of neoantigen-reactive T cells targeting unique and shared oncogenes for personalized cancer immunotherapy. *JCI Insight* 3, doi:10.1172/jci.insight.122467 (2018).

7 Yarmarkovich, M. et al. Immunogenicity and Immune Silence in Human Cancer. *Frontiers in Immunology* 11, doi:10.3389/fimmu.2020.00069 (2020).

8 Leko, V. & Rosenberg, S. A. Identifying and Targeting Human Tumor Antigens for T Cell-Based Immunotherapy of Solid Tumors. *Cancer cell* 38, 454-472, doi:10.1016/j.ccell.2020.07.013 (2020).

9 Rosenthal, R. et al. Neoantigen-directed immune escape in lung cancer evolution. *Nature* 567, 479-485, doi:10.1038/s41586-019-1032-7 (2019).

10 Schumacher, T. N. & Schreiber, R. D. Neoantigens in cancer immunotherapy. *Science* 348, 69-74, doi:10.1126/science.aaa4971 (2015).

11 Shao, W. et al. The SysteMHC Atlas project. *Nucleic Acids Res* 46, D1237-D1247, doi:10.1093/nar/gkx664 (2018).

12 Maus, M. V. et al. An MHC-restricted antibody-based chimeric antigen receptor requires TCR-like affinity to maintain antigen specificity. *Molecular Therapy—Oncolytics* 3, doi:10.1038/mto.2016.23 (2016).

13 Parkhurst, M. R. et al. T Cells Targeting Carcinoembryonic Antigen Can Mediate Regression of Metastatic Colorectal Cancer but Induce Severe Transient Colitis. *Molecular Therapy* 19, 620-626 (2011).

14 Morgan, R. A. et al. Cancer regression and neurological toxicity following anti-MAGE-A3 TCR gene therapy. *J Immunother* 36, 133-151, doi:10.1097/CJI.0b013e3182829903 (2013).

15 Linette, G. P. et al. Cardiovascular toxicity and titin cross-reactivity of affinity-enhanced T cells in myeloma and melanoma. *Blood* 122, 863-871, doi:10.1182/blood-2013-03-490565 (2013).
16 Matthay, K. K. et al. Neuroblastoma. *Nat Rev Dis Primers* 2, 16078, doi:10.1038/nrdp.2016.78 (2016).
17 Pugh, T. J. et al. The genetic landscape of high-risk neuroblastoma. *Nature genetics* 45, 279-284, doi:10.1038/ng.2529 (2013).
18 Schramm, A. et al. Mutational dynamics between primary and relapse neuroblastomas. *Nature Genetics* 47, 872-877, doi:10.1038/ng.3349 (2015).
19 Cheung, N.-K. V. et al. Association of Age at Diagnosis and Genetic Mutations in Patients With Neuroblastoma. *JAMA* 307, 1062-1071, doi:10.1001/jama.2012.228 (2012).
20 Molenaar, J. J. et al. Sequencing of neuroblastoma identifies chromothripsis and defects in neuritogenesis genes. *Nature* 483, 589-593, doi:10.1038/nature10910 (2012).
21 Brady, S. W. et al. Pan-neuroblastoma analysis reveals age- and signature-associated driver alterations. *Nature Communications* 11, 5183, doi:10.1038/s41467-020-18987-4 (2020).
22 Woelfl, M. et al. *Expression of MHC class I, MHC class II, and cancer germline antigens in neuroblastoma*. Vol. 54 (2005).
23 Burr, M. L. et al. An Evolutionarily Conserved Function of Polycomb Silences the MHC Class I Antigen Presentation Pathway and Enables Immune Evasion in Cancer. *Cancer Cell* 36, 385-401.e388 (2019).
24 Decaesteker, B. et al. TBX2 is a neuroblastoma core regulatory circuitry component enhancing MYCN/FOXM1 reactivation of DREAM targets. *Nature communications* 9, 4866-4866, doi:10.1038/s41467-018-06699-9 (2018).
25 Wang, L. et al. ASCL1 is a MYCN- and LMO1-dependent member of the adrenergic neuroblastoma core regulatory circuitry. *Nature Communications* 10, 5622, doi:10.1038/s41467-019-13515-5 (2019).
26 Durbin, A. D. et al. Selective gene dependencies in MYCN-amplified neuroblastoma include the core transcriptional regulatory circuitry. *Nat. Genet.* 50, 1240-1246, doi:10.1038/s41588-018-0191-z (2018).
27 van Groningen, T. et al. A NOTCH feed-forward loop drives reprogramming from adrenergic to mesenchymal state in neuroblastoma. *Nature Communications* 10, 1530, doi:10.1038/s41467-019-09470-w (2019).
28 Boeva, V. et al. Heterogeneity of neuroblastoma cell identity defined by transcriptional circuitries. *Nat. Genet.* 49, 1408-1413, doi:10.1038/ng.3921 (2017).
29 Rokita, J. L. et al. Genomic Profiling of Childhood Tumor Patient-Derived Xenograft Models to Enable Rational Clinical Trial Design. *Cell Rep* 29, 1675-1689.e1679, doi:10.1016/j.celrep.2019.09.071 (2019).
30 Kowalewski, D. J. & Stevanović, S. Biochemical large-scale identification of MHC class I ligands. *Methods in molecular biology* (Clifton, N.J.) 960, 145-157 (2013).
31 Bassani-Sternberg, M. et al. Direct identification of clinically relevant neoepitopes presented on native human melanoma tissue by mass spectrometry. *Nature Communications* 7, 13404, doi:10.1038/ncomms13404 (2016).
32 Ma, X. et al. Pan-cancer genome and transcriptome analyses of 1,699 paediatric leukaemias and solid tumours. *Nature* 555, 371-376, doi:10.1038/nature25795 (2018).
33 Aguet, F. et al. The GTEx Consortium atlas of genetic regulatory effects across human tissues. *bioRxiv,* 787903, doi:10.1101/787903 (2019).
34 Freudenmann, L. K., Marcu, A. & Stevanović, S. Mapping the tumour human leukocyte antigen (HLA) ligandome by mass spectrometry. *Immunology* 154, 331-345, doi:10.1111/imm.12936 (2018).
35 Mi, H., Muruganujan, A., Ebert, D., Huang, X. & Thomas, P. D. PANTHER version 14: more genomes, a new PANTHER GO-slim and improvements in enrichment analysis tools. *Nucleic Acids Res* 47, D419-d426, doi:10.1093/nar/gky1038 (2019).
36 Ashburner, M. et al. Gene ontology: tool for the unification of biology. The Gene Ontology Consortium. *Nat Genet* 25, 25-29, doi:10.1038/75556 (2000).
37 Li, Z. et al. GDNF family receptor alpha 2 promotes neuroblastoma cell proliferation by interacting with PTEN. *Biochemical and Biophysical Research Communications* 510, 339-344 (2019).
38 Guo, C. et al. IGFBPL1 Regulates Axon Growth through IGF-1-mediated Signaling Cascades. *Scientific reports* 8, 2054-2054, doi:10.1038/s41598-018-20463-5 (2018).
39 Raabe, E. H. et al. Prevalence and functional consequence of PHOX2B mutations in neuroblastoma. *Oncogene* 27, 469, doi:10.1038/sj.onc.1210659 (2007).
40 Lee, N. H. et al. Clinical Significance of Tyrosine Hydroxylase mRNA Transcripts in Peripheral Blood at Diagnosis in Patients with Neuroblastoma. *Cancer research and treatment: Official journal of Korean Cancer Association* 48, 1399-1407, doi:10.4143/crt.2015.481 (2016).
41 Furlan, A., Lubke, M., Adameyko, I., Lallemend, F. & Ernfors, P. The transcription factor Hmx1 and growth factor receptor activities control sympathetic neurons diversification. *The EMBO journal* 32, 1613-1625, doi:10.1038/emboj.2013.85 (2013).
42 Marachelian, A. et al. Expression of Five Neuroblastoma Genes in Bone Marrow or Blood of Patients with Relapsed/Refractory Neuroblastoma Provides a New Biomarker for Disease and Prognosis. *Clinical Cancer Research* 23, 5374-5383, doi:10.1158/1078-0432.Ccr-16-2647 (2017).
43 Toor, J. S. et al. A Recurrent Mutation in Anaplastic Lymphoma Kinase with Distinct Neoepitope Conformations. *Frontiers in Immunology* 9, doi:10.3389/fimmu.2018.00099 (2018).
44 van Groningen, T. et al. Neuroblastoma is composed of two super-enhancer-associated differentiation states. *Nat Genet* 49, 1261-1266, doi:10.1038/ng.3899 (2017).
45 Boeva, V. et al. Heterogeneity of neuroblastoma cell identity defined by transcriptional circuitries. *Nat Genet* 49, 1408-1413, doi:10.1038/ng.3921 (2017).
46 Decaesteker, B. et al. TBX2 is a neuroblastoma core regulatory circuitry component enhancing MYCN/FOXM1 reactivation of DREAM targets. *Nature Communications* 9, 4866, doi:10.1038/s41467-018-06699-9 (2018).
47 Cardoso-Moreira, M. et al. Gene expression across mammalian organ development. *Nature* 571, 505-509, doi:10.1038/s41586-019-1338-5 (2019).
48 Pattyn, A., Morin, X., Cremer, H., Goridis, C. & Brunet, J.-F. The homeobox gene Phox2b is essential for the development of autonomic neural crest derivatives. *Nature* 399, 366-370, doi:10.1038/20700 (1999).

49 Dauger, S. et al. <em>Phox2b</em> controls the development of peripheral chemoreceptors and afferent visceral pathways. *Development* 130, 6635, doi:10.1242/dev.00866 (2003).

50 Kildisiute, G. et al. Tumor to normal single-cell mRNA comparisons reveal a pan-neuroblastoma cancer cell. *Science Advances* 7, eabd3311, doi:10.1126/sciadv.abd3311 (2021).

51 Hata, J. L. et al. Diagnostic Utility of PHOX2B in Primary and Treated Neuroblastoma and in Neuroblastoma Metastatic to the Bone Marrow. *Archives of Pathology & Laboratory Medicine* 139, 543-546, doi:10.5858/arpa.2014-0255-OA (2015).

52 Hung, Y. P., Lee, J. P., Bellizzi, A. M. & Hornick, J. L. PHOX2B reliably distinguishes neuroblastoma among small round blue cell tumours. *Histopathology* 71, 786-794 (2017).

53 Mosse, Y. P. et al. Germline PHOX2B mutation in hereditary neuroblastoma. *Am J Hum Genet* 75, 727-730, doi:10.1086/424530 (2004).

54 Dharia, N. V. et al. A first-generation pediatric cancer dependency map. *Nature Genetics* 53, 529-538, doi:10.1038/s41588-021-00819-w (2021).

55 Canaday, D. H. et al. T-cell hybridomas from HLA-transgenic mice as tools for analysis of human antigen processing. *J Immunol Methods* 281, 129-142, doi:10.1016/j.jim.2003.07.004 (2003).

56 Beasley, M. D., Niven, K. P., Winnall, W. R. & Kiefel, B. R. Bacterial cytoplasmic display platform Retained Display (ReD) identifies stable human germline antibody frameworks. *Biotechnol J* 10, 783-789, doi:10.1002/biot.201400560 (2015).

57 Kunert, A., Obenaus, M., Lamers, C. H. J., Blankenstein, T. & Debets, R. T-cell Receptors for Clinical Therapy: <em>In Vitro</em> Assessment of Toxicity Risk. *Clinical Cancer Research* 23, 6012-6020, doi:10.1158/1078-0432.Ccr-17-1012 (2017).

58 Rudolph, M. G., Stanfield, R. L. & Wilson, I. A. How TCRs bind MHCs, peptides, and coreceptors. *Annu Rev Immunol* 24, 419-466, doi:10.1146/annurev.immunol.23.021704.115658 (2006).

59 Nerli, S. & Sgourakis, N. G. Structure-based modeling of SARS-CoV-2 peptide/HLA-A02 antigens. *bioRxiv*, 2020.2003.2023.004176, doi:10.1101/2020.03.23.004176 (2020).

60 Asgharzadeh, S. et al. Clinical Significance of Tumor-Associated Inflammatory Cells in Metastatic Neuroblastoma. *Journal of Clinical Oncology* 30, 3525-3532, doi:10.1200/JCO.2011.40.9169 (2012).

61 Douglass, J. et al. Bispecific antibodies targeting mutant <em>RAS</em> neoantigens. *Science Immunology* 6, eabd5515, doi:10.1126/sciimmunol.abd5515 (2021).

62 Hsiue, E. H.-C. et al. Targeting a neoantigen derived from a common <em>TP53</em> mutation. *Science, eabc*8697, doi:10.1126/science.abc8697 (2021).

63 Perez-Riverol, Y. et al. The PRIDE database and related tools and resources in 2019: improving support for quantification data. *Nucleic Acids Res* 47, D442-d450, doi:10.1093/nar/gky1106 (2019).

64 Nielsen, M. et al. Reliable prediction of T-cell epitopes using neural networks with novel sequence representations. *Protein Sci* 12, 1007-1017, doi:10.1110/ps.0239403 (2003).

65 Reynisson, B., Alvarez, B., Paul, S., Peters, B. & Nielsen, M. NetMHCpan-4.1 and NetMHCIIpan-4.0: improved predictions of MHC antigen presentation by concurrent motif deconvolution and integration of MS MHC eluted ligand data. *Nucleic Acids Res* 48, W449-w454, doi:10.1093/nar/gkaa379 (2020).

66 Sarkizova, S. et al. A large peptidome dataset improves HLA class I epitope prediction across most of the human population. *Nat Biotechnol* 38, 199-209, doi:10.1038/s41587-019-0322-9 (2020).

67 Shao, W., Caron, E., Pedrioli, P. & Aebersold, R. in *Bioinformatics for Cancer Immunotherapy: Methods and Protocols* (ed Sebastian Boegel) 173-181 (Springer US, 2020).

68 Overall, S. A. et al. High throughput pMHC-I tetramer library production using chaperone-mediated peptide exchange. *Nature Communications* 11, 1909, doi:10.1038/s41467-020-15710-1 (2020).

69 Dolton, G. et al. Optimized Peptide-MHC Multimer Protocols for Detection and Isolation of Autoimmune T-Cells. *Front Immunol* 9, 1378-1378, doi:10.3389/fimmu.2018.01378 (2018).

70 Canaday, D. H. Production of $CD4^{+}$ and $CD8^{+}$ T cell hybridomas. *Methods in molecular biology* (Clifton, N.J.) 960, 297-307, doi:10.1007/978-1-62703-218-6_22 (2013).

71 Garboczi D N, Hung D T, Wiley D C. HLA-A2-peptide complexes: refolding and crystallization of molecules expressed in *Escherichia coli* and complexed with single antigenic peptides. *Proc Natl Acad Sci USA* (1992) 89:3429-33. doi:10.1073/pnas.89.8.3429

72 Studier F W. Stable expression clones and auto-induction for protein pro-duction in *E. coli. Methods Mol Biol* (2014) 1091:17-32. doi:10.1007/978-1-62703-691-7_2

73 Winn M D, Ballard C C, Cowtan K D, Dodson E J, Emsley P, Evans P R, et al. Overview of the CCP4 suite and current developments. *Acta Crystallogr D Biol Crystallogr* (2011) 67:235-42. doi:10.1107/S0907444910045749)

74 McCoy A J, Grosse-Kunstleve R W, Adams P D, Winn M D, Storoni L C, Read R J. Phaser crystallographic software. *J Appl Crystallogr* (2007) 40:658-74. doi:10.1107/50021889807021206

75 Cole D K, Bulek A M, Dolton G, Schauenberg A J, Szomolay B, Rittase W, Trimby A, Jothikumar P, Fuller A, Skowera A, Rossjohn J, Zhu C, Miles J J, Peakman M, Wooldridge L, Rizkallah P J, Sewell A K. Hotspot autoimmune T cell receptor binding underlies pathogen and insulin peptide cross-reactivity. J Clin Invest. 2016 Jun. 1; 126(6):2191-204. doi: 10.1172/JCI85679. Epub 2016 May 16. Erratum in: J Clin Invest. 2016 Sep. 1; 126(9): 3626. PMID: 27183389; PMCID: PMC4887163.

76 Shimizu A, Kawana-Tachikawa A, Yamagata A, Han C, Zhu D, Sato Y, Nakamura H, Koibuchi T, Carlson J, Martin E, Brumme C J, Shi Y, Gao G F, Brumme Z L, Fukai S, Iwamoto A. Structure of TCR and antigen complexes at an immunodominant CTL epitope in HIV-1 infection. Sci Rep. 2013 Nov. 6; 3:3097. doi: 10.1038/srep03097. PMID: 24192765; PMCID: PMC3818656.

77 Emsley P, Cowtan K. Coot: model-building tools for molecular graphics. *Acta Crystallogr D Biol Crystallogr* (2004) 60:2126-32. doi:10.1107/S0907444904019158

78 Adams P D, Afonine P V, Bunkóczi G, Chen V B, Davis I W, Echols N, et al. PHENIX: a comprehensive Python-based system for macromolecular structure solution. *Acta Crystallogr D Biol Crystallogr* (2010) 66:213-21. doi:10.1107/S0907444909052925

79 Nerli S, Sgourakis N G. Structure-based modeling of SARS-CoV-2 peptide/HLA-A02 antigens. Front. Med. Technol. 2020 Nov. 17: 2020.03.23.004176. doi: 10.3389/fmedt.2020.553478.

80 Maccari G, Robinson J, Ballingall K, Guethlein L A, Grimholt U, Kaufman J, et al. IPD-MHC 2.0: an improved inter-species database for the study of the major histocompatibility complex. *Nucleic Acids Res* (2017) 45:D860-4. doi:10.1093/nar/gkw1050

81 Davis I W, Leaver-Fay A, Chen V B, Block J N, Kapral G J, Wang X, Murray L W, Arendall W B 3rd, Snoeyink J, Richardson J S, Richardson D C. MolProbity: all-atom contacts and structure validation for proteins and nucleic acids. Nucleic Acids Res. 2007 July; 35(Web Server issue): W375-83. doi: 10.1093/nar/gkm216. Epub 2007 Apr. 22. PMID: 17452350; PMCID: PMC1933162.

82 Schrodinger L L C (2010) The PyMOL Molecular Graphics System, Version 1.3r1.

Andreatta, M., Lund, O. & Nielsen, M. Simultaneous alignment and clustering of peptide data using a Gibbs sampling approach. *Bioinformatics* 29, 8-14, doi:10.1093/bioinformatics/bts621 (2012).

Alvarez, B. et al. NNAlign_MA; MHC Peptidome Deconvolution for Accurate MHC Binding Motif Characterization and Improved T-cell Epitope Predictions. *Mol Cell Proteomics* 18, 2459-2477, doi:10.1074/mcp.TIR119.001658 (2019).

83 Sci Adv (2021) 7: eabd3311

84 Am J Hum Genet. (2004) 74: 761-764

85 Am J Hum Genet. (2004) 75:727-730

86 Senior et al., Nature 577:706-710 (2020)

WO/2019/178081

WO/2011/075761

WO/2013/023251

WO/2013/000023

SEQUENCE LISTING

```
Sequence total quantity: 74
SEQ ID NO: 1            moltype = AA  length = 9
FEATURE                 Location/Qualifiers
source                  1..9
                        mol_type = protein
                        organism = Homo sapiens
SEQUENCE: 1
QYNPIRTTF                                                          9

SEQ ID NO: 2            moltype = AA  length = 314
FEATURE                 Location/Qualifiers
source                  1..314
                        mol_type = protein
                        organism = Homo sapiens
SEQUENCE: 2
MYKMEYSYLN SSAYESCMAG MDTSSLASAY ADFSSCSQAS GFQYNPIRTT FGATSGCPSL  60
TPGSCSLGTL RDHQSSPYAA VPYKLFTDHG GLNEKRKQRR IRTTFTSAQL KELERVFAET  120
HYPDIYTREE LALKIDLTEA RVQVWFQNRR AKFRKQERAA AAAAAAAKNG SSGKKSDSSR  180
DDESKEAKST DPDSTGGPGP NPNPTPSCGA NGGGGGGPSP AGAPGAAGPG GPGGEPGKGG  240
AAAAAAAAAA AAAAAAAAAA GGLAAAGGPG QGWAPGPGPI TSIPDSLGGP FASVLSSLQR  300
PNGAKAALVK SSMF                                                    314

SEQ ID NO: 3            moltype = AA  length = 257
FEATURE                 Location/Qualifiers
source                  1..257
                        mol_type = protein
                        organism = Homo sapiens
SEQUENCE: 3
SRNGGDGQSV LTQPPSVSVS PGQTASITCS GDSLGNKYAC WYQQKPGQSP VLVIYQDSKR  60
PSGIPERFSG SNSGNTATLT ISGTQAMDEA DYYCQAWDSS RGYTVVFGTG TKVTVSSQTG  120
GSGGGGSGGG GSGGGGSEVQ LLESGGGLVQ PGGSLRLSCA ASGFTFDSYA MSWVRQAPGK  180
GLEWVSAISG YGGSTYYADS VKGRFTISRD NSKNTLYLQM NSLRAEDTAV YYCAKYTYFL  240
DAFDIWGQGT MVTVSSS                                                 257

SEQ ID NO: 4            moltype = AA  length = 108
FEATURE                 Location/Qualifiers
source                  1..108
                        mol_type = protein
                        organism = Homo sapiens
SEQUENCE: 4
QSVLTQPPSV SVSPGQTASI TCSGDSLGNK YACWYQQKPG QSPVLVIYQD SKRPSGIPER  60
FSGSNSGNTA TLTISGTQAM DEADYYCQAW DSSRGYTVVF GTGTKVTV                108

SEQ ID NO: 5            moltype = AA  length = 119
FEATURE                 Location/Qualifiers
source                  1..119
                        mol_type = protein
                        organism = Homo sapiens
SEQUENCE: 5
EVQLLESGGG LVQPGGSLRL SCAASGFTFD SYAMSWVRQA PGKGLEWVSA ISGYGGSTYY  60
ADSVKGRFTI SRDNSKNTLY LQMNSLRAED TAVYYCAKYT YFLDAFDIWG QGTMVTVSS   119

SEQ ID NO: 6            moltype = AA  length = 7
FEATURE                 Location/Qualifiers
source                  1..7
                        mol_type = protein
                        organism = Homo sapiens
```

```
SEQUENCE: 6
DSLGNKY                                                      7

SEQ ID NO: 7          moltype = AA  length = 7
FEATURE               Location/Qualifiers
source                1..7
                      mol_type = protein
                      organism = Homo sapiens
SEQUENCE: 7
QDSKRPS                                                      7

SEQ ID NO: 8          moltype = AA  length = 12
FEATURE               Location/Qualifiers
source                1..12
                      mol_type = protein
                      organism = Homo sapiens
SEQUENCE: 8
QAWDSSRGYT VV                                                12

SEQ ID NO: 9          moltype = AA  length = 8
FEATURE               Location/Qualifiers
source                1..8
                      mol_type = protein
                      organism = Homo sapiens
SEQUENCE: 9
GFTFDSYA                                                     8

SEQ ID NO: 10         moltype = AA  length = 6
FEATURE               Location/Qualifiers
source                1..6
                      mol_type = protein
                      organism = Homo sapiens
SEQUENCE: 10
SGYGGS                                                       6

SEQ ID NO: 11         moltype = AA  length = 9
FEATURE               Location/Qualifiers
source                1..9
                      mol_type = protein
                      organism = Homo sapiens
SEQUENCE: 11
YTYFLDAFD                                                    9

SEQ ID NO: 12         moltype = AA  length = 260
FEATURE               Location/Qualifiers
source                1..260
                      mol_type = protein
                      organism = Homo sapiens
SEQUENCE: 12
SRNGGDGQSV LTQPPSVSVS PGQTASITCS GDKLGDKYAC WYQQKPGQSP VLVIYQDSKR  60
PSGIPERFSG SNSGNTATLT ISGTQAMDEA DYYCQAWDMV GSWTVVFGTG TKVTVSSQTG  120
GSGGGGSGGG GSGGGGSEVQ LLESGGGLVQ PGGSLRLSCA ASGFTFSSYA MSWVRQAPGK  180
GLEWVSAISG SGGSTYYADS VKGRFTISRD NSKNTLYLQM NSLRAEDTAV YYCAKPRFDG  240
QWDNAFDIWG QGTMVTVSSS                                        260

SEQ ID NO: 13         moltype = AA  length = 108
FEATURE               Location/Qualifiers
source                1..108
                      mol_type = protein
                      organism = Homo sapiens
SEQUENCE: 13
QSVLTQPPSV SVSPGQTASI TCSGDKLGDK YACWYQQKPG QSPVLVIYQD SKRPSGIPER  60
FSGSNSGNTA TLTISGTQAM DEADYYCQAW DMVGSWTVVF GTGTKVTV          108

SEQ ID NO: 14         moltype = AA  length = 122
FEATURE               Location/Qualifiers
source                1..122
                      mol_type = protein
                      organism = Homo sapiens
SEQUENCE: 14
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKPR FDGQWDNAFD IWGQGTMVTV  120
SS                                                           122

SEQ ID NO: 15         moltype = AA  length = 7
FEATURE               Location/Qualifiers
source                1..7
                      mol_type = protein
                      organism = Homo sapiens
```

```
SEQUENCE: 15
DKLGDKY                                                            7

SEQ ID NO: 16          moltype = AA  length = 7
FEATURE                Location/Qualifiers
source                 1..7
                       mol_type = protein
                       organism = Homo sapiens
SEQUENCE: 16
QDSKRPS                                                            7

SEQ ID NO: 17          moltype = AA  length = 12
FEATURE                Location/Qualifiers
source                 1..12
                       mol_type = protein
                       organism = Homo sapiens
SEQUENCE: 17
QAWDMVGSWT VV                                                      12

SEQ ID NO: 18          moltype = AA  length = 7
FEATURE                Location/Qualifiers
source                 1..7
                       mol_type = protein
                       organism = Homo sapiens
SEQUENCE: 18
GFTFSSY                                                            7

SEQ ID NO: 19          moltype = AA  length = 6
FEATURE                Location/Qualifiers
source                 1..6
                       mol_type = protein
                       organism = Homo sapiens
SEQUENCE: 19
SGSGGS                                                             6

SEQ ID NO: 20          moltype = AA  length = 13
FEATURE                Location/Qualifiers
source                 1..13
                       mol_type = protein
                       organism = Homo sapiens
SEQUENCE: 20
PRFDGQWDNA FDI                                                     13

SEQ ID NO: 21          moltype = AA  length = 502
FEATURE                Location/Qualifiers
source                 1..502
                       mol_type = protein
                       organism = Homo sapiens
SEQUENCE: 21
MALPVTALLL PLALLLHAAR PSRNGGDGQS VLTQPPSVSV SPGQTASITC SGDSLGNKYA  60
CWYQQKPGQS PVLVIYQDSK RPSGIPERFS GSNSGNTATL TISGTQAMDE ADYYCQAWDS  120
SRGYTVVFGT GTKVTVSSQT GGSGGGGSGG GGSGGGGSEV QLLESGGGLV QPGGSLRLSC  180
AASGFTFDSY AMSWVRQAPG KGLEWVSAIS GYGGSTYYAD SVKGRFTISR DNSKNTLYLQ  240
MNSLRAEDTA VYYCAKYTYF LDAFDIWGQG TMVTVSSSST TTPAPRPPTP APTIASQPLS  300
LRPEACRPAA GGAVHTRGLD FACDIYIWAP LAGTCGVLLL SLVITLYCKR GRKKLLYIFK  360
QPFMRPVQTT QEEDGCSCRF PEEEEGGCEL RVKFSRSADA PAYKQGQNQL YNELNLGRRE  420
EYDVLDKRRG RDPEMGGKPR RKNPQEGLYN ELQKDKMAEA YSEIGMKGER RRGKGHDGLY  480
QGLSTATKDT YDALHMQALP PR                                           502

SEQ ID NO: 22          moltype = AA  length = 504
FEATURE                Location/Qualifiers
source                 1..504
                       mol_type = protein
                       organism = Homo sapiens
SEQUENCE: 22
MALPVTALLL PLALLLHAAR PSRNGGDGQS VLTQPPSVSV SPGQTASITC SGDKLGDKYA  60
CWYQQKPGQS PVLVIYQDSK RPSGIPERFS GSNSGNTATL TISGTQAMDE ADYYCQAWDM  120
VGSWTVVFGT GTKVTVSSQT GGSGGGGSGG GGSGGGGSEV QLLESGGGLV QPGGSLRLSC  180
AASGFTFSSY AMSWVRQAPG KGLEWVSAIS GSGGSTYYAD SVKGRFTISR DNSKNTLYLQ  240
MNSLRAEDTA VYYCAKPRFD GQWDNAFDIW GQGTMVTVSS STTTPAPRPP TPAPTIASQP  300
LSLRPEACRP AAGGAVHTRG LDFACDIYIW APLAGTCGVL LLSLVITLYC KRGRKKLLYI  360
FKQPFMRPVQ TTQEEDGCSC RFPEEEEGGC ELRVKFSRSA DAPAYKQGQN QLYNELNLGR  420
REEYDVLDKR RGRDPEMGGK PRRKNPQEGL YNELQKDKMA EAYSEIGMKG ERRRGKGHDG  480
LYQGLSTATK DTYDALHMQA LPPR                                         504

SEQ ID NO: 23          moltype = AA  length = 257
FEATURE                Location/Qualifiers
source                 1..257
                       mol_type = protein
```

```
                         organism = Homo sapiens
SEQUENCE: 23
SRNGGDGQSV LTQPPSVSVS PGQTASITCS GDSLGYKYAC WYQQKPGQSP VLVIYQDSKR  60
PSGIPERFSG SNSGNTATLT ISGTQAMDEA DYYCQAWDSL GVNTVVFGTG TKVTVSSQTG  120
GSGGGGSGGG GSGGGGSEVQ LLESGGGLVQ PGGSLRLSCA ASGFTFNYYA MSWVRQAPGK  180
GLEWVSAISG YGGSTYYADS VKGRFTISRD NSKNTLYLQM NSLRAEDTAV YYCAKASEAY  240
SAFDIWGQGT MVTVSSS                                                 257

SEQ ID NO: 24            moltype = AA  length = 108
FEATURE                  Location/Qualifiers
source                   1..108
                         mol_type = protein
                         organism = Homo sapiens
SEQUENCE: 24
QSVLTQPPSV SVSPGQTASI TCSGDSLGYK YACWYQQKPG QSPVLVIYQD SKRPSGIPER  60
FSGSNSGNTA TLTISGTQAM DEADYYCQAW DSLGVNTVVF GTGTKVTV                108

SEQ ID NO: 25            moltype = AA  length = 119
FEATURE                  Location/Qualifiers
source                   1..119
                         mol_type = protein
                         organism = Homo sapiens
SEQUENCE: 25
EVQLLESGGG LVQPGGSLRL SCAASGFTFN YYAMSWVRQA PGKGLEWVSA ISGYGGSTYY  60
ADSVKGRFTI SRDNSKNTLY LQMNSLRAED TAVYYCAKAS EAYSAFDIWG QGTMVTVSS   119

SEQ ID NO: 26            moltype = AA  length = 7
FEATURE                  Location/Qualifiers
source                   1..7
                         mol_type = protein
                         organism = Homo sapiens
SEQUENCE: 26
DSLGYKY                                                            7

SEQ ID NO: 27            moltype = AA  length = 7
FEATURE                  Location/Qualifiers
source                   1..7
                         mol_type = protein
                         organism = Homo sapiens
SEQUENCE: 27
QDSKRPS                                                            7

SEQ ID NO: 28            moltype = AA  length = 12
FEATURE                  Location/Qualifiers
source                   1..12
                         mol_type = protein
                         organism = Homo sapiens
SEQUENCE: 28
QAWDSLGVNT VV                                                      12

SEQ ID NO: 29            moltype = AA  length = 8
FEATURE                  Location/Qualifiers
source                   1..8
                         mol_type = protein
                         organism = Homo sapiens
SEQUENCE: 29
GFTFNYYA                                                           8

SEQ ID NO: 30            moltype = AA  length = 6
FEATURE                  Location/Qualifiers
source                   1..6
                         mol_type = protein
                         organism = Homo sapiens
SEQUENCE: 30
SGYGGS                                                             6

SEQ ID NO: 31            moltype = AA  length = 30
FEATURE                  Location/Qualifiers
source                   1..30
                         mol_type = protein
                         organism = Homo sapiens
SEQUENCE: 31
ALASERGLUA LATYRSERAL APHEASPILE                                   30

SEQ ID NO: 32            moltype = AA  length = 261
FEATURE                  Location/Qualifiers
source                   1..261
                         mol_type = protein
                         organism = Homo sapiens
```

```
SEQUENCE: 32
SRNGGDGQSV LTQPPSVSAA PGQKVTISCS GSSSNIGNNY VSWYQQLPGT APKLLIYDNN  60
KRPSGIPDRF SGSKSGTSAT LGITGLQTGD EADYYCGTWD HMGRNTVVFG TGTKVTVSSQ  120
TGGSGGGGSG GGGSGGGGSE VQLLESGGGL VQPGGSLRLS CAASGFTFSD YAMSWVRQAP  180
GKGLEWVSAI SGTGGSTYYA DSVKGRFTIS RDNSKNTLYL QMNSLRAEDT AVYYCAKEFS  240
VVNSAAFDIW GQGTMVTVSS S                                            261

SEQ ID NO: 33           moltype = AA  length = 110
FEATURE                 Location/Qualifiers
source                  1..110
                        mol_type = protein
                        organism = Homo sapiens
SEQUENCE: 33
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDHMGRNTV VFGTGTKVTV             110

SEQ ID NO: 34           moltype = AA  length = 121
FEATURE                 Location/Qualifiers
source                  1..121
                        mol_type = protein
                        organism = Homo sapiens
SEQUENCE: 34
EVQLLESGGG LVQPGGSLRL SCAASGFTFS DYAMSWVRQA PGKGLEWVSA ISGTGGSTYY  60
ADSVKGRFTI SRDNSKNTLY LQMNSLRAED TAVYYCAKEF SVVNSAAFDI WGQGTMVTVS  120
S                                                                  121

SEQ ID NO: 35           moltype = AA  length = 8
FEATURE                 Location/Qualifiers
source                  1..8
                        mol_type = protein
                        organism = Homo sapiens
SEQUENCE: 35
SSNIGNNY                                                           8

SEQ ID NO: 36           moltype = AA  length = 7
FEATURE                 Location/Qualifiers
source                  1..7
                        mol_type = protein
                        organism = Homo sapiens
SEQUENCE: 36
DNNKRPS                                                            7

SEQ ID NO: 37           moltype = AA  length = 12
FEATURE                 Location/Qualifiers
source                  1..12
                        mol_type = protein
                        organism = Homo sapiens
SEQUENCE: 37
GTWDHMGRNT VV                                                      12

SEQ ID NO: 38           moltype = AA  length = 8
FEATURE                 Location/Qualifiers
source                  1..8
                        mol_type = protein
                        organism = Homo sapiens
SEQUENCE: 38
GFTFSDYA                                                           8

SEQ ID NO: 39           moltype = AA  length = 6
FEATURE                 Location/Qualifiers
source                  1..6
                        mol_type = protein
                        organism = Homo sapiens
SEQUENCE: 39
SGTGGS                                                             6

SEQ ID NO: 40           moltype = AA  length = 12
FEATURE                 Location/Qualifiers
source                  1..12
                        mol_type = protein
                        organism = Homo sapiens
SEQUENCE: 40
EFSVVNSAAF DI                                                      12

SEQ ID NO: 41           moltype = AA  length = 257
FEATURE                 Location/Qualifiers
source                  1..257
                        mol_type = protein
                        organism = Homo sapiens
```

```
SEQUENCE: 41
SRNGGDGQSV LTQPPSVSVS PGQTASITCS GDKLGDKYAC WYQQKPGQSP VLVIYQDSKR  60
PSGIPERFSG SNSGNTATLT ISGTQAMDEA DYYCQAWDSI GNMTVVFGTG TKVTVSSQTG  120
GSGGGGSGGG GSGGGGSEVQ LLESGGGLVQ PGGSLRLSCA ASGFTFDYYA MSWVRQAPGK  180
GLEWVSAISG YGGSTYYADS VKGRFTISRD NSKNTLYLQM NSLRAEDTAV YYCAKASEYT  240
NAFDIWGQGI MVTVSSS                                                 257

SEQ ID NO: 42          moltype = AA  length = 108
FEATURE                Location/Qualifiers
source                 1..108
                       mol_type = protein
                       organism = Homo sapiens
SEQUENCE: 42
QSVLTQPPSV SVSPGQTASI TCSGDKLGDK YACWYQQKPG QSPVLVIYQD SKRPSGIPER  60
FSGSNSGNTA TLTISGTQAM DEADYYCQAW DSIGNMTVVF GTGTKVTV                108

SEQ ID NO: 43          moltype = AA  length = 119
FEATURE                Location/Qualifiers
source                 1..119
                       mol_type = protein
                       organism = Homo sapiens
SEQUENCE: 43
EVQLLESGGG LVQPGGSLRL SCAASGFTFD YYAMSWVRQA PGKGLEWVSA ISGYGGSTYY  60
ADSVKGRFTI SRDNSKNTLY LQMNSLRAED TAVYYCAKAS EYTNAFDIWG QGIMVTVSS   119

SEQ ID NO: 44          moltype = AA  length = 7
FEATURE                Location/Qualifiers
source                 1..7
                       mol_type = protein
                       organism = Homo sapiens
SEQUENCE: 44
DKLGDKY                                                            7

SEQ ID NO: 45          moltype = AA  length = 7
FEATURE                Location/Qualifiers
source                 1..7
                       mol_type = protein
                       organism = Homo sapiens
SEQUENCE: 45
QDSKRPS                                                            7

SEQ ID NO: 46          moltype = AA  length = 12
FEATURE                Location/Qualifiers
source                 1..12
                       mol_type = protein
                       organism = Homo sapiens
SEQUENCE: 46
QAWDSIGNMT VV                                                      12

SEQ ID NO: 47          moltype = AA  length = 8
FEATURE                Location/Qualifiers
source                 1..8
                       mol_type = protein
                       organism = Homo sapiens
SEQUENCE: 47
GFTFDYYA                                                           8

SEQ ID NO: 48          moltype = AA  length = 6
FEATURE                Location/Qualifiers
source                 1..6
                       mol_type = protein
                       organism = Homo sapiens
SEQUENCE: 48
SGYGGS                                                             6

SEQ ID NO: 49          moltype = AA  length = 10
FEATURE                Location/Qualifiers
source                 1..10
                       mol_type = protein
                       organism = Homo sapiens
SEQUENCE: 49
ASEYTNAFDI                                                         10

SEQ ID NO: 50          moltype = AA  length = 12
FEATURE                Location/Qualifiers
source                 1..12
                       mol_type = protein
                       organism = Homo sapiens
SEQUENCE: 50
```

```
QAWDSXGXXT VV                                                12

SEQ ID NO: 51          moltype = AA  length = 10
FEATURE                Location/Qualifiers
source                 1..10
                       mol_type = protein
                       organism = Homo sapiens
SEQUENCE: 51
ASEXXXAFDI                                                   10

SEQ ID NO: 52          moltype = AA  length = 9
FEATURE                Location/Qualifiers
source                 1..9
                       mol_type = protein
                       organism = Homo sapiens
SEQUENCE: 52
NYTPIRTTF                                                    9

SEQ ID NO: 53          moltype = AA  length = 9
FEATURE                Location/Qualifiers
source                 1..9
                       mol_type = protein
                       organism = Homo sapiens
SEQUENCE: 53
LYNPIRTTF                                                    9

SEQ ID NO: 54          moltype = AA  length = 9
FEATURE                Location/Qualifiers
source                 1..9
                       mol_type = protein
                       organism = Homo sapiens
SEQUENCE: 54
QYQPLRTTF                                                    9

SEQ ID NO: 55          moltype = AA  length = 9
FEATURE                Location/Qualifiers
source                 1..9
                       mol_type = protein
                       organism = Homo sapiens
SEQUENCE: 55
QYNPIKTTF                                                    9

SEQ ID NO: 56          moltype = AA  length = 9
FEATURE                Location/Qualifiers
source                 1..9
                       mol_type = protein
                       organism = Homo sapiens
SEQUENCE: 56
QYNPLQTTF                                                    9

SEQ ID NO: 57          moltype = AA  length = 9
FEATURE                Location/Qualifiers
source                 1..9
                       mol_type = protein
                       organism = Homo sapiens
SEQUENCE: 57
QYNPLKTTF                                                    9

SEQ ID NO: 58          moltype = AA  length = 9
FEATURE                Location/Qualifiers
source                 1..9
                       mol_type = protein
                       organism = Homo sapiens
SEQUENCE: 58
QYNAIRTTF                                                    9

SEQ ID NO: 59          moltype = AA  length = 9
FEATURE                Location/Qualifiers
source                 1..9
                       mol_type = protein
                       organism = Homo sapiens
SEQUENCE: 59
EVDPIGHLY                                                    9

SEQ ID NO: 60          moltype = AA  length = 9
FEATURE                Location/Qualifiers
source                 1..9
                       mol_type = protein
                       organism = Homo sapiens
```

```
SEQUENCE: 60
ESDPIVAQY                                                        9

SEQ ID NO: 61          moltype = AA  length = 9
FEATURE                Location/Qualifiers
source                 1..9
                       mol_type = protein
                       organism = Homo sapiens
SEQUENCE: 61
RYVIIPTTF                                                        9

SEQ ID NO: 62          moltype = AA  length = 9
FEATURE                Location/Qualifiers
source                 1..9
                       mol_type = protein
                       organism = Homo sapiens
SEQUENCE: 62
KYNIFRSTF                                                        9

SEQ ID NO: 63          moltype = AA  length = 9
FEATURE                Location/Qualifiers
source                 1..9
                       mol_type = protein
                       organism = Homo sapiens
SEQUENCE: 63
SYEPITTTL                                                        9

SEQ ID NO: 64          moltype = AA  length = 9
FEATURE                Location/Qualifiers
source                 1..9
                       mol_type = protein
                       organism = Homo sapiens
SEQUENCE: 64
TYNGIFTTL                                                        9

SEQ ID NO: 65          moltype = AA  length = 21
FEATURE                Location/Qualifiers
source                 1..21
                       mol_type = protein
                       organism = Homo sapiens
SEQUENCE: 65
MALPVTALLL PLALLLHAAR P                                          21

SEQ ID NO: 66          moltype = AA  length = 119
FEATURE                Location/Qualifiers
source                 1..119
                       mol_type = protein
                       organism = Homo sapiens
SEQUENCE: 66
SRNGGDGQSV LTQPPSVSVS PGQTASITCS GDSLGNKYAC WYQQKPGQSP VLVIYQDSKR  60
PSGIPERFSG SNSGNTATLT ISGTQAMDEA DYYCQAWDSS RGYTVVFGTG TKVTVSSQT   119

SEQ ID NO: 67          moltype = AA  length = 18
FEATURE                Location/Qualifiers
source                 1..18
                       mol_type = protein
                       organism = Homo sapiens
SEQUENCE: 67
GGSGGGGSGG GGSGGGGS                                              18

SEQ ID NO: 68          moltype = AA  length = 121
FEATURE                Location/Qualifiers
source                 1..121
                       mol_type = protein
                       organism = Homo sapiens
SEQUENCE: 68
EVQLLESGGG LVQPGGSLRL SCAASGFTFD SYAMSWVRQA PGKGLEWVSA ISGYGGSTYY  60
ADSVKGRFTI SRDNSKNTLY LQMNSLRAED TAVYYCAKYT YFLDAFDIWG QGTMVTVSSS  120
S                                                                121

SEQ ID NO: 69          moltype = AA  length = 45
FEATURE                Location/Qualifiers
source                 1..45
                       mol_type = protein
                       organism = Homo sapiens
SEQUENCE: 69
TTTPAPRPPT PAPTIASQPL SLRPEACRPA AGGAVHTRGL DFACD                45

SEQ ID NO: 70          moltype = AA  length = 24
```

-continued

```
FEATURE                 Location/Qualifiers
source                  1..24
                        mol_type = protein
                        organism = Homo sapiens
SEQUENCE: 70
IYIWAPLAGT CGVLLLSLVI TLYC                                    24

SEQ ID NO: 71           moltype = AA  length = 42
FEATURE                 Location/Qualifiers
source                  1..42
                        mol_type = protein
                        organism = Homo sapiens
SEQUENCE: 71
KRGRKKLLYI FKQPFMRPVQ TTQEEDGCSC RFPEEEEGGC EL                42

SEQ ID NO: 72           moltype = AA  length = 112
FEATURE                 Location/Qualifiers
source                  1..112
                        mol_type = protein
                        organism = Homo sapiens
SEQUENCE: 72
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 73           moltype = AA  length = 119
FEATURE                 Location/Qualifiers
source                  1..119
                        mol_type = protein
                        organism = Homo sapiens
SEQUENCE: 73
SRNGGDGQSV LTQPPSVSVS PGQTASITCS GDKLGDKYAC WYQQKPGQSP VLVIYQDSKR  60
PSGIPERFSG SNSGNTATLT ISGTQAMDEA DYYCQAWDMV GSWTVVFGTG TKVTVSSQT   119

SEQ ID NO: 74           moltype = AA  length = 123
FEATURE                 Location/Qualifiers
source                  1..123
                        mol_type = protein
                        organism = Homo sapiens
SEQUENCE: 74
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKPR FDGQWDNAFD IWGQGTMVTV  120
SSS                                                           123
```

What is claimed:

1. An antibody or antibody fragment that binds an HLA PHOX2B$_{QYNPIRTTF}$ complex, the antibody or antibody fragment comprising:

(i) a light chain variable domain ($V_L$) comprising:

a light chain complementarity determining region 1 (CDR-L1) comprising the amino acid sequence of SEQ ID NO: 6, a light chain complementarity determining region 2 (CDR-L2) comprising the amino acid sequence of SEQ ID NO: 7, and a light chain complementarity determining region 3 (CDR-L3) comprising the amino acid sequence of SEQ ID NO: 8; and (ii) a heavy chain variable domain ($V_H$) comprising:

a heavy chain complementarity determining region 1 (CDR-H1) comprising the amino acid sequence of SEQ ID NO: 9, a heavy chain complementarity determining region 2 (CDR-H2) comprising the amino acid sequence of SEQ ID NO: 10, and a heavy chain complementarity determining region 3 (CDR-H3) comprising the amino acid sequence of SEQ ID NO: 11.

2. The antibody or antibody fragment of claim 1, wherein the HLA PHOX2B$_{QYNPIRTTF}$ complex comprises:

a peptide comprising the amino acid sequence of SEQ ID NO: 1, and an HLA α-chain polypeptide and a β2 microglobulin polypeptide.

3. The antibody or antibody fragment of claim 2, wherein the HLA a-chain polypeptide is HLA-A*24:02, HLA-A*23:01, HLA-B*14:02, HLA-C*07:01, HLA-C*06:02, HLA-A*29:02, or HLA-A*32:01.

4. The antibody or antibody fragment of claim 1, wherein:

the VL comprises an amino acid sequence having at least 90% sequence identity to SEQ ID NO: 4; and the VH comprises an amino acid sequence having at least 90% sequence identity to SEQ ID NO: 5.

5. The antibody or antibody fragment of claim 4, wherein the VL comprises the amino acid sequence of SEQ ID NO: 4, and the VH comprises the amino acid sequence of SEQ ID NO: 5.

6. The antibody or antibody fragment of claim 1, wherein the antibody fragment is a single-chain variable fragment (scFv).

7. A polynucleotide comprising a nucleic acid sequence encoding the scFv of claim 6.

8. A chimeric antigen receptor (CAR) that binds an HLA PHOX2B$_{QYNPIRTTF}$ complex, the CAR comprising:

(i) a light chain variable domain (VL) comprising:

a light chain complementarity determining region 1 (CDR-L1) comprising the amino acid sequence of SEQ ID NO: 6, a light chain complementarity determining region 2 (CDR-L2) comprising the amino acid sequence of SEQ ID NO: 7, and a light chain complementarity determining region 3 (CDR-L3) comprising the amino acid sequence of SEQ ID NO: 8; and (ii) a heavy chain variable domain (VH) comprising:

a heavy chain complementarity determining region 1 (CDR-H1) comprising the amino acid sequence of SEQ ID NO: 9, a heavy chain complementarity determining region 2 (CDR-H2) comprising the amino acid sequence of SEQ ID NO: 10, and a heavy chain complementarity determining region 3 (CDR-H3) comprising the amino acid sequence of SEQ ID NO: 11.

9. The CAR of claim 8, wherein the HLA PHOX2B$_{QYNPIRTTF}$ complex comprises:

a peptide comprising the amino acid sequence of SEQ ID NO: 1, and an HLA α-chain polypeptide and a β2 microglobulin polypeptide.

10. The CAR of claim 9, wherein the HLA a-chain polypeptide is HLA-A*24:02, HLA-A*23:01, HLA-B*14:02, HLA-C*07:01, HLA-C*06:02, HLA-A*29:02, or HLA-A*32:01.

11. The CAR of claim 8, wherein:

the VL comprises an amino acid sequence having at least 90% sequence identity to SEQ ID NO: 4; and the VH comprises an amino acid sequence having at least 90% sequence identity to SEQ ID NO: 5.

12. The CAR of claim 11, wherein the VL comprises the amino acid sequence of SEQ ID NO: 4, and the VH comprises the amino acid sequence of SEQ ID NO: 5.

13. The CAR of claim 8, wherein the CAR comprises a 4-1BB intracellular signaling domain and a CD3-zeta intracellular signaling domain.

14. The CAR of claim 8, wherein the CAR comprises an amino acid sequence having at least 90% sequence identity to SEQ ID NO: 21.

15. The CAR of claim 14, wherein the CAR comprises the amino acid sequence of SEQ ID NO: 21.

16. A polynucleotide comprising a nucleic acid sequence encoding the CAR of claim 8.

17. A CAR T cell comprising the CAR of claim 8.

18. A method of treating a tumor expressing an HLA PHOX2B$_{QYNPIRTTF}$ complex in an individual, the method comprising:

administering to the individual, a CAR T cell that binds an HLA PHOX2B$_{QYNPIRTTF}$ complex, wherein the CAR T cell comprises:

(i) a light chain variable domain (VL) comprising:

a light chain complementarity determining region 1 (CDR-L1) comprising the amino acid sequence of SEQ ID NO: 6, a light chain complementarity determining region 2 (CDR-L2) comprising the amino acid sequence of SEQ ID NO: 7, and a light chain complementarity determining region 3 (CDR-L3) comprising the amino acid sequence of SEQ ID NO: 8; and (ii) a heavy chain variable domain (VH) comprising:

a heavy chain complementarity determining region 1 (CDR-H1) comprising the amino acid sequence of SEQ ID NO: 9, a heavy chain complementarity determining region 2 (CDR-H2) comprising the amino acid sequence of SEQ ID NO: 10, and a heavy chain complementarity determining region 3 (CDR-H3) comprising the amino acid sequence of SEQ ID NO: 11.

19. The method of claim 18, wherein the tumor is a neuroblastoma tumor.

* * * * *